(12) United States Patent
Klaveness et al.

(10) Patent No.: US 11,142,520 B2
(45) Date of Patent: Oct. 12, 2021

(54) LDHA ACTIVITY INHIBITORS

(71) Applicant: ARCTIC PHARMA AS, Oslo (NO)

(72) Inventors: Jo Klaveness, Oslo (NO); Bora Sieng, Oslo (NO); Steffi Lundvall, Oslo (NO); Claudia Alejandra Bøen, Oslo (NO); Kathrin Hnida, Oslo (NO)

(73) Assignee: ARCTIC PHARMA AS, Oslo (NO)

( * ) Notice: Subject to any disclaimer, the term of this patent is extended or adjusted under 35 U.S.C. 154(b) by 0 days.

(21) Appl. No.: 16/613,837

(22) PCT Filed: May 16, 2018

(86) PCT No.: PCT/GB2018/051333
§ 371 (c)(1),
(2) Date: Nov. 15, 2019

(87) PCT Pub. No.: WO2018/211277
PCT Pub. Date: Nov. 22, 2018

(65) Prior Publication Data
US 2020/0165233 A1    May 28, 2020

(30) Foreign Application Priority Data

May 16, 2017 (GB) ..................... 1707856

(51) Int. Cl.
*C07D 409/14* (2006.01)
*A61P 35/00* (2006.01)
*C07D 413/14* (2006.01)

(52) U.S. Cl.
CPC ............ *C07D 409/14* (2013.01); *A61P 35/00* (2018.01); *C07D 413/14* (2013.01)

(58) Field of Classification Search
CPC ............................. A61P 35/00; C07D 413/14
See application file for complete search history.

(56) References Cited

U.S. PATENT DOCUMENTS

| 5,789,440 | A | * | 8/1998 | Ellsworth | ............ | C07D 405/12 |
| | | | | | | 514/460 |
| 5,840,751 | A | * | 11/1998 | Ellsworth | ............ | C07C 323/22 |
| | | | | | | 514/464 |
| 2020/0102293 | A1 | * | 4/2020 | Klaveness | ............ | C07D 409/04 |
| 2020/0163950 | A1 | * | 5/2020 | Sieng | ................. | A61K 31/5377 |

FOREIGN PATENT DOCUMENTS

| EP | 0729463 B1 | 10/1994 |
| WO | 2015140133 A1 | 9/2015 |
| WO | 2015142903 A2 | 9/2015 |
| WO | 2017055396 A1 | 9/2016 |

OTHER PUBLICATIONS

Fauber; Bioorg. Med. Chem. Lett. 2014, 24, 5683-5687. (Year: 2014).*
International Search Report and Written Opinion in PCT/GB2018/051333. dated Apr. 7, 2018. 9 pages.
Purkey H.E.; "Cell Active Hydroxylactam Inhibitors of Human Lactate Dehydrogenase with Oral Bioavailability in Mice", ACS Medicinal Chemistry Letters, vol. 7, Aug. 26, 2016.
Boudreau, Aaron et al. "Metabolic plasticity underpins innate and acquired resistance to LDHA inhibition" Nature Chemical Biology, DOI: 10.1038/NCHEMBIO.2143, Aug. 1, 2016.

* cited by examiner

*Primary Examiner* — Daniel R Carcanague
(74) *Attorney, Agent, or Firm* — Meunier Carlin & Curfman LLC

(57) ABSTRACT

The invention provides compounds of formula (I), stereoisomers, tautomers, pharmaceutically acceptable salts and prodrugs thereof: (I) wherein $A_1$ to $A_6$ and $R_1$ to $R_4$ are as defined herein. Such compounds are suitable for use in the treatment or prevention of diseases or conditions which are mediated by the activation of lactate dehydrogenase A (LDHA), for example cancer.

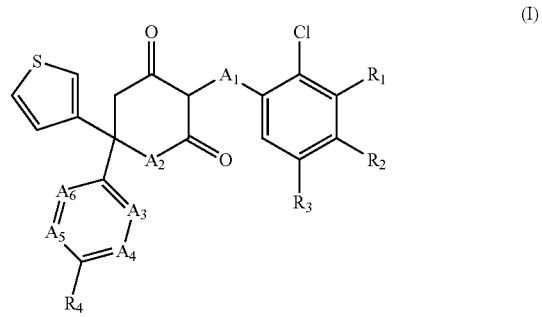

38 Claims, 12 Drawing Sheets

LDHA ACTIVITY INHIBITORS

FIELD OF INVENTION

The present invention relates to novel compounds, to pharmaceutical compositions containing them and their use as medicaments.

More specifically, the present invention relates to compounds which inhibit lactate dehydrogenase A ("LDHA") activity. These compounds find use in the treatment or prevention of diseases or conditions which are mediated by the activation of LDHA, including diseases which are characterized by hyperproliferative cells such as cancer.

The compounds find particular use against hypoxic and/or highly glycolytic cancers such as pancreatic cancer and breast cancer.

BACKGROUND OF INVENTION

In the presence of oxygen, normal differentiated cells primarily rely on oxidative phosphorylation in mitochondria to generate energy in the form of ATP. Glucose is first metabolized in the cytosol via the glycolysis pathway leading to the production of pyruvate. Pyruvate is then further converted to $CO_2$ in the mitochondrial tricarboxylic acid cycle. The latter process is linked to the production of NADH which drives ATP production during oxidative phosphorylation.

Healthy cells react to low oxygen levels by a process termed "anaerobic glycolysis." During anaerobic glycolysis pyruvate is converted into lactate to allow continuous regeneration of NAD+ which is crucial for glycolysis. Cancer cells, however, primarily rely on glucose fermentation and the produced pyruvate is converted to lactate, even in the presence of adequate oxygen levels. This shift to "aerobic glycolysis" in cancer cells is termed the "Warburg effect".

Aerobic glycolysis provides tumor cells with the ability to incorporate more carbon into biomass and to produce the ATP needed for cellular processes independent of oxygen. It has been shown in several studies that this change in glycolytic metabolism correlates to increased glucose uptake in cancer cells which results in poor prognosis and an increase in tumor aggression. Several glycolytic enzymes in the glucose metabolic pathway may associate with aerobic glycolysis. Interference with this metabolic pathway through the inhibition of various metabolic enzymes has previously been proposed as an approach to the treatment of cancer and other metabolic diseases. However, targeting the altered metabolism of cancer itself has yet to be addressed by a commercially available drug.

The conversion of pyruvate to lactate is catalyzed by the enzyme lactate dehydrogenase (LDH), which uses NADH as a cofactor. The enzyme comprises a tetrameric structure, built up by combinations of two subunits, LDHA (M, muscle) and LDHB (H, heart). The structural arrangement of these subunits gives rise to five isoforms: the two homotetramers LDH1 ($H_4$, LDHB) found predominantly in the heart and LDH5 ($M_4$, LDHA) which is present in skeletal muscle, as well as three heterotetramers which are found in other tissues (e.g. the lungs and kidneys). The sixth isoform, the homotetramer LDHC ($C_4$), is testis- and sperm-specific and is linked to male fertility.

Several studies have shown that LDHA plays a critical role in the survival of tumors and that its expression is upregulated in cancerous tissues. Elevated levels of lactate lead to extracellular acidosis which enables tumor invasion and metastasis. Reports describing that silencing of LDHA expression leads to reduced tumor proliferation in hypoxia, reduced tumor growth and stimulation of mitochondrial respiration point to the strong potential of metabolic alteration in cancer treatment. In addition, patients with a lactate dehydrogenase M-subunit deficiency have no symptoms of muscle rigidity or myoglobinuria under aerobic conditions confirming LDHA is a safe drug target and inhibition of it will not lead to severe side-effects.

LDHA plays a crucial role in the promotion of glycolysis in invasive tumor cells as it contributes to the depletion of the pyruvate pool produced by glycolytic activity. Pyruvate would otherwise be available for oxidative decarboxylation and further downstream reactions in cellular respiration. Over-expression of LDHA is detected in many types of cancer cells and shRNA-mediated LDHA knock-down results in significant inhibition of tumor growth in glycolytically dependent cancer cell lines. The reverse reaction—in which exogenous lactate is converted to endogenous pyruvate—is catalyzed by lactate dehydrogenase B ("LDHB"). LDHB is mainly found in the heart and red blood cells where it contributes to the energy production in the beating heart during exercise where a surplus of lactate from anaerobic muscle activity is high. This suggests that the ability to achieve selectivity over this particular enzyme would be desirable. The capability to inhibit LDHA activity, and in particular to "selectively" inhibit LDHA activity, thus represents an attractive approach to the development of new therapeutic methods of treating cancer and associated diseases.

Several LDHA inhibitors have been reported and proposed for use in the treatment of various cancers. Amongst these are certain piperidine-dione compounds described by Genentech, Inc. in WO 2015/140133. A number of the compounds disclosed in this earlier application were found to exhibit low LDHA $IC_{50}$ values in an LDHA enzyme inhibition assay, however, inhibition assays in cancer cells were lacking.

A related application filed by Genentech, Inc., WO 2015/142903, relates to the control of lactate production in mammalian cell cultures used to produce recombinant proteins. The same piperidine-dione compounds are described and tested for their capacity to inhibit LDHA in the same LDHA enzyme inhibition assay. Compound 44 (referred to as "Gx" in WO 2015/142903—see structure below) is tested in CHO cells derived from a CHO-K1 host stably transfected to produce a recombinant humanized monoclonal antibody in order to determine its effect on CHO cell growth, culture viability, lactate production and product yield. "Gx" has the following structure:

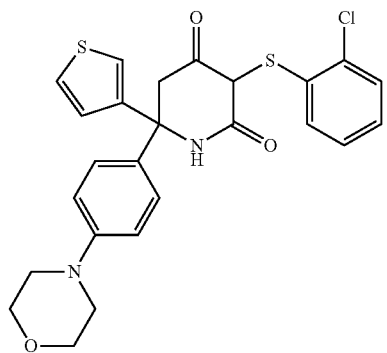 [SMILES: O=C1CC(c2ccc(N3CCOCC3)cc2)(c2ccsc2)NC(=O)C1Sc1ccccc1Cl]

In a later paper authored by the inventors of these earlier Genentech applications, this particular LDHA inhibitor (in the paper referred to as "GNE-140") was used to probe the role of LDHA in tumor growth in vitro and in vivo (see Nature Chemical Biology DOI:10.1038/NCHEMBIO.2143, 1 Aug. 2016). In MIA PaCa-2 human pancreatic cells, LDHA inhibition by "GNE-140" rapidly affected global metabolism, although cell death only occurred after 2 days of continuous LDHA inhibition. Notably, in vivo, "GNE-140" was unable to sustain inhibition of LDHA for more than 1 hour due to its rapid clearance. The authors concluded that LDHA inhibitors require pharmacokinetic properties that can provide sustained in vivo target modulation for multiple days in order to increase their clinical utility.

Thus a need for alternative LDHA inhibitors still exists.

We have now found a selected class of compounds which exhibit LDHA inhibitory activity and which, at least in some embodiments, exhibit "selective" LDHA inhibitory activity. These compounds provide an alternative to LDHA inhibitors known in the prior art, such as those described in WO 2015/140133 and in WO 2015/142903. Their properties render them particularly suitable for use in the treatment or prevention of conditions or disorders which are mediated by the activation of LDHA, for example as anti-cancer agents for use against hypoxic and/or highly glycolytic tumors.

As will be described herein, at least in some embodiments, the compounds according to the invention provide an improvement over those disclosed in WO 2015/140133 and in WO 2015/142903.

SUMMARY OF THE INVENTION

In one aspect, the invention relates to compounds of formula (I), their stereoisomers, tautomers, pharmaceutically acceptable salts and prodrugs:

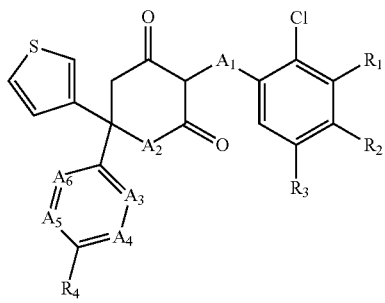
(I)

wherein:
$A_1$ is —O—, —CH$_2$—, or —S—;
$A_2$ is NR (wherein R is either H or $C_{1-3}$ alkyl), or —O—;
$A_3$ is N or $CR_5$;
$A_4$ is N or $CR_6$;
$A_5$ is N or $CR_7$;
$A_6$ is N or $CR_8$;
$R_1$, $R_2$ and $R_3$ are independently selected from H and halogen;
$R_4$ is selected from:
H;
halogen;
a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —CO$_2$H, —C(O)—O—$C_{1-6}$ alkyl, —C(O)—$C_{1-6}$ alkyl, amino, cyano, and nitro groups;
$OR_9$ in which $R_9$ is a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —CO$_2$H, —C(O)—O—$C_{1-6}$ alkyl, —C(O)—$C_{1-6}$ alkyl, amino, cyano, and nitro groups; and
$OR_{10}$ in which $R_{10}$ is a $C_{3-8}$ cycloalkyl group;
$R_5$ is selected from:
H;
hydroxy;
$C_{1-6}$ alkyl; and
$C_{1-6}$ alkoxy;
$R_6$ is selected from:
H;
halogen;
$C_{1-6}$ alkyl optionally substituted by one or more substituents selected from the group consisting of halogen, hydroxy, $C_{1-6}$ alkoxy, $C_{1-6}$ haloalkyl, $C_{1-6}$ hydroxyalkyl, amino, cyano, and nitro groups;
$C_{1-6}$ alkoxy optionally substituted by one or more substituents selected from the group consisting of halogen, hydroxy, $C_{1-6}$ alkoxy, $C_{1-6}$ haloalkyl, $C_{1-6}$ hydroxyalkyl, amino, cyano, nitro, and $C_{3-8}$ cycloalkyl groups;
a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —CO$_2$H, —C(O)—O—$C_{1-6}$ alkyl, —C(O)—$C_{1-6}$ alkyl, amino, cyano, and nitro groups;
$OR_{11}$ in which $R_{11}$ is a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —CO$_2$H, —C(O)—O—$C_{1-6}$ alkyl, —C(O)—$C_{1-6}$ alkyl, amino, cyano, and nitro groups; and
$OR_{12}$ in which $R_{12}$ is a $C_{3-8}$ cycloalkyl group;
$R_7$ and $R_8$ are independently selected from:
H;
hydroxy;
$C_{1-6}$ alkyl; and
$C_{1-6}$ alkoxy;
with the provisos that:
$A_3$ and $A_4$ are not both N at the same time;
$A_5$ and $A_6$ are not both N at the same time; and
when $A_2$ is NR, at least one of $R_1$, $R_2$ and $R_3$ is halogen.

In a further aspect, the invention relates to tautomers of compounds of formula (I) and derivatives thereof, such as the compounds of formula (Ia), their stereoisomers, pharmaceutically acceptable salts and prodrugs:

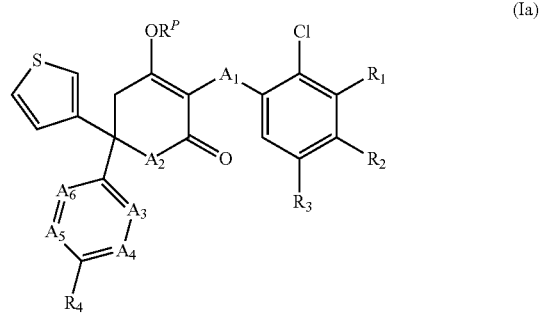
(Ia)

wherein $A_1$ to $A_6$ and $R_1$ to $R_4$ are as defined herein; and $R^P$ is either H or a group having the formula (II):

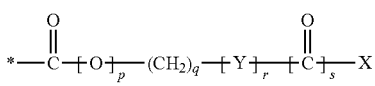

(II)

wherein:
* denotes the point of attachment of the group to the remainder of the molecule;
Y is —O— or $NR^i$ where $R^i$ is either H or $C_{1-3}$ alkyl (e.g. $CH_3$);
X is selected from:
H;
hydroxy;
$NR^jR^k$ where $R^j$ and $R^k$ are each independently selected from H and $C_{1-6}$ alkyl (preferably $C_{1-3}$ alkyl, e.g. $CH_3$);
—$C_{1-12}$ alkyl optionally substituted by one or more hydrophilic groups;
—$C_{1-12}$ alkyl optionally substituted by one or more aryl or heteroaryl groups, which aryl and heteroaryl groups may optionally be substituted by one or more substituents selected from the group consisting of: halo, hydroxy, $C_{1-6}$ alkyl, $C_{1-6}$ alkoxy, $C_{1-6}$ haloalkyl, $C_{1-6}$ haloalkoxy and $C_{1-6}$ hydroxyalkyl groups; and
an aryl or heteroaryl group which may optionally be substituted by one or more substituents selected from the group consisting of: halo, hydroxy, $C_{1-6}$ alkyl, $C_{1-6}$ alkoxy, $C_{1-6}$ haloalkyl, $C_{1-6}$ haloalkoxy and $C_{1-6}$ hydroxyalkyl groups;
p is 0 or 1;
q is an integer from 0 to 6;
r is 0 or 1; and
s is 0 or 1.

In a further aspect, the invention relates to pharmaceutical compositions comprising a compound of formula (I) or (Ia), a stereoisomer, tautomer, pharmaceutically acceptable salt or prodrug thereof, together with one or more pharmaceutically acceptable carriers, excipients or diluents.

In a further aspect, the invention relates to a compound of formula (I) or (Ia), a stereoisomer, tautomer, pharmaceutically acceptable salt or prodrug thereof, for use in therapy or for use as a medicament.

In a further aspect, the invention relates to a compound of formula (I) or (Ia), a stereoisomer, tautomer, pharmaceutically acceptable salt or prodrug thereof, for use in the inhibition of LDHA, for example for use in the "selective" inhibition of LDHA over LDHB.

In a further aspect, the invention relates to compound of formula (I) or (Ia), a stereoisomer, tautomer, pharmaceutically acceptable salt or prodrug thereof, for use in the treatment or prevention of a disease or disorder responsive to inhibition of LDHA, for example a disease or disorder which is mediated by activation of LDHA, preferably for use in the treatment or prevention of a proliferative disorder such as cancer.

A further aspect of the invention relates to the use of a compound of formula (I) or (Ia), a stereoisomer, tautomer, pharmaceutically acceptable salt or prodrug thereof, in the manufacture of a medicament for use in the treatment or prevention of a disease or disorder responsive to inhibition of LDHA, for example a disease or disorder which is mediated by activation of LDHA, preferably for use in the treatment or prevention of a proliferative disorder such as cancer.

A yet further aspect of the invention relates to a method of treatment or prevention of a disease or disorder responsive to inhibition of LDHA, for example a disease or disorder which is mediated by activation of LDHA, said method comprising the step of administering to a patient in need thereof (e.g. a human subject) a pharmaceutically effective amount of a compound of formula (I) or (Ia), a stereoisomer, tautomer, pharmaceutically acceptable salt or prodrug thereof.

DETAILED DESCRIPTION OF THE INVENTION

Definitions

The term "alkyl" as used herein refers to a monovalent saturated, linear or branched, carbon chain. Examples of alkyl groups include, but are not limited to, methyl, ethyl, n-propyl, iso-propyl, n-butyl, iso-butyl, sec-butyl, tert-butyl, n-pentyl, iso-pentyl, neo-pentyl, n-hexyl, etc. An alkyl group preferably contains from 1-6 carbon atoms, e.g. 1-4 carbon atoms. Unless otherwise specified, any alkyl group may be substituted in one or more positions with a suitable substituent. Where more than one substituent group is present, these may be the same or different. Suitable substituents include hydroxy, $C_{1-6}$ alkoxy, amino, cyano, and nitro groups, or halogen atoms (e.g. F, Cl or Br).

The term "alkoxy" as used herein refers to an —O-alkyl group, wherein alkyl is as defined herein. Examples of alkoxy groups include, but are not limited to, methoxy, ethoxy, propyloxy, etc. Unless otherwise specified, any alkoxy group may be substituted in one or more positions with a suitable substituent. Where more than one substituent group is present, these may be the same or different. Suitable substituents include hydroxy, $C_{1-6}$ alkoxy, amino, cyano, and nitro groups, or halogen atoms (e.g. F, Cl or Br).

The term "aryl" as used herein refers to aromatic ring systems. Such ring systems may be monocyclic or bicyclic and contain at least one unsaturated aromatic ring. Where these contain bicyclic rings, these may be fused. Preferably such systems contain from 6-20 carbon atoms, e.g. either 6 or 10 carbon atoms. Examples of such groups include phenyl, I-napthyl and 2-napthyl. A preferred aryl group is phenyl. Unless stated otherwise, any aryl group may be substituted by one or more substituents as described herein. Where more than one substituent group is present, these may be the same or different.

The term "cycloalkyl" refers to a monovalent, saturated cyclic carbon system. It includes monocyclic and bicyclic rings. Monocyclic rings may contain from 3 to 8 carbon atoms and bicyclic rings may contain from 7 to 14 carbon atoms. Examples of monocyclic cycloalkyl groups include, but are not limited to, cyclopropyl, cyclobutyl, cyclopentyl, cyclohexyl, cycloheptyl, etc. Unless otherwise specified, any cycloalkyl group may be substituted in one or more positions with a suitable substituent. Where more than one substituent group is present, these may be the same or different. Suitable substituents include hydroxy, $C_{1-6}$ alkoxy, amino, cyano, and nitro groups, or halogen atoms (e.g. F, Cl or Br).

The terms "halogen", "halo" or "halogen atom" are used interchangeably herein and refer to —F, —Cl, —Br or —I.

The term "haloalkyl" refers to an alkyl group as defined herein in which at least one of the hydrogen atoms of the alkyl group is replaced by a halogen atom, preferably F, Cl or Br. Examples of such groups include —$CH_2F$, —$CHF_2$, —$CF_3$, —$CCl_3$, —$CHCl_2$, —$CH_2CF_3$, etc.

The term "hydroxyalkyl" refers to an alkyl group as defined herein in which at least one of the hydrogen atoms of the alkyl group is replaced by a hydroxy group. Examples of such groups include methyl, ethyl, n-propyl, iso-propyl, n-butyl, iso-butyl, sec-butyl, tert-butyl, n-pentyl, iso-pentyl, neo-pentyl, n-hexyl, etc. in which one or more hydrogen atoms are replaced by —OH.

The term "heterocyclic ring" as used herein refers to a saturated or partially unsaturated, 4- to 6-membered (preferably 5- or 6-membered) carbocyclic system in which at least one ring atom is a heteroatom selected from nitrogen, oxygen and sulfur, the remaining ring atoms being carbon. The heterocyclic ring structure may be linked to the remainder of the molecule through a carbon atom or through a nitrogen atom. Examples of heterocyclic rings include, but are not limited to, tetrahydrofuran, piperidine, pyrrolidine, dioxane, morpholine, etc. Unless otherwise stated, any heterocyclic ring mentioned herein may optionally be substituted by one or more groups, which may be identical or different, for example hydroxy, $C_{1-6}$ alkyl, $C_{1-6}$ alkoxy, amino, cyano, or nitro groups, or halogen atoms (e.g. F, Cl or Br).

As used herein, the term "heteroaryl" refers to heterocyclic aromatic groups. Such groups may be monocyclic or bicyclic and contain at least one unsaturated heteroaromatic ring system. Where these are monocyclic, these comprise 5- or 6-membered rings which contain at least one heteroatom selected from nitrogen, oxygen and sulfur and contain sufficient conjugated bonds to form an aromatic system. Where these are bicyclic, these may contain from 9-11 ring atoms. Examples of heteroaryl groups include thiophene, thienyl, pyridyl, thiazolyl, furyl, pyrrolyl, triazolyl, imidazolyl, oxadiazolyl, oxazolyl, pyrazolyl, imidazolonyl, oxazolonyl, thiazolonyl, tetrazolyl, thiadiazolyl, benzimidazolyl, benzooxazolyl, benzofuryl, indolyl, isoindolyl, pyridonyl, pyridazinyl, pyrimidinyl, imidazopyridyl, oxazopyridyl, thiazolopyridyl, imidazopyridazinyl, oxazolopyridazinyl, thiazolopyridazinyl and purinyl. Unless otherwise stated, any heteroaryl ring mentioned herein may optionally be substituted by one or more groups as described herein. Where more than one substituent group is present, these may be the same or different.

The term "hydrophilic group" refers to a substituent group which is capable of hydrogen bonding. Examples of hydrophilic groups include, but are not limited to, hydroxy, thiol, and amine.

Where reference is made to one or more substituents, this refers to substitution by 1 to 12 substituents that can be independently selected from the groups defined herein. In one embodiment, 1, 2, 3, 4, 5 or 6 substituents may be present, preferably 1, 2, or 3, e.g. 1 or 2.

The compounds of the invention may contain one or more stereocenters and may therefore exist in different stereoisomeric forms. The term "stereoisomer" refers to compounds which have identical chemical constitution but which differ in respect of the spatial arrangement of the atoms or groups. Examples of stereoisomers are enantiomers and diastereomers. The term "enantiomers" refers to two stereoisomers of a compound which are non-superimposable mirror images of one another. The term "diastereoisomers" refers to stereoisomers with two or more stereocentres which are not mirror images of one another. The invention is considered to extend to diastereomers and enantiomers, as well as racemic mixtures and enantioenriched mixtures in which the ratio of enantiomers is other than 1:1.

The compounds herein described may be resolved into their enantiomers and/or diastereomers. For example, where these contain only one stereocenter, these may be provided in the form of a racemate or racemic mixture (a 50:50 mixture of enantiomers) or may be provided as pure enantiomers, i.e. in the R- or S-form. Any of the compounds which occur as racemates may be separated into their enantiomers by methods known in the art, such as column separation on chiral phases or by recrystallization from an optically active solvent. Those compounds with at least two asymmetric carbon atoms may be resolved into their diastereomers on the basis of their physical-chemical differences using methods known per se, e.g. by chromatography and/or fractional crystallization, and where these compounds are obtained in racemic form, they may subsequently be resolved into their enantiomers.

The term "tautomer" as used herein refers to structural isomers which readily interconvert by way of a chemical reaction which may involve the migration of a proton accompanied by a switch of a single bond and adjacent double bond. It includes, in particular, keto-enol tautomers. Dependent on the conditions, the compounds may predominantly exist either in the keto or enol form and the invention is not intended to be limited to the particular form shown in any of the structural formulae given herein.

The term "pharmaceutically acceptable salt" as used herein refers to any pharmaceutically acceptable organic or inorganic salt of any of the compounds herein described. A pharmaceutically acceptable salt may include one or more additional molecules such as counter-ions. The counter-ions may be any organic or inorganic group which stabilizes the charge on the parent compound. If the compound of the invention is a base, a suitable pharmaceutically acceptable salt may be prepared by reaction of the free base with an organic or inorganic acid. If the compound of the invention is an acid, a suitable pharmaceutically acceptable salt may be prepared by reaction of the free acid with an organic or inorganic base. Non-limiting examples of suitable salts are described herein.

The term "pharmaceutically acceptable" means that the compound or composition is chemically and/or toxicologically compatible with other components of the formulation or with the patient (e.g. human) to be treated.

By "a pharmaceutical composition" is meant a composition in any form suitable to be used for a medical purpose.

The term "prodrug" refers to a derivative of an active compound which undergoes a transformation under the conditions of use, for example within the body, to release an active drug. A prodrug may, but need not necessarily, be pharmacologically inactive until converted into the active drug. As used herein, the term "prodrug" extends to any compound which under physiological conditions is converted into any of the active compounds herein described. Suitable prodrugs include compounds which are hydrolyzed under physiological conditions to the desired molecule, or which are transformed to the active drug by the action of enzymes in vivo.

Prodrugs may typically be obtained by masking one or more functional groups in the parent molecule which are considered to be, at least in part, required for activity using a progroup. By "progroup" as used herein is meant a group which is used to mask a functional group within an active drug and which undergoes a transformation, such as cleavage, under the specified conditions of use (e.g. administration to the body) to release a functional group and hence provide the active drug. Progroups are typically linked to the functional group of the active drug via a bond or bonds that are cleavable under the conditions of use, e.g. in vivo. Cleavage of the progroup may occur spontaneously under the conditions of use, for example by way of hydrolysis, or it may be catalyzed or induced by other physical or chemical means, e.g. by an enzyme, by exposure to light, by exposure to a change in temperature, or to a change in pH, etc. Where cleavage is induced by other physical or chemical means, these may be endogenous to the conditions of use, for example pH conditions at a target tumor site, or these may be supplied exogenously.

As used herein, "treatment" includes any therapeutic application that can benefit a human or non-human animal (e.g. a non-human mammal). Both human and veterinary treatments are within the scope of the present invention, although primarily the invention is aimed at the treatment of humans. Treatment may be in respect of an existing disease or condition or it may be prophylactic.

As used herein, a "pharmaceutically effective amount" relates to an amount that will lead to the desired pharmacological and/or therapeutic effect, i.e. an amount of the agent which is effective to achieve its intended purpose. While individual patient needs may vary, determination of optimal ranges for effective amounts of the active agent is within the capability of one skilled in the art. Generally, the dosage regimen for treating a disease or condition with any of the compounds described herein is selected in accordance with a variety of factors including the nature of the medical condition and its severity.

As used herein, "lactate dehydrogenase A" or "LDHA" refers to an enzyme that is predominantly expressed in muscle and which converts pyruvate that originates from glycolysis to lactate, coupled with oxidation of NADH to NAD+.

Any reference herein to "lactate dehydrogenase A activity" or "LDHA activity" relates to the conversion of pyruvate to lactate, to a cell proliferative activity, or to any other enzymatic activity of lactate dehydrogenase A, or a fragment thereof. Reference to a "lactate dehydrogenase A inhibitor" or "inhibition of lactate dehydrogenase A" should be construed accordingly. A "lactate dehydrogenase A inhibitor" is thus a compound that reduces the conversion of pyruvate to lactate by lactate dehydrogenase A, that reduces a lactate dehydrogenase A proliferative activity, or that otherwise reduces a lactate dehydrogenase A enzymatic activity. Such a reduction need not be complete but will typically be a reduction of at least about 10%, 20%, 30%, 40%, 50%, 60%, 70%, 80%, or may be as high as at least 90% or at least 95%. In certain embodiments of the invention, the compounds herein described "selectively" inhibit an enzymatic activity of lactate dehydrogenase A. Such inhibition is considered to be "selective" as long as the compound inhibits the activity of lactate dehydrogenase A to a greater extent than it inhibits that of lactate dehydrogenase B.

The invention is based, at least in part, on the finding that certain modifications to known LDHA inhibitors leads to compounds which not only retain their LDHA inhibitory activity, but which may also exhibit selectivity for LDHA inhibition. This discovery leads to the use of the compounds to treat conditions or diseases in subjects, e.g. in humans, which are mediated by the activation of LDHA. Cellular membrane permeability of the compounds is further improved when these are provided in the form of certain derivatives as herein described.

In one aspect, the invention provides compounds of formula (I), their stereoisomers, tautomers, pharmaceutically acceptable salts, and prodrugs:

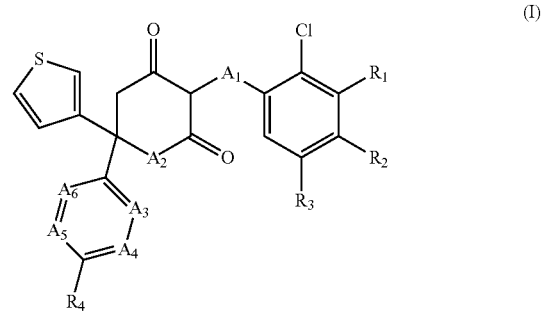

(I)

wherein:
$A_1$ is —O—, —$CH_2$—, or —S—;
$A_2$ is NR (wherein R is either H or $C_{1-3}$ alkyl), or —O—;
$A_3$ is N or $CR_5$;
$A_4$ is N or $CR_6$;
$A_5$ is N or $CR_7$;
$A_6$ is N or $CR_8$;
$R_1$, $R_2$ and $R_3$ are independently selected from H and halogen;
$R_4$ is selected from:
H;
halogen;
a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —$CO_2H$, —C(O)—O—$C_{1-6}$ alkyl, —C(O)—$C_{1-6}$ alkyl, amino, cyano, and nitro groups; and $OR_9$ in which $R_9$ is a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —$CO_2H$, —C(O)—O—$C_{1-6}$ alkyl, —C(O)—$C_{1-6}$ alkyl, amino, cyano, and nitro groups; and
$OR_{10}$ in which $R_{10}$ is a $C_{3-8}$ cycloalkyl group;
$R_5$ is selected from:
H;
hydroxy;
$C_{1-6}$ alkyl; and
$C_{1-6}$ alkoxy;
$R_6$ is selected from:
H;
halogen;
$C_{1-6}$ alkyl optionally substituted by one or more substituents selected from the group consisting of halogen, hydroxy, $C_{1-6}$ alkoxy, $C_{1-6}$ haloalkyl, $C_{1-6}$ hydroxyalkyl, amino, cyano, and nitro groups;
$C_{1-6}$ alkoxy optionally substituted by one or more substituents selected from the group consisting of halogen, hydroxy, $C_{1-6}$ alkoxy, $C_{1-6}$ haloalkyl, $C_{1-6}$ hydroxyalkyl, amino, cyano, nitro, and $C_{3-8}$ cycloalkyl groups;
a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —$CO_2H$, —C(O)—O—$C_{1-6}$ alkyl, —C(O)—$C_{1-6}$ alkyl, amino, cyano, and nitro groups;
$OR_{11}$ in which $R_{11}$ is a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —CO₂H, —C(O)—O—C₁₋₆ alkyl, —C(O)—C₁₋₆ alkyl, amino, cyano, and nitro groups; and OR₁₂ in which R₁₂ is a C₃₋₈ cycloalkyl group;

R₇ and R₈ are independently selected from:
H;
hydroxy;
C₁₋₆ alkyl; and
C₁₋₆ alkoxy;
with the provisos that:
A₃ and A₄ are not both N at the same time;
A₅ and A₆ are not both N at the same time; and
when A₂ is NR, at least one of R₁, R₂ and R₃ is halogen.

In a further aspect, the invention provides compounds of formula (Ia), their tautomers, stereoisomers, pharmaceutically acceptable salts and prodrugs:

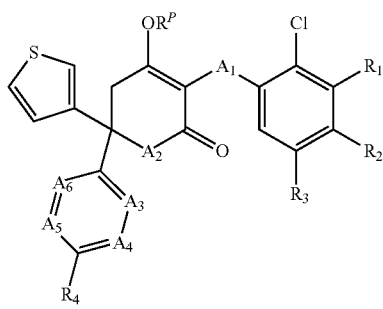

(Ia)

wherein A₁ to A₆ and R₁ to R₄ are as defined herein; and R^P is either H or a group having the formula (II):

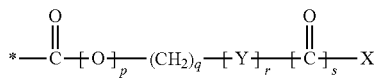

(II)

wherein:
* denotes the point of attachment of the group to the remainder of the molecule;
Y is —O— or NR^i where R^i is either H or C₁₋₃ alkyl (e.g. CH₃);
X is selected from:
H;
hydroxy;
NR^jR^k where R^j and R^k are each independently selected from H and C₁₋₆ alkyl (preferably C₁₋₃ alkyl, e.g. CH₃);
—C₁₋₁₂ alkyl optionally substituted by one or more hydrophilic groups;
—C₁₋₁₂ alkyl optionally substituted by one or more aryl or heteroaryl groups, which aryl and heteroaryl groups may optionally be substituted by one or more substituents selected from the group consisting of: halo, hydroxy, C₁₋₆ alkyl, C₁₋₆ alkoxy, C₁₋₆ haloalkyl, C₁₋₆ haloalkoxy and C₁₋₆ hydroxyalkyl groups; and
an aryl or heteroaryl group which may optionally be substituted by one or more substituents selected from the group consisting of: halo, hydroxy, C₁₋₆ alkyl, C₁₋₆ alkoxy, C₁₋₆ haloalkyl, C₁₋₆ haloalkoxy and C₁₋₆ hydroxyalkyl groups;
p is 0 or 1;
q is an integer from 0 to 6;
r is 0 or 1; and
s is 0 or 1.

Any of the embodiments herein described may relate to the compounds of formula (I) or to the compounds of formula (Ia), their tautomers, stereoisomers, pharmaceutically acceptable salts and prodrugs.

In an embodiment, A₁ is —S—.

In an embodiment, A₂ is NH or N-methyl, preferably NH.

In an embodiment, the invention relates to compounds of formula (III) and (IIIa), their tautomers, stereoisomers, pharmaceutically acceptable salts, and prodrugs:

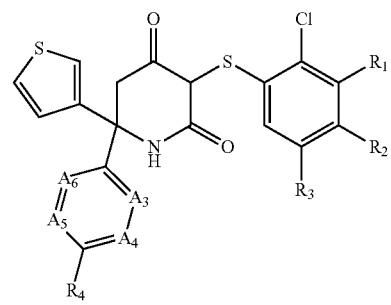

(III)

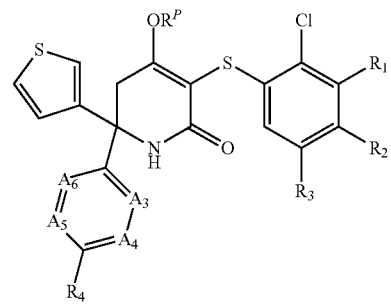

(IIIa)

wherein A₃ to A₆, R₁ to R₄ and R^P are as herein defined.

In another embodiment, A₂ is O. Where A₂ is O, R₁, R₂ and R₃ may either be H or halogen. In one embodiment A₂ is O and at least one of R₁, R₂ and R₃ is halogen.

In an embodiment, the invention relates to compounds of formula (IV) and (IVa), their tautomers, stereoisomers, pharmaceutically acceptable salts, and prodrugs:

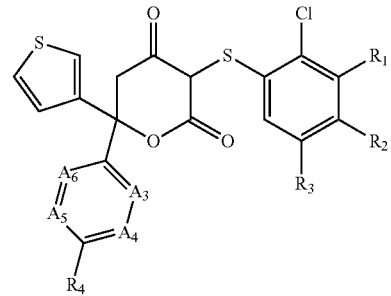

(IV)

-continued

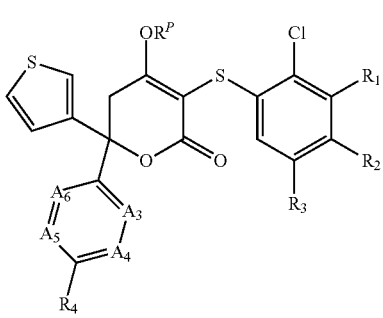

(IVa)

wherein $A_3$ to $A_6$, $R_1$ to $R_4$ and $R^P$ are as herein defined.

In one embodiment, $A_5$ is N. In one embodiment, both $A_4$ and $A_5$ are N.

In one embodiment, $A_5$ is $CR_7$ in which $R_7$ is H. In one embodiment, $A_6$ is $CR_8$ in which $R_8$ is H. In an embodiment, both $A_5$ and $A_6$ are CH.

In an embodiment, $A_3$ is N. When $A_3$ is N, $A_4$ is other than N, i.e. $CR_6$. In one embodiment, when $A_3$ is N, $A_4$ is $CR_6$ and $R_4$ is H. In another embodiment, when $A_3$ is N. $A_4$ is $CR_6$ in which $R_6$ is other than H, and $R_4$ is H. In another embodiment, when $A_3$ is N, $A_4$ is $CR_6$ in which $R_6$ is H, and $R_4$ is other than H.

In one embodiment, the invention relates to compounds of formula (V) and (Va), their tautomers, stereoisomers, pharmaceutically acceptable salts, and prodrugs:

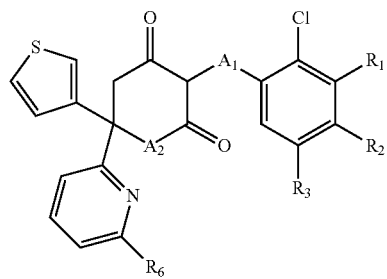

(V)

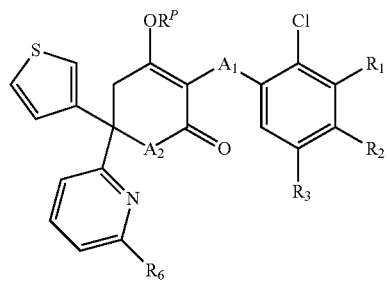

(Va)

wherein $A_1$, $A_2$, $R_1$ to $R_3$, $R_6$ and $R^P$ are as herein defined.

In one embodiment of the compounds of the invention, for example in the compounds of formula (V) and (Va), $R_6$ may be other than H. For example, $R_6$ may be selected from any of the following:

halogen;
$C_{1-6}$ alkyl optionally substituted by one or more substituents selected from the group consisting of halogen, hydroxy, $C_{1-6}$ alkoxy, $C_{1-6}$ haloalkyl, $C_{1-6}$ hydroxyalkyl, amino, cyano, and nitro groups;
$C_{1-6}$ alkoxy optionally substituted by one or more substituents selected from the group consisting of halogen, hydroxy, $C_{1-6}$ alkoxy, $C_{1-6}$ haloalkyl, $C_{1-6}$ hydroxyalkyl, amino, cyano, nitro, and $C_{3-8}$ cycloalkyl groups;
a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —$CO_2H$, —C(O)—O—$C_{1-6}$, alkyl, —C(O)—$C_{1-6}$ alkyl, amino, cyano, and nitro groups;
$OR_{11}$ in which $R_{11}$ is a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —$CO_2H$, —C(O)—O—$C_{1-6}$ alkyl, —C(O)—$C_{1-6}$ alkyl, amino, cyano, and nitro groups; and
$OR_{12}$ in which $R_{12}$ is a $C_{3-8}$ cycloalkyl group.

In an embodiment, $R_6$ is halogen (e.g. Br or Cl, preferably Br), or an optionally substituted $C_{1-6}$ alkoxy group.

In an embodiment, 1% is an optionally substituted $C_{1-6}$ alkoxy group as herein defined.

Where this is substituted, suitable substitutents include $C_{3-8}$ cycloalkyl groups, e.g. unsubstituted cyclopentyl.

In one embodiment, $A_3$ is $CR_5$. In another embodiment, $A_3$ is CH.

In one embodiment, when $A_3$ is CH, $A_4$ is $CR_6$. In another embodiment, when $A_3$ is CH, $A_4$ is $CR_6$ in which $R_6$ is H.

In one embodiment, the invention relates to compound of formula (VI) and (VIa), their tautomers, stereoisomers, pharmaceutically acceptable salts, and prodrugs:

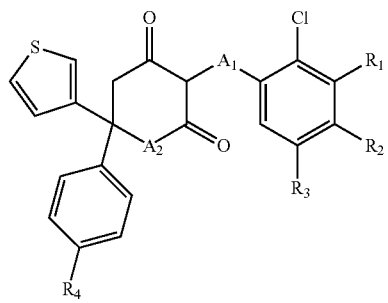

(VI)

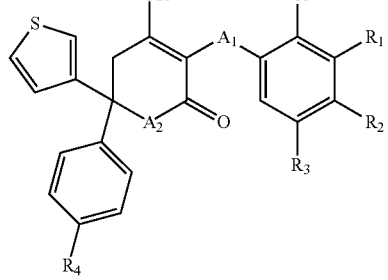

(VIa)

wherein $A_1$, $A_2$, $R_1$ to $R_4$ and $R^P$ are as herein defined.

In one embodiment of the compounds of the invention, for example in the compounds of formula (VI) and (VIa), $R_4$ may be other than H. For example, $R_4$ may be selected from any of the following:

halogen;
a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —$CO_2H$, —C(O)—O—$C_{1-6}$ alkyl, —C(O)—$C_{1-6}$ alkyl, amino, cyano, and nitro groups;

OR$_9$ in which R$_9$ is a 4- to 6-membered heterocyclic ring optionally substituted by one or more substituents selected from the group consisting of halogen, hydroxy, C$_{1-6}$ alkyl, C$_{1-6}$ alkoxy, C$_{1-6}$ haloalkyl, C$_{1-6}$ hydroxyalkyl, —CO$_2$H, —C(O)—O—C$_{1-6}$ alkyl, —C(O)—C$_{1-6}$ alkyl, amino, cyano, and nitro groups; and OR$_{10}$ in which R$_{10}$ is a C$_{3-8}$ cycloalkyl group.

In one embodiment, R$_4$ is selected from:
H;
halogen; and
a 4- to 6-membered heterocyclic ring optionally substituted by one or more substituents selected from the group consisting of halogen, hydroxy, C$_{1-6}$ alkyl, C$_{1-6}$ alkoxy, C$_{1-6}$ haloalkyl, C$_{1-6}$ hydroxyalkyl, —CO$_2$H, —C(O)—O—C$_{1-6}$ alkyl, —C(O)—C$_{1-6}$ alkyl, amino, cyano, and nitro groups.

In one embodiment, R$_4$ is selected from:
H;
Br or Cl, preferably Br; and
a 4- to 6-membered heterocyclic ring which is unsubstituted.

In one embodiment, R$_4$ is H, Br or morpholinyl.

In any of the compounds herein described, R$_1$, R$_2$ and R$_3$ are each independently selected from H and halogen provided that when A$_2$ is either NH or N—(C$_{1-3}$ alkyl) at least one of R$_1$, R$_2$ and R$_3$ is halogen.

In certain embodiments of the invention, one or two of R$_1$, R$_2$ and R$_3$ are halogen. In one embodiment, one of R$_1$, R$_2$ and R$_3$ is halogen. In another embodiment, R$_1$ is halogen and R$_2$ and R$_3$ are H. In another embodiment, R$_2$ is halogen and R$_1$ and R$_3$ are H. In another embodiment R$_3$ is halogen and R$_1$ and R$_2$ are H.

Where one or more of R$_1$, R$_2$ and R$_3$ is halogen, these may independently be selected from —F, —Cl and —Br. In one embodiment these are selected from —F and —Cl.

In one embodiment R$_1$ or R$_3$ is —Cl, or R$_2$ is —F.

In one embodiment R$^P$ represents a group having the formula (II):

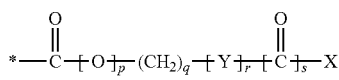
(II)

in which
Y is —O— or NR$^i$ where R$^i$ is either H or C$_{1-3}$ alkyl (e.g. CH$_3$), preferably —O— or NH, e.g. —O—;
X is selected from:
NR$^j$R$^k$ where R$^j$ and R$^k$ are each independently selected from H and C$_{1-6}$ alkyl (preferably C$_{1-3}$ alkyl, e.g. CH$_3$);
—C$_{1-12}$ alkyl (preferably C$_{1-6}$ alkyl) optionally substituted by one or more hydrophilic groups independently selected from: —OR' (wherein R' is either H or C$_{1-3}$ alkyl, e.g. CH$_3$), and —NR"$_2$ (wherein each R" is independently selected from H and C$_{1-3}$ alkyl, e.g. CH$_3$); and
an aryl or heteroaryl group which may optionally be substituted by one or more substituents selected from the group consisting of: halo, hydroxy, C$_{1-6}$ alkyl, C$_{1-6}$ alkoxy, C$_{1-6}$ haloalkyl, C$_{1-6}$ haloalkoxy and C$_{1-6}$ hydroxyalkyl groups; and p, q, r and s are as herein defined.

In one embodiment, Y is —O—.

In one embodiment, X is C$_{1-12}$ alkyl (preferably C$_{1-6}$ alkyl) optionally substituted by one or more groups selected from: —OR' (wherein R' is either H or C$_{1-3}$ alkyl, e.g. CH$_3$), and —NR"$_2$ (wherein each R" is independently selected from H and C$_{1-3}$ alkyl, e.g. CH$_3$).

In one embodiment, R$^P$ is a group of formula (II) in which p is 1, and each of r and s is 0. In this embodiment, R$^P$ is a group of formula (VII):

(VII)

in which *, q and X are as herein defined.

In formula (VII), X may be optionally substituted C$_{1-12}$ alkyl in which the alkyl group may be straight-chained or branched. Short chain alkyl groups may be preferred, such as optionally substituted C$_{1-6}$ alkyl, e.g. C$_{1-4}$ alkyl. In one embodiment, X is unsubstituted alkyl. In one embodiment, q is 0 or 1.

Non-limiting examples of groups of formula (VII) include the following (in which * denotes the point of attachment of the group to the remainder of the molecule):

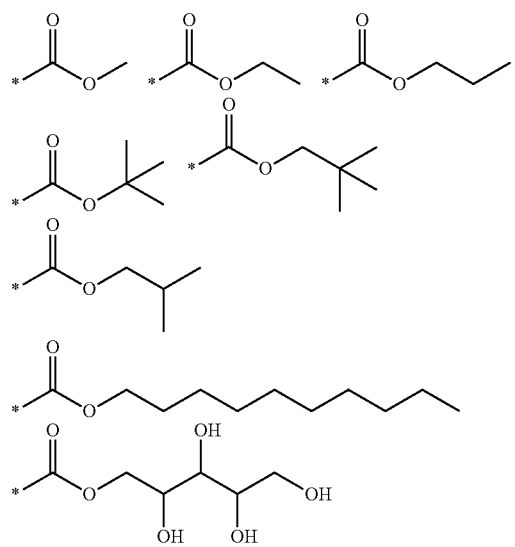

In one embodiment, R$^P$ is a group of formula (II) in which each of p, r and s is 0. In this embodiment, R$^P$ is a group of formula (VIII):

(VIII)

in which *, q and X are as herein defined.

In formula (VIII), X may be optionally substituted C$_{1-12}$ alkyl in which the alkyl group may be straight-chained or branched. Short chain alkyl groups may be preferred, such as optionally substituted C$_{1-6}$ alkyl, e.g. C$_{1-4}$ alkyl. In one embodiment, X is unsubstituted alkyl. In one embodiment, q is 0 or 1.

In formula (VIII), X may be an optionally substituted aryl or heteroaryl group, e.g. an unsubstituted heteroaryl group. In one embodiment, q is 0 or 1, preferably 0.

Non-limiting examples of groups of formula (VIII) include the following (in which * denotes the point of attachment of the group to the remainder of the molecule):

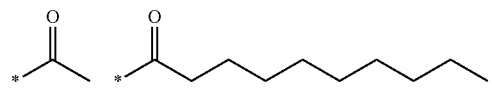

-continued

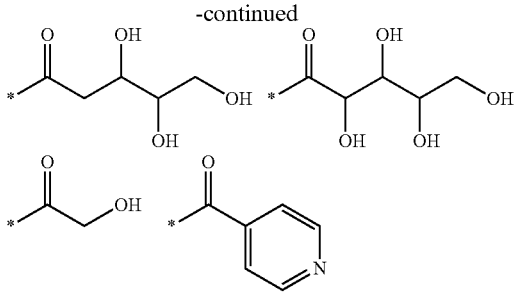

In one embodiment, $R^P$ is a group of formula (II) in which Y is —O—, each of p and r is 1 and s is 0. In this embodiment, $R^P$ is a group of formula (IX):

*—CO—O—(CH$_2$)$_q$—O—X    (IX)

in which *, q and X are as herein defined.

In formula (IX), X may be optionally substituted $C_{1-12}$ alkyl in which the alkyl group may be straight-chained or branched. Short chain alkyl groups may be preferred, such as optionally substituted $C_{1-6}$ alkyl, e.g. $C_{1-4}$ alkyl. In one embodiment, X is unsubstituted alkyl. In one embodiment, q is 0 or 1. Preferably q is 1.

Non-limiting examples of groups of formula (IX) include the following (in which * denotes the point of attachment of the group to the remainder of the molecule):

In one embodiment, $R^P$ is a group of formula (II) in which Y is —O—, each of p and s is 0 and r is 1. In this embodiment, $R^P$ is a group of formula (X):

*—CO—(CH$_2$)$_q$—O—X    (X)

in which *, q and X are as herein defined.

In formula (X), X may be optionally substituted $C_{1-12}$ alkyl in which the alkyl group may be straight-chained or branched. Short chain alkyl groups may be preferred, such as optionally substituted $C_{1-6}$ alkyl, e.g. $C_{1-4}$ alkyl. In one embodiment, X is unsubstituted alkyl. In one embodiment, q is 0 or 1.

Non-limiting examples of groups of formula (X) include the following (in which * denotes the point of attachment of the group to the remainder of the molecule):

In one embodiment, $R^P$ is a group of formula (II) in which Y is —O—, p is 0 and each of r and s is 1. In this embodiment, $R^P$ is a group of formula (XI):

*—CO—(CH$_2$)$_q$—O—CO—X    (XI)

in which *, q and X are as herein defined.

In formula (XI), X may be optionally substituted $C_{1-12}$ alkyl in which the alkyl group may be straight-chained or branched. Short chain alkyl groups may be preferred, such as optionally substituted $C_{1-6}$ alkyl, e.g. $C_{1-4}$ alkyl. In one embodiment, X is unsubstituted alkyl. In one embodiment, q is 0 or 1.

Non-limiting examples of groups of formula (XI) include the following (in which * denotes the point of attachment of the group to the remainder of the molecule):

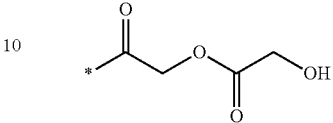

Examples of compounds in accordance with the invention include, but are not limited to, the following:

6-[6-(cyclopentylmethoxy)pyridin-2-yl]-3-[(2,4-dichlorophenyl)sulfanyl]-6-(thiophen-3-yl)piperidine-2,4-dione;
6-(6-bromopyridin-2-yl)-3-[(2-chloro-4-fluorophenyl)sulfanyl]-6-(thiophen-3-yl)piperidine-2,4-dione;
3-[(2-chloro-4-fluorophenyl)sulfanyl]-6-[6-(cyclopentylmethoxy)pyridin-2-yl]-6-(thiophen-3-yl)piperidine-2,4-dione;
3-((2-chloro-4-fluorophenyl)thio)-6-(6-ethoxypyridin-2-yl)-6-(thiophen-3-yl)piperidine-2,4-dione;
6-[6-(cyclopentylmethoxy)pyridin-2-yl]-3-[(2,5-dichlorophenyl)sulfanyl]-6-(thiophen-3-yl)piperidine-2,4-dione;
6-(6-bromopyridin-2-yl)-3-[(2,3-dichlorophenyl)sulfanyl]-6-(thiophen-3-yl)piperidine-2,4-dione;
6-[6-(cyclopentylmethoxy)pyridin-2-yl]-3-[(2,3-dichlorophenyl)sulfanyl]-6-(thiophen-3-yl)piperidine-2,4-dione;
3-((2-chloro-4-fluorophenyl)thio)-6-(4-morpholinophenyl)-6-(thiophen-3-yl)piperidine-2,4-dione;
3-((2,3-dichlorophenyl)thio)-6-(4-morpholinophenyl)-6-(thiophen-3-yl)piperidine-2,4-dione;
3-((2,5-dichlorophenyl)thio)-6-(4-morpholinophenyl)-6-(thiophen-3-yl)piperidine-2,4-dione;
3-((2-chlorophenyl)thio)-6-(pyrimidin-5-yl)-6-(thiophen-3-yl)dihydro-2H-pyran-2,4(3H)-dione;
3-((2-chlorophenyl)thio)-6-(pyridin-2-yl)-6-(thiophen-3-yl)dihydro-2H-pyran-2,4(3H)-dione;
3-((2-chlorophenyl)thio)-6-(2-morpholinopyrimidin-5-yl)-6-(thiophen-3-yl)dihydro-2H-pyran-2,4(3H)-dione;
5-[(2-chloro-4-fluorophenyl)sulfanyl]-2-[6-(cyclopentylmethoxy)pyridin-2-yl]-6-oxo-2-(thiophen-3-yl)-1,2,3,6-tetrahydropyridin-4-yl ethyl carbonate;
6'-(cyclopentylmethoxy)-5-((2,3-dichlorophenyl)thio)-6-oxo-2-(thiophen-3-yl)-1,2,3,6-tetrahydro-[2,2'-bipyridin]-4-yl methyl carbonate;
5-((2-chloro-4-fluorophenyl)thio)-6'-(cyclopentylmethoxy)-6-oxo-2-(thiophen-3-yl)-1,2,3,6-tetrahydro-[2,2'-bipyridin]-4-yl acetate;
5-((2-chloro-4-fluorophenyl)thio)-2-(4-morpholinophenyl)-6-oxo-2-(thiophen-3-yl)-1,2,3,6-tetrahydropyridin-4-yl propyl carbonate;
5-((2,3-dichlorophenyl)thio)-2-(4-morpholinophenyl)-6-oxo-2-(thiophen-3-yl)-1,2,3,6-tetrahydropyridin-4-yl ethyl carbonate;
6'-(cyclopentylmethoxy)-5-((2,5-dichlorophenyl)thio)-6-oxo-2-(thiophen-3-yl)-1,2,3,6-tetrahydro-[2,2'-bipyridin]-4-yl decyl carbonate;
5-((2,5-dichlorophenyl)thio)-2-(4-morpholinophenyl)-6-oxo-2-(thiophen-3-yl)-1,2,3,6-tetrahydropyridin-4-yl (2-methoxyethyl) carbonate;
2-(5-bromopyridin-2-yl)-5-((2-chlorophenyl)thio)-6-oxo-2-(thiophen-3-yl)-3,6-dihydro-2H-pyran-4-yl methyl carbonate;

6'-(cyclopentylmethoxy)-5-((2,4-dichlorophenyl)thio)-6-oxo-2-(thiophen-3-yl)-1,2,3,6-tetrahydro-[2,2'-bipyridin]-4-yl (2-methoxyethyl) carbonate;

6-(5-bromopyridin-2-yl)-3-((2-chlorophenyl)thio)-6-(thiophen-3-yl)dihydro-2H-pyran-2,4(3H)-dione;

3-((2,4-dichlorophenyl)thio)-6-(4-morpholinophenyl)-6-(thiophen-3-yl)piperidine-2,4-dione;

5-((2,4-dichlorophenyl)thio)-2-(4-morpholinophenyl)-6-oxo-2-(thiophen-3-yl)-1,2,3,6-tetrahydropyridin-4-yl (2-methoxyethyl) carbonate;

6'-(cyclopentylmethoxy)-5-((2,5-dichlorophenyl)thio)-6-oxo-2-(thiophen-3-yl)-1,2,3,6-tetrahydro-[2,2'-bipyridin]-4-yl (2-methoxyethyl) carbonate;

5-((2,5-dichlorophenyl)thio)-2-(4-morpholinophenyl)-6-oxo-2-(thiophen-3-yl)-1,2,3,6-tetrahydropyridin-4-yl isobutyl carbonate;

5-((2,5-dichlorophenyl)thio)-2-(4-morpholinophenyl)-6-oxo-2-(thiophen-3-yl)-1,2,3,6-tetrahydropyridin-4-yl acetate;

5-((2,5-dichlorophenyl)thio)-2-(4-morpholinophenyl)-6-oxo-2-(thiophen-3-yl)-1,2,3,6-tetrahydropyridin-4-yl pivalate;

5-((2-chloro-4-fluorophenyl)thio)-2-(4-morpholinophenyl)-6-oxo-2-(thiophen-3-yl)-1,2,3,6-tetrahydropyridin-4-yl iso-butyl carbonate;

5-((2,5-dichlorophenyl)thio)-2-(4-morpholinophenyl)-6-oxo-2-(thiophen-3-yl)-1,2,3,6-tetrahydropyridin-4-yl isonicotinate;

5-((2-chloro-4-fluorophenyl)thio)-2-(4-morpholinophenyl)-6-oxo-2-(thiophen-3-yl)-1,2,3,6-tetrahydropyridin-4-yl (2-methoxyethyl) carbonate;

5-((2-chlorophenyl)thio)-2-(2-morpholinopyrimidin-5-yl)-6-oxo-2-(thiophen-3-yl)-3,6-dihydro-2H-pyran-4-yl (2-methoxyethyl) carbonate;

6'-(cyclopentylmethoxy)-5-((2,5-dichlorophenyl)thio)-6-oxo-2-(thiophen-3-yl)-1,2,3,6-tetrahydro-[2,2'-bipyridin]-4-yl (2-methoxyethyl) carbonate;

and their stereoisomers, tautomers, pharmaceutically acceptable salts, and prodrugs thereof.

The compounds according to the invention may be converted into a salt thereof, particularly into a pharmaceutically acceptable salt thereof with an inorganic or organic acid or base. Acids which may be used for this purpose include hydrochloric acid, hydrobromic acid, sulfuric acid, sulfonic acid, methanesulfonic acid, phosphoric acid, fumaric acid, succinic acid, lactic acid, citric acid, tartaric acid, maleic acid, acetic acid, trifluoroacetic acid and ascorbic acid. Bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

In one embodiment, the compounds of the invention may be provided in the form of their corresponding enol derivatives. These include compounds represented by formula (Ib), their stereoisomers, pharmaceutically acceptable salts and prodrugs:

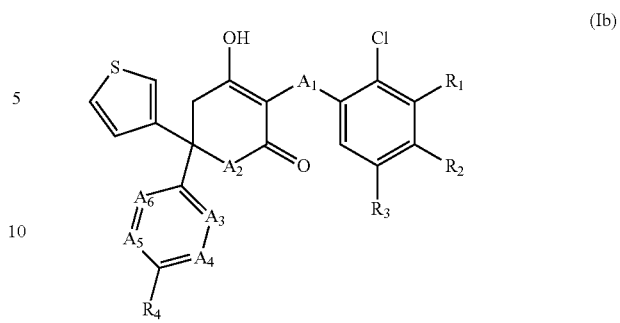

(Ib)

wherein $A_1$ to $A_6$ and $R_1$ to $R_4$ are as defined herein. Any of these groups may be defined in accordance with any of the embodiments herein described with respect to the compounds of formula (I).

In one embodiment, the compounds of the invention are those of formula (Ic), their stereoisomers, pharmaceutically acceptable salts and prodrugs:

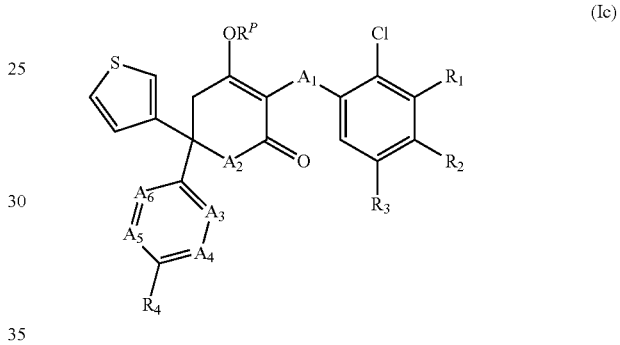

(Ic)

wherein $A_1$ to $A_6$, $R_1$ to $R_4$ are as herein defined, and $R^P$ is a group of formula (II) as defined herein.

Any of $A_1$ to $A_6$, $R_1$ to $R_4$ and $R^P$ in formula (Ic) may be defined in accordance with any of the embodiments herein described with respect to the compounds of formula (I).

As will be understood, the compounds described herein may exist in various stereoisomeric forms, including enantiomers, diastereomers, and mixtures thereof.

The invention encompasses all optical isomers of the compounds described herein and mixtures of optical isomers. Hence, compounds that exist as diastereomers, racemates and/or enantiomers are within the scope of the invention.

In one embodiment, the invention provides compounds having the following stereochemistry, their tautomers, pharmaceutically acceptable salts, and prodrugs:

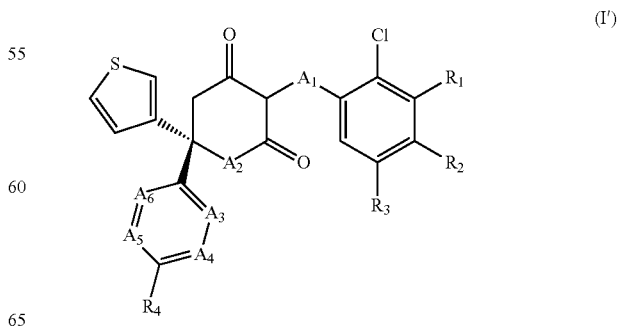

(I')

wherein $A_1$ to $A_6$ and $R_1$ to $R_4$ are as herein defined.

In another embodiment, the invention provides compounds having the following stereochemistry, their tautomers, pharmaceutically acceptable salts, and prodrugs:

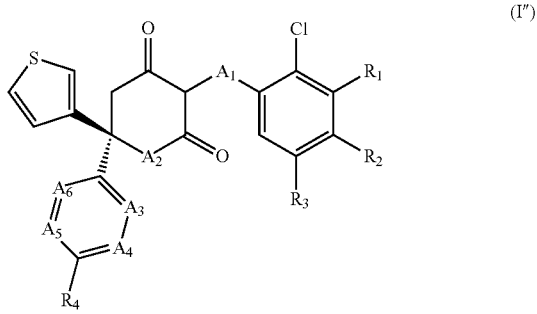

(I″)

wherein $A_1$ to $A_6$ and $R_1$ to $R_4$ are as herein defined.

Any of compounds (Ia), (III), (IIIa), (IV), (IVa), (V), (Va), (VI) and (VIa) having this stereochemistry and, where appropriate, any tautomer, pharmaceutically acceptable salt, or prodrug thereof form further embodiments of the invention.

Any of the compounds of the invention may alternatively be provided in the form of a prodrug. Prodrugs may be obtained by masking one or more functional groups in the parent molecule using a progroup as herein defined. A wide variety of progroups suitable for masking functional groups in active compounds to provide prodrugs are well known in the art. For example, a hydroxy functional group may be masked as an ester, a phosphate ester, or a sulfonate ester which may be hydrolyzed in vivo to provide the parent hydroxy group. An amide functional group may be hydrolyzed in vivo to provide the parent amino group. A carboxyl group may be masked as an ester or amide which may be hydrolyzed in vivo to provide the parent carboxyl group. Other examples of suitable progroups will be apparent to those of skill in the art.

In one embodiment, the compounds of the invention have a hydroxy functional group that can be derivatized to produce suitable prodrugs. For example, the hydroxy group can be converted to an alkyl or aryl ester, a phosphate ester, a sulfonate ester, etc.

Suitable progroups include those which together with the —O— atom to which they are linked form an alkyl ester, phosphate ester, sulfonate ester, carbonate, or carbamate group. The precise nature of the progroup may be selected according to need, for example depending on the desired oil or water solubility of the prodrug, its intended mode of administration and/or its intended mode of metabolism at the target site to produce the active drug compound. The progroup may, for example, be hydrophilic or lipophilic in order to increase or decrease water solubility as required. The choice of progroup may also impart other desirable properties such as enhanced absorption from the gastrointestinal tract, improved drug stability, etc.

The compounds according to the invention may be prepared from readily available starting materials using synthetic methods known in the art, for example, using methods analogous to those described in WO 2015/140133, the entire content of which is incorporated herein by reference.

The following schemes show general methods for preparing the compounds of the invention and key intermediates. Such methods form a further aspect of the invention. The compounds used as starting materials are either known from the literature or may be commercially available. Alternatively, these may readily be obtained by methods known from the literature. As will be understood, other synthetic routes may be used to prepare the compounds using different starting materials, different reagents and/or different reaction conditions. A more detailed description of how to prepare the compounds in accordance with the invention is found in the Examples.

Scheme 1

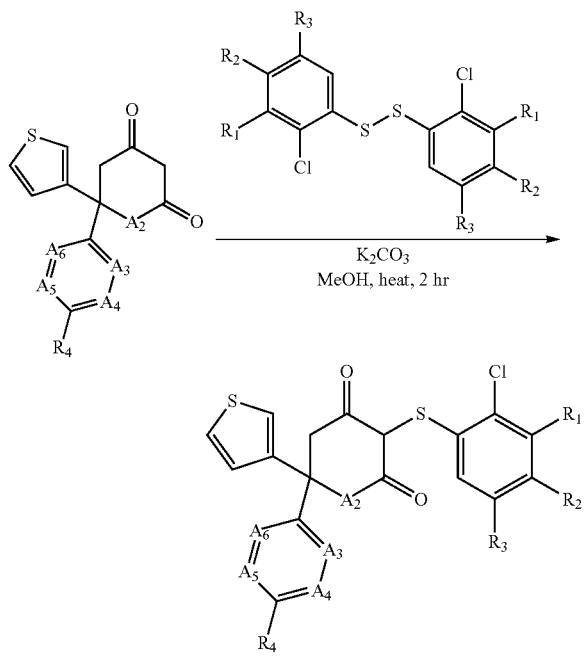

In scheme 1, $A_2$ is NR (wherein R is H or $C_{1-3}$ alkyl), and $A_3$ to $A_6$, $R_1$ to $R_4$ are as herein defined.

Scheme 2

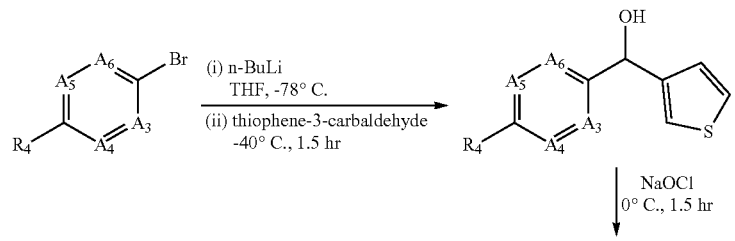

(i) n-BuLi
THF, -78° C.
(ii) thiophene-3-carbaldehyde
-40° C., 1.5 hr

NaOCl
0° C., 1.5 hr

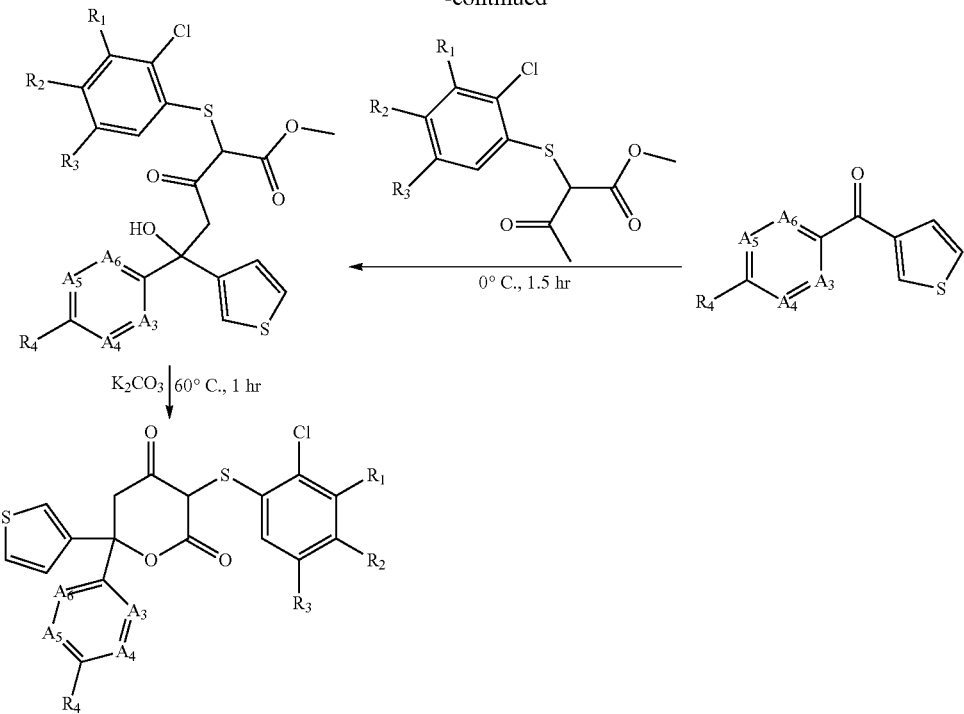
In scheme 2, $A_3$ to $A_6$, and $R_1$ to $R_4$ are as herein defined.
Scheme 3
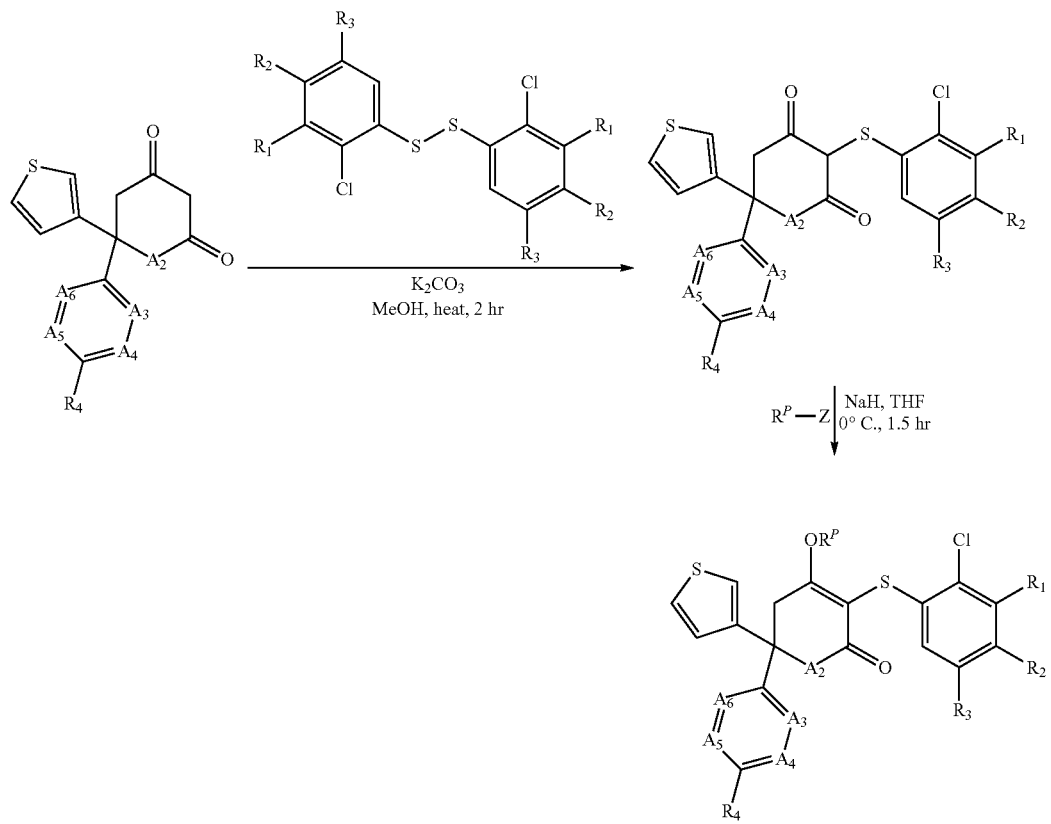

In scheme 3, $A_2$ to $A_6$, $R_1$ to $R_4$ and $R^P$ are as herein defined, and Z is a leaving group such as a halogen atom, e.g. Cl.

The compounds according to the invention have valuable pharmacological properties, particularly an inhibitory effect on LDHA. In view of their ability to inhibit LDHA, the compounds according to the invention are suitable for the treatment and/or prevention of any condition or disease which is mediated by the activation of LDHA.

LDHA plays a central role in the pathology of a variety of cancers. The compounds of the invention are thus particularly suitable for preventing and/or treating malignant and pre-malignant cancer conditions in which LDHA is upregulated, such as cancerous growths or tumors, and their metastases; tumors such as sarcomas and carcinomas, in particular solid tumors.

More specifically, the compounds are effective in treatment and/or prevention of the following cancers: sarcomas, including osteogenic and soft tissue sarcomas; carcinomas, e.g. breast, lung, cerebral, bladder, thyroid, prostate, colon, rectum, pancreas, stomach, liver, uterine, hepatic, renal, prostate, cervical and ovarian carcinomas; lymphomas, including Hodgkin and non-Hodgkin lymphomas; neuroblastoma, melanoma, myeloma, Wilm's tumor; leukemias, including acute lymphoblastic leukemia and acute myeloblastic leukemia; astrocytomas, gliomas and retinoblastomas.

Examples of cancers which may be treated in accordance with the invention include colon cancers (such as colorectal cancer), pancreatic cancer (e.g. pancreas adenocarcinoma), gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian cancers (e.g. ovarian endometrial cancer), bladder cancer, thyroid cancers (e.g. anaplastic thyroid cancer), head and neck cancer, breast cancer, prostate cancer and glioblastoma.

Particularly preferably, the compounds herein described may be used in the treatment and/or prevention of breast cancer, non-small cell lung cancer, ovarian, thyroid, colorectal, pancreatic and prostate cancers and glioblastoma. Treatment of pancreatic cancer and breast cancer are a preferred aspect of the invention.

Viewed from a further aspect the invention thus provides a compound as herein described for use in therapy. Unless otherwise specified, the term "therapy" as used herein is intended to include both treatment and prevention.

In a further aspect the invention provides a compound as herein described for use in the treatment or prevention of any of the conditions herein described, for example in the treatment or prevention of colon cancers (such as colorectal cancer), pancreatic cancer, gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian endometrial cancer, bladder cancer, anaplastic thyroid cancer, head and neck cancer, breast cancer, prostate cancer or glioblastoma.

In another aspect the invention provides the use of a compound as herein described in the manufacture of a medicament for use in a method of treatment or prevention of any of the conditions herein described.

Also provided is a method of treatment of a human or non-human animal body to combat or prevent any of the conditions herein described, for example to combat or prevent colon cancers (such as colorectal cancer), pancreatic cancer, gastric cancer, liver cancers (e.g. hepatocellular and hepatoblastoma carcinomas), Wilms tumor of the kidney, medulloblastoma, skin cancers (e.g. melanoma), non-small cell lung cancer, cervical cancer, ovarian endometrial cancer, bladder cancer, anaplastic thyroid cancer, head and neck cancer, breast cancer, prostate cancer or glioblastoma, said method comprising the step of administering to said body an effective amount of a compound as herein described.

The compounds herein described also find use in the treatment or prevention of other conditions associated with hyperproliferation of cells and other metabolic diseases, such as epilepsy.

The brain needs a lot of energy to function and its high energy demands are met from its main energy source, glucose, which is supplied by the blood stream. However, the brain can also use other energy substrates such as ketone bodies and lactate. Ketones are consumed during extended periods of starvation while lactate is consumed during rigorous physical activity such as exercise. Ketogenic diets which are high in fats and low in carbohydrates have been used since the 1920's as a way for epileptic patients with drug-resistance epilepsy to control and thus reduce their seizures (Geyelin, Med. Rec. 99: 1037-1039, 1921; Peterman, Am. J. Dis. Child. 28: 28-33, 1924; and Neal et al., lancet Neurol. Vol. 7 (6): 500-506, 2008). This suggests that epilepsy is a metabolic disease which could benefit from LDHA inhibitors as a therapy.

Astrocytes, star-shaped glia cells in the brain, use glucose and convert it to lactate which is then converted to pyruvate in neurons—this is called the astrocyte-neuron lactate shuttle. Lactate is highly consumed by neurons as an energy source during neuronal excitation, when epileptics are having seizures (Gallagher et al., Brain 132: 2839-2849, 2009). Pyruvate, the organic compound produced in neurons has been shown to facilitate epileptic activity by depolarizing nerve cells (Sada et al., Science 347, 6228: 1362-1367, 2015). Pyruvate and lactate can be converted into each other by the enzyme LDH and are thus regulated by it. Oxamate, the salt of the half-amide of oxalic acid, a structural analog of pyruvate and known inhibitor of LDHA was directly injected into the hippocampus of mice with temporal-lobe epilepsy and found to suppress their seizures (Sada et al., above). The inhibition of LDH eliminated the depolarizing effects of lactate and also caused nerve cells to become hyperpolarized, meaning they were less excitable, more stable and thus not as prone to epileptic activity. These observations taken together suggest that inhibitors of LDHA mimic the ketogenic diet and could also serve as a possible anti-convulsant drug for epilepsy.

Highly proliferative cells such as cancer cells have high energy demands and need a constant supply of biosynthetic precursors for macromolecules such as DNA, proteins and lipids to build up. To fulfill this demand, glucose uptake is increased—an effect which is similarly observed in immune and inflammatory cells when injury has occurred, during infection or inflammation. During inflammation T-cells become activated and thus switch their metabolism to use the less efficient but more rapid process of aerobic glycolysis, which is independent of mitochondrial function and involves an increased production of lactate (MacIver et al., Annu. Rev. Immunol. 31: 259-283, 2013; Palmer et al., Front. Immunol, 6: 1, 2015). Experiments using mice with autoimmune diseases such as asthma and arthritis have shown that glycolytic inhibitors, such as dichloroacetate, alleviated their inflammation (Bian et al., Arthritis Res. Ther. 11, R132, 2009). There are also naturally occurring compounds that are known to have anti-inflammatory properties, such as cumin and panepoxydone, which have also been shown to inhibit LDHA (Das et al., PLos ONE 9, e99583, 2014; Arora et al., Oncotarget 6: 662-678, 2015).

The LDHA inhibitors herein described are capable of shifting cell metabolism from aerobic glycolysis back to oxidative phosphorylation and are therefore also suitable for use as a therapeutic for inflammatory disorders such as rheumatoid arthritis, multiple sclerosis, and allergic conditions such as asthma, since these conditions are characterized by increased glycolysis and LDH activity.

For use in a therapeutic or prophylactic treatment, the compounds of the invention will typically be formulated as a pharmaceutical formulation. In a further aspect, the invention thus provides a pharmaceutical composition comprising a compound according to the invention, together with one or more pharmaceutically acceptable carriers, excipients or diluents.

Acceptable carriers, excipients and diluents for therapeutic use are well known in the art and can be selected with regard to the intended route of administration and standard pharmaceutical practice. Examples include binders, lubricants, suspending agents, coating agents, solubilizing agents, preserving agents, wetting agents, emulsifiers, surfactants, sweeteners, colorants, flavoring agents, antioxidants, odorants, buffers, stabilizing agents and/or salts.

The compounds of the invention may be formulated with one or more conventional carriers and/or excipients according to techniques well known in the art. Typically, the compositions will be adapted for oral or parenteral administration, for example by intradermal, subcutaneous, intraperitoneal or intravenous injection.

For example, these may be formulated in conventional oral administration forms, e.g. tablets, coated tablets, capsules, powders, granulates, solutions, dispersions, suspensions, syrups, emulsions, etc. using conventional excipients, e.g. solvents, diluents, binders, sweeteners, aromas, pH modifiers, viscosity modifiers, antioxidants, etc. Suitable excipients may include, for example, corn starch, lactose, glucose, microcrystalline cellulose, magnesium stearate, polyvinylpyrrolidone, citric acid, tartaric acid, water, ethanol, glycerol, sorbitol, polyethylene glycol, propylene glycol, cetylstearyl alcohol, carboxymethylcellulose or fatty substances such as saturated fats or suitable mixtures thereof, etc.

Where parenteral administration is employed this may for example be by means of intravenous, subcutaneous or intramuscular injection. For this purpose, sterile solutions containing the active agent may be employed, such as an oil-in-water emulsion. Where water is present, an appropriate buffer system (e.g., sodium phosphate, sodium acetate or sodium borate) may be added to prevent pH drift under storage conditions.

The use of orally administrable compositions, e.g. tablets, coated tablets, capsules, syrups, etc. is especially preferred.

The formulations may be prepared using conventional techniques, such as dissolution and/or mixing procedures.

The dosage required to achieve the desired activity of the compounds herein described will depend on various factors, such as the compound selected, its mode and frequency of administration, whether the treatment is therapeutic or prophylactic, and the nature and severity of the disease or condition, etc. Typically, a physician will determine the actual dosage which will be most suitable for an individual subject.

The specific dose level and frequency of dosage for any particular patient may be varied and will depend upon factors such as the activity of the specific compound employed, the metabolic stability and length of action of that compound, the age of the patient, the mode and time of administration, and the severity of the particular condition. The compound and/or the pharmaceutical composition may be administered in accordance with a regimen from 1 to 10 times per day, such as once or twice per day. For oral and parenteral administration to human patients, the daily dosage level of the agent may be in single or divided doses.

Suitable daily dosages of the compounds herein described are expected to be in the range from 0.1 mg to 1 g of the compound; 1 mg to 500 mg of the compound; 1 mg to 300 mg of the compound; 5 mg to 100 mg of the compound, or 10 mg to 50 mg of the compound. By a "daily dosage" is meant the dosage per 24 hours.

The pharmacological properties of the compounds of the invention can be analyzed using standard assays for functional activity. Detailed protocols for testing of the compounds of the invention are provided in the Examples.

EXAMPLES

The invention will now be described in more detail by way of the following non-limiting Examples and with reference to the accompanying figures, in which.

Figure 11:
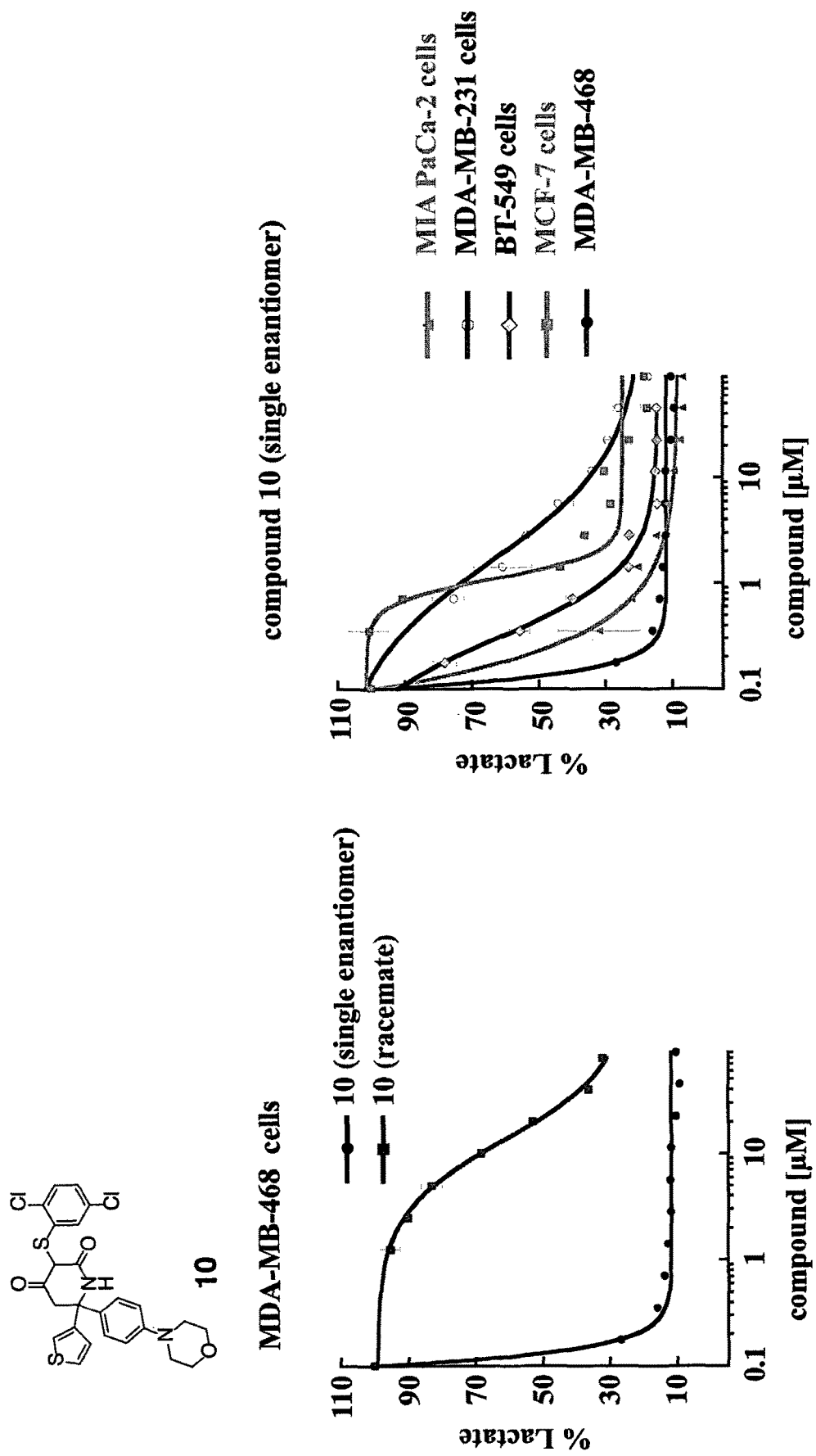
Figure 12:
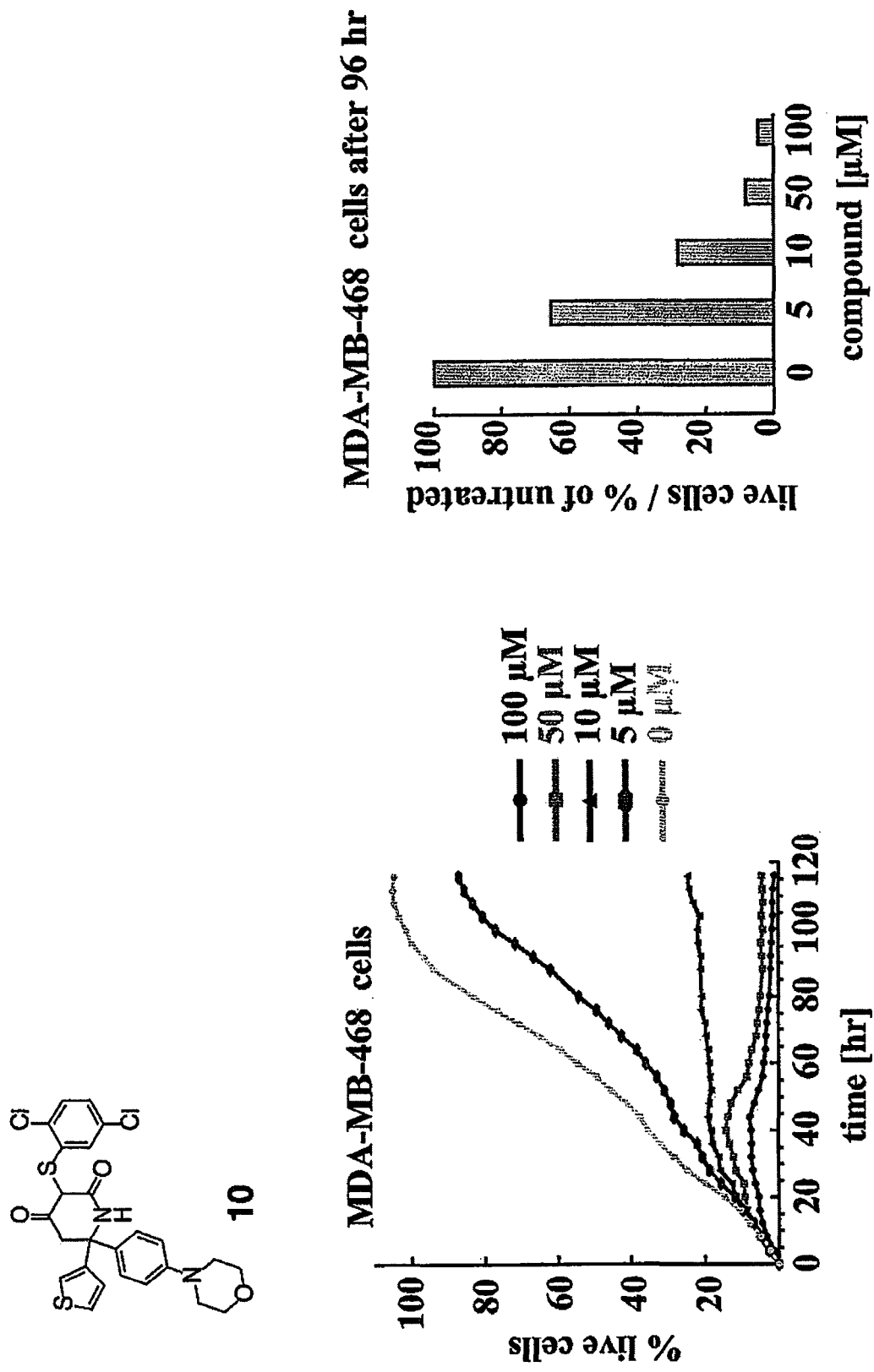

FIG. 11 shows % lactate in MDA-MB-468 cells after incubation with the compound of Example 10 (as a racemic mixture) compared to one of its enantiomers (Enantiomer 1) (left hand figure) and % lactate in MIA PaCa-2 cells, MDA-MB-231 cells, BT-549 cells, MCF-7 cells and MDA- MB-468 cells for the same enantiomer of the compound of Example 10 (right hand figure); and FIG. 12 shows the cell viability rate of MDA-MB-468 cancer cells after incubation with the indicated concentrations of compound Example 10 during a 120 hour time course with 3 hour intervals (left hand figure) and live cells per % of untreated MDA-MB-468 cancer cells after 96 hour incubation for different compound concentrations of compound of Example 10 (right hand figure).

The chemical reactions described in the Examples may readily be adapted to prepare other LDHA inhibitors in accordance with the invention, for example by using other reagents known in the art, by modifying the reaction conditions, and/or by choosing any suitable protecting groups, etc.

All reagents and solvents commercially available were used without further purifications. NMR ($^1$H, $^{13}$C) spectra were recorded on a Bruker AVII-400 MHz, AVIII-400 MHz or a DPX-300 MHz spectrometer. Coupling constants (J) are reported in Hertz (Hz), and chemical shifts are reported in parts per million (ppm) relative to CDCl$_3$ (7.26 ppm for $^1$H and 77.16 ppm for $^{13}$C), methanol-d4 (3.31 ppm for $^1$H and 49.15 ppm for $^{13}$C) and DMSO-d6 (2.50 ppm for $^1$H and 39.52 ppm for $^{13}$C). All yields are uncorrected.

Abbreviations

DCM: dichloromethane; hr: hour; MeOH: methanol; THF: tetrahydrofuran; e.e.: enantiomeric excess; R$_t$: retention time.

Preparation of Starting Materials:

All piperidine-dione starting materials were prepared using the procedure described in WO 2015/140133, or suitably modified versions thereof.

A. Preparation of 6-(6-bromopyridin-2-yl)-6-(thiophen-3-yl)piperidine-2,4-dione

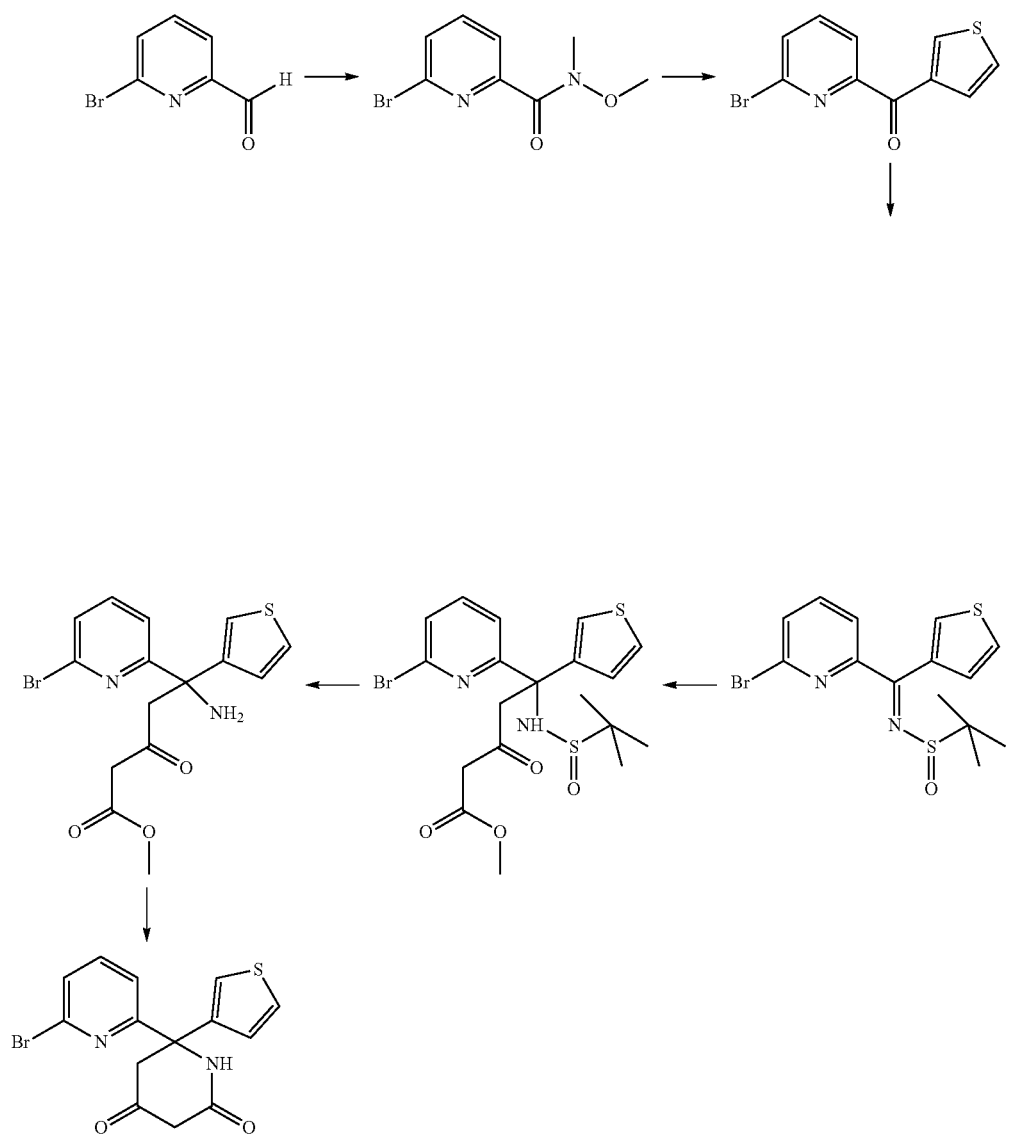

Step A: N,O-dimethylhydroxylamine hydrochloride (14.6 g, 0.15 mol), HATU (57.0 g, 0.15 mol) and diisopropylethylamine (47.8 g, 0.37 mol) were added to a slurry of 6-bromopicolinic acid (25.3 g, 0.125 mol) in DCM (370 mL). The mixture was stirred at room temperature for 3 hr. The reaction mixture was washed with aqueous HCl 1M (2×200 mL) and filtered to remove any white solid. After concentration under reduced pressure, the crude product was purified by Kugelrohr distillation and silica gel chromatography (hexanes/ethyl acetate: 10 to 25%) to give 6-bromo-N-methoxy-N-methylpicolinamide in 74% yield.

Step B: n-Butyllithium (48 mL, 0.12 mol) was slowly added to a solution of 3-bromothiophene (19.6 g, 0.12 mol) in di-isopropyl ether (280 mL) at −78° C. After stirring at −78° C. for 30 min, 6-bromo-N-methoxy-N-methylpicolinamide (22.5 g, 92 mmol) in di-isopropylether (30 mL) was slowly added and the mixture was stirred at −78° C. for 2 hr. The reaction mixture was quenched with aqueous saturated NH$_4$Cl (85 mL), then warmed to ambient temperature. The solution was diluted with ethyl acetate (110 mL), washed with water (3×100 mL) and brine (50 mL), dried over Na$_2$SO$_4$ and concentrated under reduced pressure to give (6-bromopyridin-2-yl)(thiophen-3-yl)methanone in 56% yield.

Step C: (6-Bromopyridin-2-yl)(thiophen-3-yl)methanone (13.8 g, 51.5 mmol) and titanium ethoxide (31.4 mL, 150 mmol) were added to a solution of 2-methylpropane-2-sulfinamide (12.2 g, 100 mmol) in THF (200 mL). The mixture was stirred under reflux for 20 hr. The solution was allowed to cool to ambient temperature and poured into ice water, filtered, and washed with ethyl acetate (5×100 mL). The filtrate was extracted with ethyl acetate (2×50 mL), and the combined organic phases washed with brine (50 mL), dried over Na$_2$SO$_4$ and concentrated under reduced pressure. The crude product was purified by flash chromatography (SiO$_2$, hexanes/ethyl acetate: 10 to 25%) to give N-((6-bromopyridin-2-yl)(thiophen-3-yl)methylene)-2-methylpropane-2-sulfinamide in 88% yield.

Step D: Methyl 3-oxobutanoate (10.5 g, 90 mmol) in THF (20 mL) was added to a suspension of NaH (3.6 g, 90 mmol) in THF (200 mL) at 0° C. n-Butyllithium (36 mL, 90 mmol) was slowly added to the mixture and the reaction was stirred at 0° C. for 30 min. N-((6-bromopyridin-2-yl)(thiophen-3-yl)methylene)-2-methylpropane-2-sulfinamide (16.4 g, 45 mmol) in THF (50 mL) was added to the mixture and stirred at 0° C. for another 2 hr. The mixture was allowed to warm to room temperature overnight and cooled to 0° C. The reaction was quenched with saturated NH$_4$Cl (100 mL) and diluted with ethyl acetate (85 mL). The organic phase was washed with water (2×100 mL), dried over anhydrous Na$_2$SO$_4$, filtered and concentrated to give methyl 5-(6-bromopyridin-2-yl)-5-((tert-butylsulfinyl)amino)-3-oxo-5-(thiophen-3-yl)pentanoate.

Step E: TMSCl (19.1 g, 0.18 mol) was slowly added to methanol (100 mL) and the mixture was added to a solution of methyl 5-(6-bromopyridin-2-yl)-5-((tert-butylsulfinyl) amino)-3-oxo-5-(thiophen-3-yl)pentanoate (45 mmol) in MeOH (200 mL) at 0° C. The mixture was stirred at room temperature for 1 hr, then cooled to 0° C. and slowly adjusted to pH 7 using aqueous NaOH 2M (80 mL). The solvent was removed under reduced pressure. The crude product was extracted with ethyl acetate (2×100 mL), and the combined organic phases washed with brine (50 mL), dried over Na$_2$SO$_4$, filtered and concentrated to give methyl 5-amino-5-(6-bromopyridin-2-yl)-3-oxo-5-(thiophen-3-yl) pentanoate.

Step F: Potassium carbonate (20.7 g, 150 mmol) was added to a solution of methyl 5-amino-5-(6-bromopyridin-2-yl)-3-oxo-5-(thiophen-3-yl)pentanoate (45 mmol) in MeOH (150 mL). The mixture was stirred under reflux for 2 hr and overnight at room temperature. Methanol was removed under reduced pressure, the crude product was dissolved in water (100 mL), and washed with ethyl acetate (2×40 mL). The aqueous layer was acidified to pH 4 using aqueous HCl 3N (95 mL). The aqueous phase was extracted with ethyl acetate (5×40 mL). The combined organic phases were dried over anhydrous MgSO$_4$, filtered and concentrated to give 6-(6-bromo-2-pyridinyl)-6-(3-thienyl)piperidine-2,4-dione in 41% yield over 3 steps.

B. Preparation of Disulfides

Method A: The phenyl sulfide (6.2 mmol, 1 eq) was dissolved in DCM (1 mL). CF$_3$CH$_2$OH (3 mL) and H$_2$O$_2$ solution (0.66 mL, 6.8 mmol, 1.1 eq) was added. The reaction mixture was stirred at room temperature overnight under vigorous stirring. The white precipitate was filtered and dried under reduced pressure to deliver the desired disulfide.

Method B: The phenyl sulfide (10 mmol, 1 eq) was dissolved in CHCl$_3$ (50 mL) and 1,3-dibromo-5,5-dimethylhydantoin (1.43 g, 5 mmol, 0.5 eq.) was added. After 1 hr at room temperature, a saturated aqueous solution of sodium thiosulfate was added (10 mL). The phases were separated and the aqueous phase was extracted with DCM (2×20 mL). The combined organic phases were dried with Na$_2$SO$_4$, filtered and concentrated under reduced pressure. The crude product was purified by flash chromatography on silica gel (heptane/ethyl acetate: 95/5) to deliver the desired disulfide.

Preparation of 1,2-bis(2-chlorophenyl)disulfane

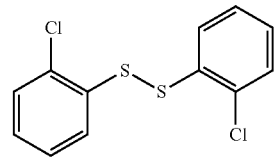 [SMILES: Clc1ccccc1SSc1ccccc1Cl]

Method A: Yield=91%. $^1$H NMR (400 MHz): δ=7.57 (dd, J=8.0, 1.6 Hz, 1H), 7.37 (dd, J=8.0, 1.6 Hz, 1H), 7.22 (td, J=8.0, 1.6 Hz, 1H), 7.16 (td, J=8.0, 1.6 Hz, 1H).

Preparation of 1,2-bis(2,5-dichlorophenyl)disulfane

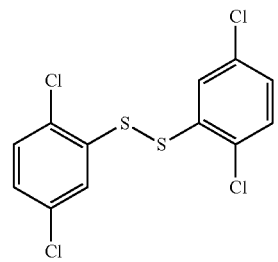 [SMILES: Clc1ccc(Cl)c(SSc2cc(Cl)ccc2Cl)c1]

Method B: Yield=72%. $^1$H NMR: δ=7.52 (d, J=2.0 Hz, 1H), 7.30 (d, J=8.4 Hz, 1H), 7.15 (dd, J=8.4, 2.0 Hz, 1H).

Preparation of 1,2-bis(2-chloro-4-fluorophenyl)disulfane

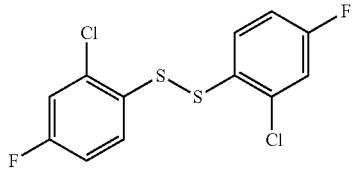 [SMILES: Fc1ccc(SSc2ccc(F)cc2Cl)c(Cl)c1]

Method A: Yield=70%. ¹H NMR: δ=7.53 (dd, J=11.6, 7.6 Hz, 1H), 7.15 (dd, J=10.8, 7.6 Hz, 1H), 6.97 (ddd, J=11.6, 10.8, 3.6 Hz, 1H).

Preparation of 1,2-bis(2,4-dichlorophenyl)disulfane

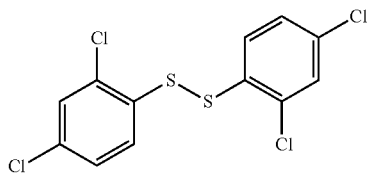 [SMILES: Clc1ccc(SSc2ccc(Cl)cc2Cl)c(Cl)c1]

Method A: Yield=92%. ¹H NMR: δ=7.46 (d, J=11.2 Hz, 1H), 7.39 (d, J=2.8 Hz, 1H), 7.21 (dd, J=11.2, 2.8 Hz, 1H).

Preparation of 1,2-bis(2,3-dichlorophenyl)disulfane

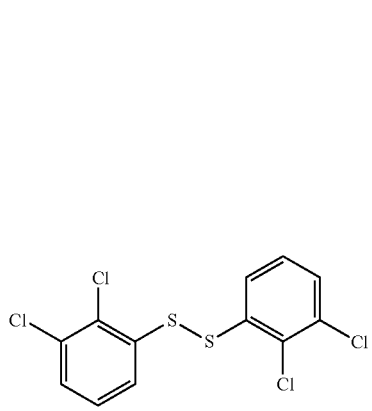 [SMILES: Clc1cccc(SSc2cccc(Cl)c2Cl)c1Cl]

Method B: Yield=73%. ¹H NMR (300 MHz): δ=7.42 (dd, J=10.8, 2.0 Hz, 1H), 7.33 (dd, J=10.8, 2.0 Hz, 1H), 7.16 (t, J=10.8 Hz, H).

C. Preparation of 6-(4-morpholinophenyl)-6-(thiophen-3-yl)piperidine-2,4-dione

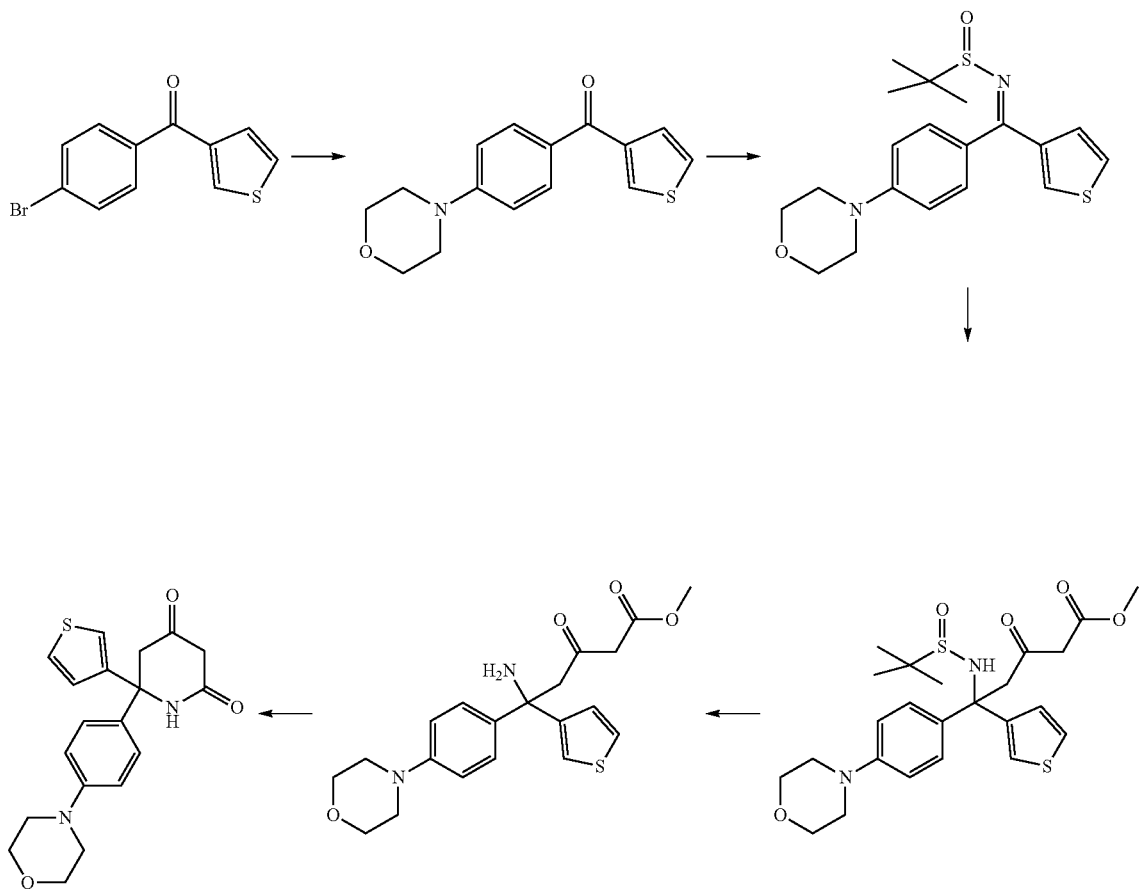

(4-Bromophenyl)(thiophen-3-yl)methanone was prepared according to the procedure described in WO 2015/140133.

Step A: A solution of (4-bromophenyl)(thiophen-3-yl)methanone (3.00 g, 11.2 mmol, 1 eq), morpholine (1.60 mL, 18.0 mmol, 1.5 eq), xantphos (393 mg, 0.68 mmol, 0.06 eq), $Pd_2(dba)_3$ (311 mg, 0.34 mmol, 0.03 eq) and $K_3PO_4$ (4.30 g, 20.0 mmol, 1.8 eq) in toluene (10 mL) was stirred at reflux for 18 hr. The mixture was cooled down, filtered on Celite and concentrated under reduced pressure. The crude material was purified by flash column chromatography ($SiO_2$, heptane/ethyl acetate: 8/2 to 2/1 to 1/1) to give [4-(morpholin-4-yl)phenyl](thiophen-3-yl)methanone (2.90 g, 10.6 mmol) in 95% yield.

Step B: A solution of [4-(morpholin-4-yl)phenyl](thiophen-3-yl)methanone (5.43 g, 19.9 mmol, 1 eq), t-butylsulfinamide (7.26 g, 60.0 mmol, 3 eq) and $Ti(OEt)_4$ (20.9 mL, 100 mmol, 5 eq) in THF (80 mL) was stirred under reflux for 66 hr. The mixture was poured onto ice and washed with ethyl acetate (2×20 mL). The aqueous phase was extracted with ethyl acetate (2×100 mL) and the combined organic phases were dried over $Na_2SO_4$, filtered and concentrated under reduced pressure. The crude material was purified by flash column chromatography ($SiO_2$, heptane/ethyl acetate: 8/2 to 7/3 to 1/1) to give 2-methyl-N-[-[4-(morpholin-4-yl)phenyl](thiophen-3-yl)methylidene]propane-2-sulfinamide (4.74 g, 12.6 mmol) in 63% yield.

Step C: To a suspension of NaH (1.01 g, 25.2 mmol, 2 eq) in THF (50 mL) at 0° C. was added methyl acetoacetate (2.92 g, 25.2 mmol, 2 eq). After 5 min at 0° C., n-Butyllithium (10.1 mL, 25.2 mmol, 2 eq.) was added and the reaction mixture was stirred for 30 min at 0° C. 2-methyl-N-[[4-(morpholin-4-yl)phenyl](thiophen-3-yl)methylidene]propane-2-sulfinamide (4.74 g, 12.6 mmol, 1 eq) in THF (13 mL) was added and stirring continued for 1.5 h at 0° C. TLC showed remaining starting material. Therefore another portion of reagent was prepared with methyl acetoacetate (1.3 mL), NaH (500 mg) and n-Butyllithium (5.0 mL) and added to the reaction mixture. After 1.5 h at 0° C., the reaction was stopped by the addition of saturated aqueous $NH_4Cl$ (20 mL). The phases were separated and the aqueous phase was extracted with ethyl acetate (2×50 mL) and the combined organic phases were washed with brine (40 mL), saturated aqueous $NaHCO_3$ (40 mL) and HCl 1M (40 mL), dried over $Na_2SO_4$, filtered and concentrated under reduced pressure. The crude material was purified by flash column chromatography ($SiO_2$, heptane/ethyl acetate: 3/1 to 2/1 to 1/1 to 1/3 to ethyl acetate) to give methyl 5-((tert-butylsulfinyl)amino)-5-(4-morpholinophenyl)-3-oxo-5-(thiophen-3-yl)pentanoate (3.40 g, 6.90 mmol) in 55% yield.

Step D: To a solution of methyl 5-((tert-butylsulfinyl)amino)-5-(4-morpholinophenyl)-3-oxo-5-(thiophen-3-yl)pentanoate (3.40 g, 6.90 mmol, 1 eq) in methanol (69 mL) was added TMSCl (2.62 mL, 20.7 mmol, 3 eq). The reaction mixture was stirred for 1 hr at room temperature. The reaction was stopped by the addition of aqueous NaOH 2M (11 mL) and the methanol was removed under reduced pressure. The aqueous phase was extracted with ethyl acetate (3×50 mL) and the combined organic phases dried over $Na_2SO_4$, filtered and concentrated under reduced pressure to give the crude product (2.65 g), which was used directly in the next step.

Step E: A solution of methyl 5-amino-5-(4-morpholinophenyl)-3-oxo-5-(thiophen-3-yl)pentanoate (2.65 g, 6.82 mmol, 1 eq) and $K_2CO_3$ (2.83 g, 20.5 mmol, 3 eq) in methanol (34 mL) was stirred at reflux for 2 hr. The mixture was concentrated under reduced pressure and diluted in aqueous HCl 1M (30 mL). The aqueous phase was extracted with ethyl acetate (3×50 mL) and the combined organic phases dried over $Na_2SO_4$, filtered and concentrated under reduced pressure. The crude material was purified by flash column chromatography ($SiO_2$, heptane/ethyl acetate: 4/1 to 2/1 to 1/1 to 1/3 to ethyl acetate to 2% MeOH) to give 6-(4-morpholinophenyl)-6-(thiophen-3-yl)piperidine-2,4-dione (726 mg, 1.87 mmol) in 30% yield over 2 steps.

Preparation of Final Compounds

Example 1—Preparation of 6-[6-(cyclopentylmethoxy)pyridin-2-yl]-3-[(2,4-dichlorophenyl)sulfanyl]-6-(thiophen-3-yl)piperidine-2,4-dione

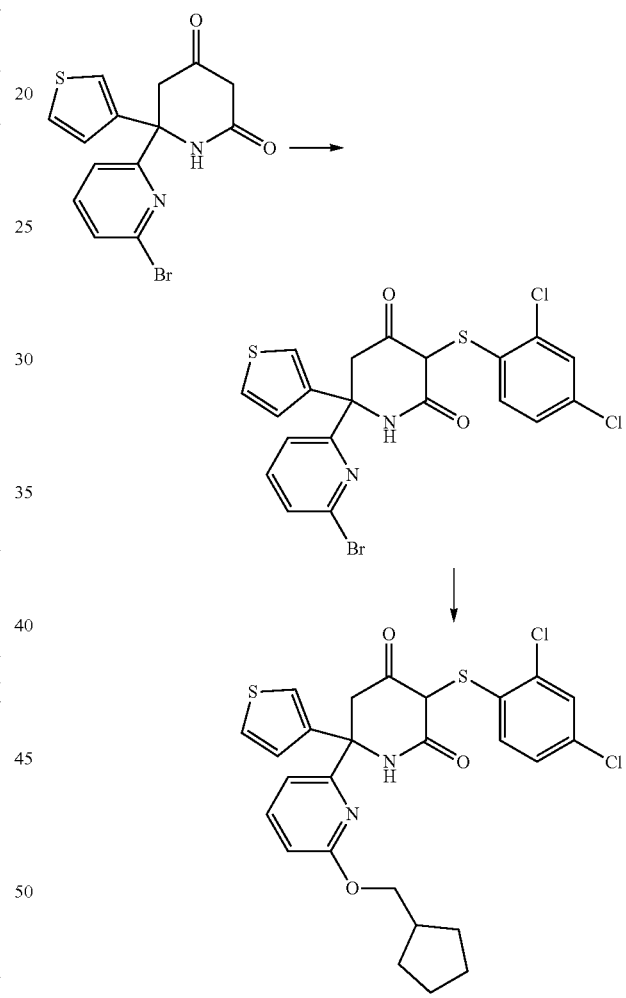

Step A: To a solution of 6-(6-bromopyridin-2-yl)-6-(thiophen-3-yl)piperidine-2,4-dione (500 mg, 1.4 mmol, 1 eq) in MeOH (14 mL) was added 1,2-bis(2,4-dichlorophenyl)disulfane (303 mg, 0.85 mmol, 0.6 eq) and potassium carbonate (593 mg, 4.3 mmol, 3 eq). The reaction was stirred for 2 hr under reflux, and concentrated under reduced pressure. Water (10 mL) and HCl 1M (7 mL) were added and the aqueous phase was extracted with ethyl acetate (3×15 mL). The combined organic phases were dried with $Na_2SO_4$, filtered and concentrated under reduced pressure.

The crude product was purified by flash chromatography on silica gel (eluent: heptane/ethyl acetate: 70/30 to 30/70)

to give 6-(6-bromopyridin-2-yl)-3-[(2,4-dichlorophenyl)sulfanyl]-6-(thiophen-3-yl)piperidine-2,4-dione (487 mg, 0.92 mmol) in 65% yield.

Step B: To a suspension of NaH (76 mg, 1.9 mmol, 5 eq) in THF (4 mL) at 0° C. was added cyclopentanemethanol (204 μL, 1.9 mmol, 5 eq). The reaction was stirred at 0° C. for 30 min and 6-(6-bromopyridin-2-yl)-3-[(2,4-dichlorophenyl)sulfanyl]-6-(thiophen-3-yl)piperidine-2,4-dione (200 mg, 0.38 mmol, 1 eq) was added. The reaction was stirred overnight under reflux and quenched by the addition of water (10 mL) and HCl 1M (5 mL). The aqueous phase was extracted with ethyl acetate (3×15 mL) and the combined organic phases dried with Na$_2$SO$_4$, filtered and concentrated under reduced pressure. The crude product was purified by flash chromatography on silica gel (eluent: heptane/ethyl acetate: 75/25) to give 6-[6-(cyclopentylmethoxy)pyridin-2-yl]-3-[(2,4-dichlorophenyl)sulfanyl]-6-(thiophen-3-yl)piperidine-2,4-dione (115 mg, 0.21 mmol) in 55% yield.

$^1$H NMR (MeOD-d4, 400 MHz): δ=7.75 (t, J=8.0 Hz, 1H), 7.49 (dd, J=9.2, 3.2 Hz, 1H), 7.35 (d, J=2.0 Hz, 1H), 7.32 (dd, J=6.8, 1.2 Hz), 7.19-7.17 (m, 2H), 6.80-6.76 (m, 2H), 5.94 (d, J=8.0 Hz, 1H), 4.29-4.21 (m, 2H), 3.91 (d, J=16.4 Hz, 1H), 3.47 (d, J=16.4 Hz, 1H), 2.35-2.29 (m, 1H), 1.85-1.77 (m, 2H), 1.68-1.54 (m, 4H), 1.41-1.31 (m, 2H).

Example 2—Preparation of 6-(6-bromopyridin-2-yl)-3-[(2-chloro-4-fluorophenyl)sulfanyl]-6-(thiophen-3-yl)piperidine-2,4-dione

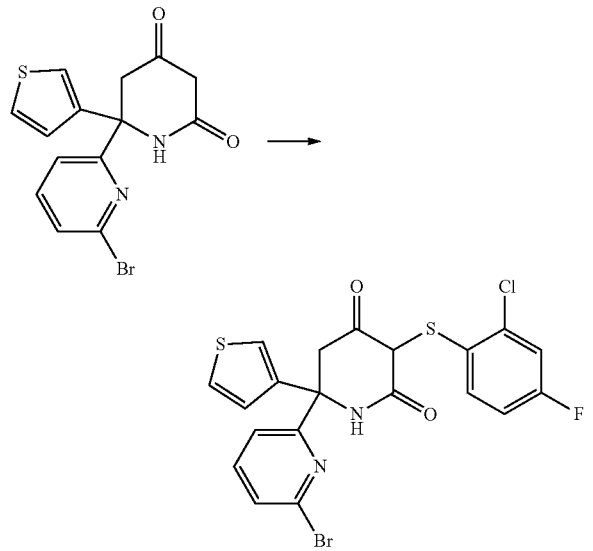

To a solution of 6-(6-bromopyridin-2-yl)-6-(thiophen-3-yl)piperidine-2,4-dione (500 mg, 1.4 mmol, 1 eq) in MeOH (14 mL) was added 1,2-bis(2-chloro-4-fluorophenyl)disulfane (550 mg, 1.7 mmol, 1.2 eq) and potassium carbonate (593 mg, 4.3 mmol, 3 eq). The reaction was stirred for 2 h under reflux, and concentrated under reduced pressure. Water (10 mL) and HCl 1M (7 mL) were added and the aqueous phase was extracted with ethyl acetate (3×15 mL). The combined organic phases were dried with Na$_2$SO$_4$, filtered and concentrated under reduced pressure.

The crude product was purified by flash chromatography on silica gel (eluent: heptane/ethyl acetate: 70/30 to 30/70) to give 6-(6-bromopyridin-2-yl)-3-[(2-chloro-4-fluorophenyl)sulfanyl]-6-(thiophen-3-yl)piperidine-2,4-dione (466 mg, 0.91 mmol) in 64% yield.

$^1$H NMR (DMSO-d6, 400 MHz): δ=11.79 (br s, 1H), 8.58 (s, 1H), 7.88 (t, J=8.0 Hz, 1H), 7.68 (dd, J=8.8, 8.0 Hz, 2H), 7.56 (dd, J=5.2, 3.2 Hz, 1H), 7.36 (dd, J=8.8, 2.8 Hz, 1H), 7.34 (dd, J=2.8, 1.2 Hz, 1H), 7.15 (dd, J=8.8, 1.2 Hz, 1H), 6.72 (td, J=8.8, 2.8 Hz, 1H), 5.95 (dd, J=8.8, 6.0 Hz, 1H), 3.82 (d, J=16.4 Hz, 1H), 3.42 (d, J=16.4 Hz, 1H).

$^{13}$C NMR (DMSO-d6, 100 MHz): δ=166.1, 164.4, 158.9 (d, J=242 Hz), 144.4, 140.7, 140.1, 133.2 (d, J=4 Hz), 129.3 (d, J=10 Hz), 127.0, 127.0, 126.4, 125.8 (d, J=7.7 Hz), 122.2, 120.6, 116.5 (d, J=25 Hz), 114.2 (J=21 Hz), 60.5.

Example 3—Preparation of 3-[(2-chloro-4-fluorophenyl)sulfanyl]-6-[6-(cyclopentylmethoxy)pyridin-2-yl]-6-(thiophen-3-yl)piperidine-2,4-dione

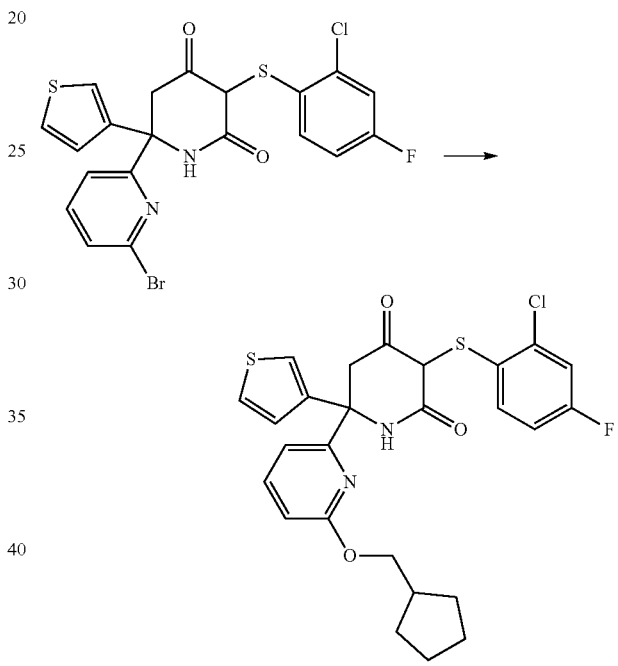

Cyclopentanemethanol (263 μL, 2.5 mmol, 5 eq) was added to a suspension of NaH (98 mg, 2.5 mmol, 5 eq) in THF (5 mL) at 0° C. The reaction was stirred at 0° C. for 30 min and 6-(6-bromopyridin-2-yl)-3-[(2-chloro-4-fluorophenyl)sulfanyl]-6-(thiophen-3-yl)piperidine-2,4-dione (250 mg, 0.49 mmol, 1 eq) was added. The reaction was then stirred overnight under reflux and quenched by the addition of water (10 mL) and HCl 1M (5 mL). The aqueous phase was extracted with ethyl acetate (3×15 mL) and the combined organic phases were dried with Na$_2$SO$_4$, filtered and concentrated under reduced pressure. The crude product was purified by flash chromatography on silica gel (eluent: heptane/ethyl acetate: 75/25) to give 3-[(2-chloro-4-fluorophenyl)sulfanyl]-6-[6-(cyclopentylmethoxy)pyridin-2-yl]-6-(thiophen-3-yl)piperidine-2,4-dione (192 mg, 0.36 mmol) in 74% yield.

$^1$H NMR (MeOD-d4, 400 MHz): δ=7.71 (dd, J=8.0, 7.6 Hz, 1H), 7.44 (dd, J=8.8, 7.2 Hz, 1H), 7.27 (dd, J=2.8, 1.2 Hz, 1H), 7.15-7.11 (m, 2H), 7.09 (dd, J=4.8, 2.8 Hz, 1H), 6.75 (d, J=8.4 Hz, 1H), 6.54 (td, J=8.4, 2.8 Hz, 1H), 5.99 (dd, J=8.8, 6.0 Hz, 1H), 4.27-4.18 (m, 2H), 3.87 (d, J=16.4

Hz, 1H), 3.45 (d, J=16.4 Hz, 1H), 2.36-2.28 (m, 1H), 1.83-1.74 (m, 2H), 1.66-1.53 (m, 4H), 1.39-1.29 (m, 2H).

$^{13}$C NMR (MeOD-d4, 100 MHz): δ=166.9, 161.6, 158.6 (d, J=245 Hz), 157.2, 143.5, 138.2, 130.7 (d, J=4 Hz), 124.8 (d, J=8.5 Hz), 124.7, 124.5, 120.1, 114.7 (d, 0.1=25 Hz), 112.3 (d, J=21 Hz), 111.8, 108.0, 100.0, 68.3, 59.3, 39.1, 37.3, 27.5, 23.4.

Example 4—Preparation of 3-((2-chloro-4-fluorophenyl)thio)-6-(6-ethoxypyridin-2-yl)-6-(thiophen-3-yl)piperidine-2,4-dione

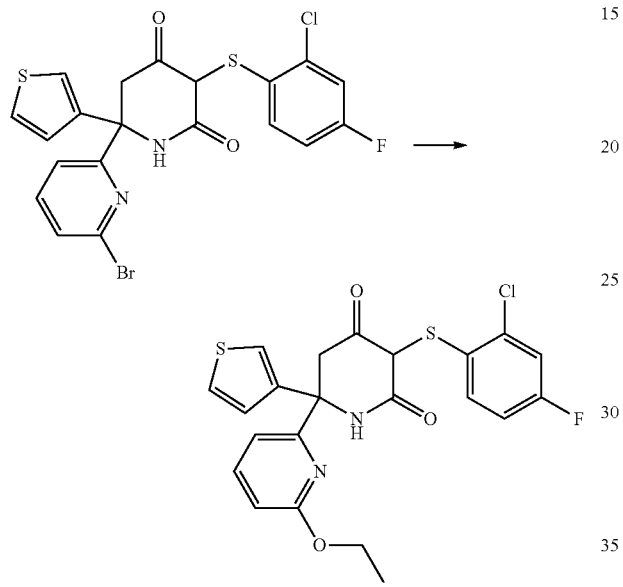

This compound was prepared in 90% yield according to the procedure in Example 3 using ethanol and 6-(6-bromopyridin-2-yl)-3-[(2-chloro-4-fluorophenyl)sulfanyl]-6-(thiophen-3-yl)piperidine-2,4-dione.

$^1$H NMR (MeOD-d4, 300 MHz): δ=7.71 (dd, J=8.1, 7.5 Hz, 1H), 7.44 (dd, J=5.1, 3.0 Hz, 1H), 7.27 (dd, J=3.0, 1.2 Hz, 1H), 7.15 (dd, J=5.1, 1.5 Hz, 1H), 7.12 (d, J=7.5 Hz, 1H), 7.09 (dd, J=8.4, 2.7 Hz, 1H), 6.75 (dd, J=8.1, 0.6 Hz, 1H), 6.55 (td, J=8.1, 2.7 Hz, 1H), 6.00 (dd, J=9.0, 5.7 Hz, 1H), 4.40 (q, J=6.9 Hz, 2H), 3.90 (d, J=16.5 Hz, 1H), 3.47 (d, J=16.5 Hz, 1H), 1.34 (t, J=6.9 Hz, 3H).

Example 5—Preparation of 6-[6-(cyclopentylmethoxy)pyridin-2-yl]-3-[(2,5-dichlorophenyl)sulfanyl]-6-(thiophen-3-yl)piperidine-2,4-dione

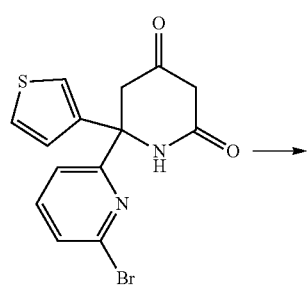

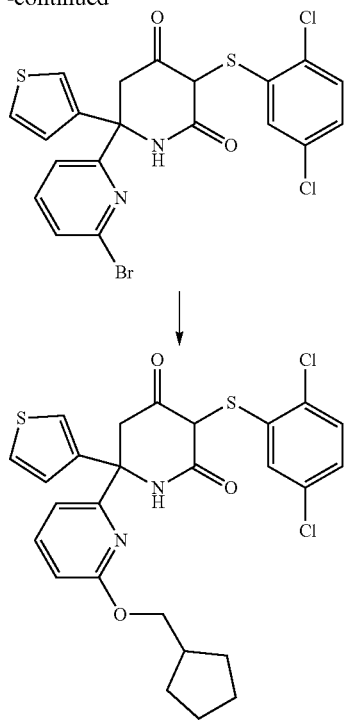

Step A: 1,2-bis(2,5-dichlorophenyl)disulfane (480 mg, 1.4 mmol, 0.6 eq) and potassium carbonate (930 mg, 6.8 mmol, 3 eq) were added to a solution of 6-(6-bromopyridin-2-yl)-6-(thiophen-3-yl)piperidine-2,4-dione (790 mg, 2.3 mmol, 1 eq) in MeOH (23 mL). The reaction was stirred for 2 hr under reflux, then concentrated under reduced pressure. Water (10 mL) and HCl 1M (7 mL) were added and the aqueous phase was extracted with ethyl acetate (3×15 mL). The combined organic phases were dried with Na$_2$SO$_4$, filtered and concentrated under reduced pressure. The crude product was purified by flash chromatography on silica gel (eluent: heptane/ethyl acetate: 70/30 to 30/70) to give 6-(6-bromopyridin-2-yl)-3-[(2,5-dichlorophenyl)sulfanyl]-6-(thiophen-3-yl)piperidine-2,4-dione (179 mg, 0.34 mmol) in 15% yield.

$^1$H NMR (MeOD-d4, 400 MHz): δ=7.75 (t, J=7.6 Hz, 1H), 7.61-7.56 (m, 2H), 7.45 (br s, 1H), 7.24-7.22 (m, 2H), 7.11 (d, J=1.2 Hz, 1H), 6.97 (d, J=8.4 Hz, 1H), 6.24 (s, 1H), 3.98 (d, J=16.4 Hz, 1H), 3.46 (d, J=16.4 Hz, 1H).

Step B: Cyclopentanemethanol (172 μL, 1.6 mmol, 5 eq) was added to a suspension of NaH (64 mg, 1.6 mmol, 5 eq) in THF (3.5 mL) at 0° C. The reaction was stirred at 0° C. for 30 min and 6-(6-bromopyridin-2-yl)-3-[(2,5-dichlorophenyl)sulfanyl]-6-(thiophen-3-yl)piperidine-2,4-dione (170 mg, 0.32 mmol, 1 eq) was added. The reaction was then stirred overnight under reflux and quenched by the addition of water (10 mL) and HCl 1M (5 mL). The aqueous phase was extracted with ethyl acetate (3×15 mL) and the combined organic phases were dried with Na$_2$SO$_4$, filtered and concentrated under reduced pressure. The crude product was purified by flash chromatography on silica gel (eluent: heptane/ethyl acetate: 75/25) to give 6-[6-(cyclopentylmethoxy)pyridin-2-yl]-3-[(2,5-dichlorophenyl)sulfanyl]-6-(thiophen-3-yl)piperidine-2,4-dione (104 mg, 0.19 mmol) in 59% yield.

$^1$H NMR (MeOD-d4, 400 MHz): δ=7.69 (t, J=8.0 Hz, 1H), 7.41 (dd, J=4.8, 3.2 Hz, 1H), 7.24-7.21 (m, 2H), 7.12-7.09 (m, 2H), 6.96 (dd, J=8.8, 2.8 Hz, 1H), 6.71 (d, J=8.0 Hz, 1H), 6.26 (d, J=2.4 Hz, 1H), 4.28-4.18 (m, 2H), 9.25 (d, J=16.4 Hz, 1H), 3.42 (d, J=16.4 Hz, 1H), 2.36-2.28 (m, 1H), 1.83-1.74 (m, 2H), 1.65-1.52 (m, 4H), 1.40-1.29 (m, 2H).

¹³C NMR (MeOD-d4, 100 MHz): δ=166.5, 161.6, 158.0, 143.7, 138.3, 137.5, 131.1, 128.5, 127.0, 124.7, 124.3, 123.5, 123.0, 119.9, 111.5, 68.2, 59.1, 39.1, 37.4, 27.6, 23.5.

Example 6—Preparation of 6-(6-bromopyridin-2-yl)-3-[(2,3-dichlorophenyl)sulfanyl]-6-(thiophen-3-yl)piperidine-2,4-dione Example 7—Preparation of 6-[6-(cyclopentylmethoxy)pyridin-2-yl]-3-[(2,3-dichlorophenyl)sulfanyl]-6-(thiophen-3-yl)piperidine-2,4-dione

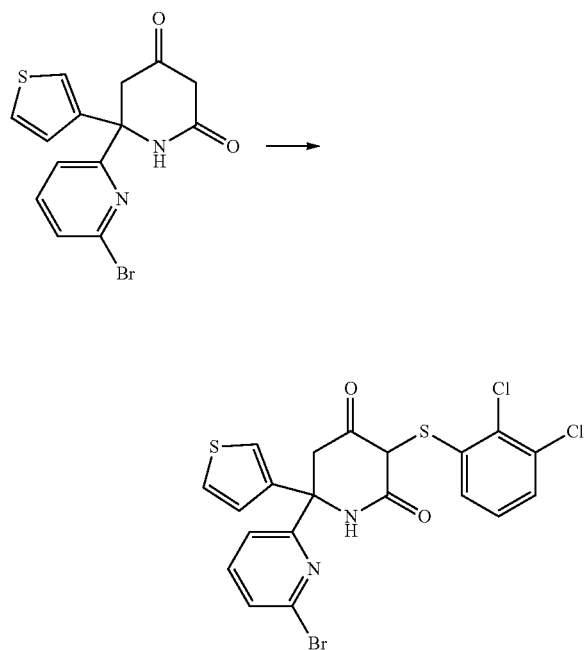

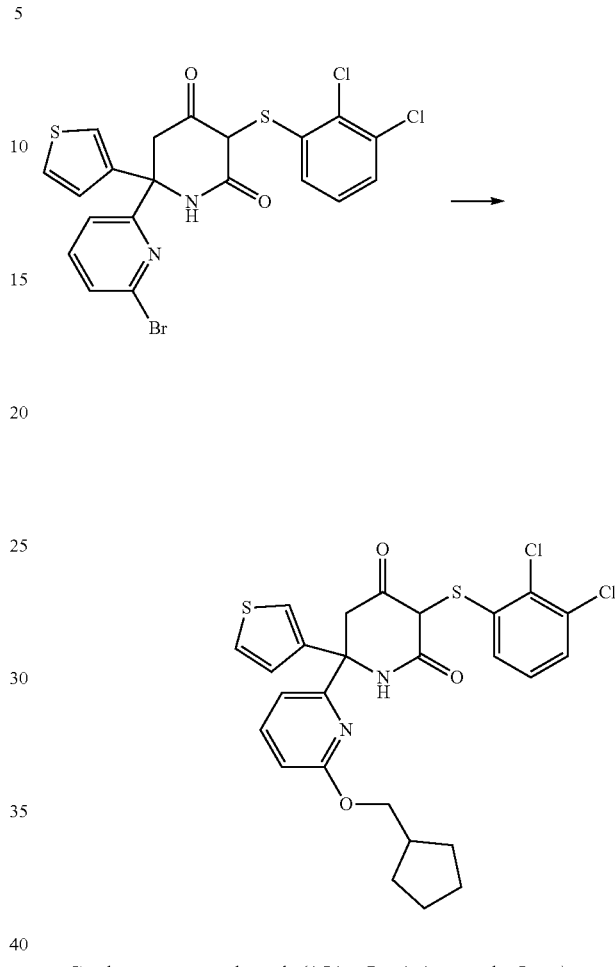

1,2-bis(2,3-dichlorophenyl)disulfane (463 mg, 1.3 mmol, 1.2 eq) and potassium carbonate (456 mg, 3.3 mmol, 3 eq) were added to a solution of 6-(6-bromopyridin-2-yl)-6-(thiophen-3-yl)piperidine-2,4-dione (400 mg, 1.1 mmol, 1 eq) in MeOH (11 mL). The reaction was stirred for 2 hr under reflux, and concentrated under reduced pressure. Water (10 mL) and HCl 1M (7 mL) were added and the aqueous phase was extracted with ethyl acetate (3×15 mL). The combined organic phases were dried with Na₂SO₄, filtered and concentrated under reduced pressure. The crude product was purified by flash chromatography on silica gel (eluent: heptane/ethyl acetate: 70/30 to 30/70) to give 6-(6-bromopyridin-2-yl)-3-[(2,3-dichlorophenyl)sulfanyl]-6-(thiophen-3-yl)piperidine-2,4-dione (447 mg, 0.85 mmol) in 77% yield.

¹H NMR (MeOD-d4, 400 MHz): δ=7.74 (t, J=8.0 Hz, 1H), 7.59 (t, J=7.6 Hz, 1H), 7.47 (dd, J=5.2, 3.2 Hz, 1H), 7.30 (dd, J=2.8, 1.6 Hz, 1H), 7.15 (d, J=1.2 Hz, 1H), 7.14 (dd, J=2.8, 1.2 Hz, 1H), 6.79 (t, J=8.0 Hz, 1H), 5.99 (d, J=8.0, 1H), 3.89 (d, J=16.4 Hz, 1H), 3.49 (d, J=16.4 Hz, 1H).

¹³C NMR (MeOD-d4, 100 MHz): δ=176.6, 169.4, 164.9, 145.7, 142.1, 141.3, 141.0, 134.0, 129.2, 128.6, 128.4, 128.0, 127.3, 127.0, 124.6, 123.5, 121.6, 95.5, 62.1, 41.9, 14.5.

Cyclopentanemethanol (151 µL, 1.4 mmol, 5 eq) was added to a suspension of NaH (56 mg, 1.4 mmol, 5 eq) in THF (3.5 mL) at 0° C. The reaction was stirred at 0° C. for 30 min and 6-(6-bromopyridin-2-yl)-3-[(2,3-dichlorophenyl)sulfanyl]-6-(thiophen-3-yl)piperidine-2,4-dione (150 mg, 0.28 mmol, 1 eq) was added. The reaction was then stirred overnight under reflux and quenched by the addition of water (10 mL) and HCl 1M (5 mL). The aqueous phase was extracted with ethyl acetate (3×15 mL) and the combined organic phases were dried with Na₂SO₄, filtered and concentrated under reduced pressure. The crude product was purified by flash chromatography on silica gel (eluent: heptane/ethyl acetate: 75/25 to 50/50) to give 6-[6-(cyclopentylmethoxy)pyridin-2-yl]-3-[(2,3-dichlorophenyl)sulfanyl]-6-(thiophen-3-yl)piperidine-2,4-dione (73 mg, 0.13 mmol) in 48% yield.

¹H NMR (MeOD-d4, 400 MHz): δ=7.71 (t, J=8.0 Hz, 1H), 7.45-7.43 (m, 1H), 7.28-7.27 (m, 1H), 7.15-7.11 (m, 3H), 6.76-6.69 (m, 2H), 5.90 (d, J=8.0 Hz, 1H), 4.27-4.18 (m, 1H), 3.88 (d, J=16.4 Hz, 1H), 3.45 (d, J=16.4 Hz, 1H), 2.35-2.27 (m, 2H), 1.80-1.74 (m, 2H), 1.63-1.52 (m, 4H), 1.37-1.30 (m, 2H).

¹³C NMR (MeOD-d4, 100 MHz): δ=169.8, 164.5, 161.1, 146.4, 141.2, 133.9, 129.1, 128.4, 127.6, 127.4, 126.9, 124.6, 123.0, 114.8, 110.9, 71.2, 62.2, 42.1, 40.2, 30.5, 26.3.

Example 8—Preparation of 3-((2-chloro-4-fluoro-phenyl)thio)-6-(4-morpholinophenyl)-6-(thiophen-3-yl)piperidine-2,4-dione

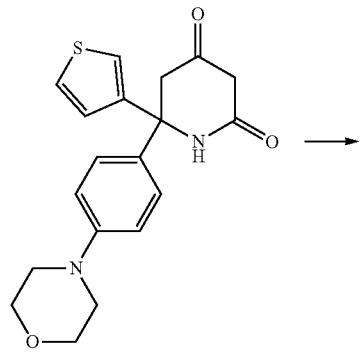

→

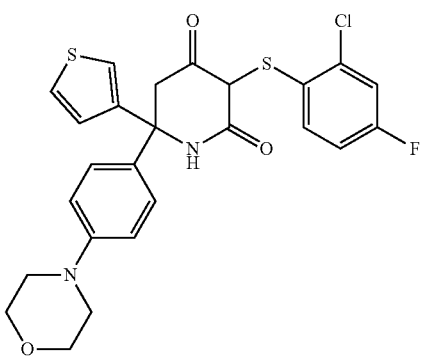

This compound was prepared according to Example 2, using 6-(4-morpholinophenyl)-6-(thiophen-3-yl)piperidine-2,4-dione and 1,2-bis(2-chloro-4-fluorophenyl)disulfane, in 55% yield.

$^1$H NMR (MeOD-d4, 400 MHz): δ=7.56 (dd, J=5.2, 2.8 Hz, 1H), 7.35 (d, J=8.8 Hz, 2H), 7.32-7.31 (m, 1H), 7.21-7.16 (m, 2H), 7.02 (d, J=8.8 Hz, 2H), 7.60 (td, J 8.4, 2.4 Hz, 1H), 5.96 (dd, J=8.8, 5.6 Hz, 1H), 3.85 (dd, J=4.8, 4.8 Hz, 4H), 3.28 (s, 2H), 3.20 (dd, J=5.2, 4.4 Hz, 4H).

Example 9—Preparation of 3-((2,3-dichlorophenyl)thio)-6-(4-morpholinophenyl)-6-(thiophen-3-yl)piperidine-2,4-dione

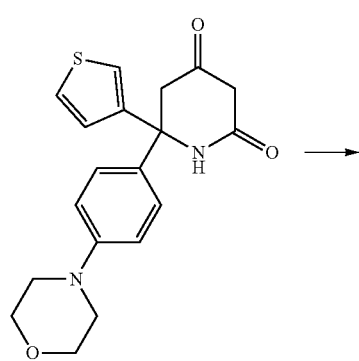

→

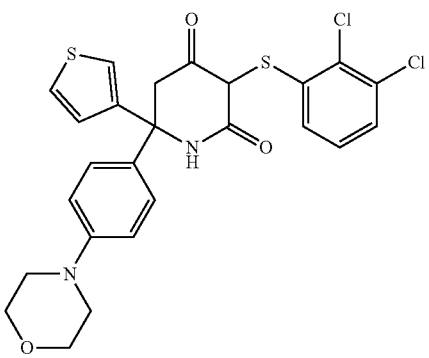

This compound was prepared according to Example 2, using 6-(4-morpholinophenyl)-6-(thiophen-3-yl)piperidine-2,4-dione and 1,2-bis(2,3-dichlorophenyl)disulfane, in 55% yield. In this example, Step B in the preparation of the starting material was carried out using (S)-2-methylpropane-2-sulfinamide in place of the racemate.

$^1$H NMR (MeOD-d4, 300 MHz): δ=7.51 (dd, J=5.1, 3.0 Hz, 1H), 7.34 (d, J=9.0 Hz, 2H), 7.28-7.27 (m, 1H), 7.17 (dd, J=5.1, 1.5 Hz, 1H), 7.13 (dd, J=8.1, 1.5 Hz, 1H), 7.00 (d, J=9.0 Hz, 2H), 6.73 (t, J=8.1 Hz, 1H), 5.92 (dd, J=8.1, 1.5 Hz, 1H), 3.87-3.84 (m, 4H), 3.46 (s, 2H), 3.21-3.17 (m, 4H).

Example 10—Preparation of 3-((2,5-dichlorophenyl)thio)-6-(4-morpholinophenyl)-6-(thiophen-3-yl)piperidine-2,4-dione

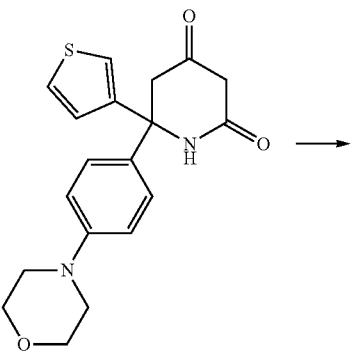

→

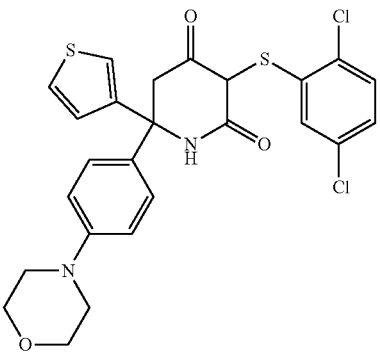

This compound was prepared according to Example 2, using 6-(4-morpholinophenyl)-6-(thiophen-3-yl)piperidine-2,4-dione and 1,2-bis(2,5-dichlorophenyl)disulfane, in 55% yield.

¹H NMR (MeOD-d4, 400 MHz): δ=7.50 (dd, J=5.2, 3.2 Hz, 1H), 7.33 (d, J=8.8 Hz, 2H), 7.28 (d, J=8.4 Hz, 1H), 7.26 (dd, J=2.8, 1.2 Hz, 1H), 7.14 (d, J=4.8, 1.2 Hz, 1H), 7.03-7.01 (m, 1H), 7.00 (d, J=9.2 Hz, 2H), 6.30 (d, J=2.8 Hz), 3.84-3.82 (m, 4H), 3.50 (s, 2H), 3.20-3.17 (m, 4H).

Example 10 was tested in the assays as the racemate and additionally as single enantiomers. It was possible to acquire the individual enantiomers by chiral preparative HPLC of the final products using an ethanol/acetonitrile/diethylamine (90/10/0.1) solvent system. Analysis of the enantiomers by HPLC on a ChiralPak IC column using the same solvent system revealed that the enantiomers had been isolated in 100.0% (Enantiomer 1: $R_t$=5.0 min) and 99.4% (Enantiomer 2: $R_t$=7.0 min) e.e.

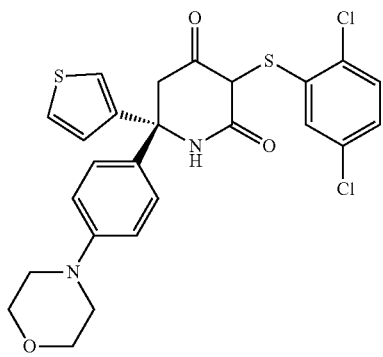

(6R)-3-((2,5-dichlorophenyl)thio)-6-(4-morpholinophenyl)-6-(thiophen-3-yl)piperidine-2,4-dione

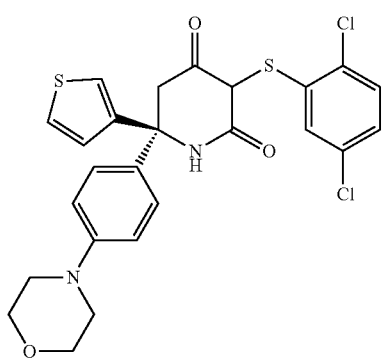

(6S)-3-((2,5-dichlorophenyl)thio)-6-(4-morpholinophenyl)-6-(thiophen-3-yl)piperidine-2,4-dione Example 11—Preparation of 5-[(2-chloro-4-fluorophenyl)sulfanyl]-2-[6-(cyclopentylmethoxy)pyridin-2-yl]-6-oxo-2-(thiophen-3-yl)-1,2,3,6-tetrahydropyridin-4-yl ethyl carbonate

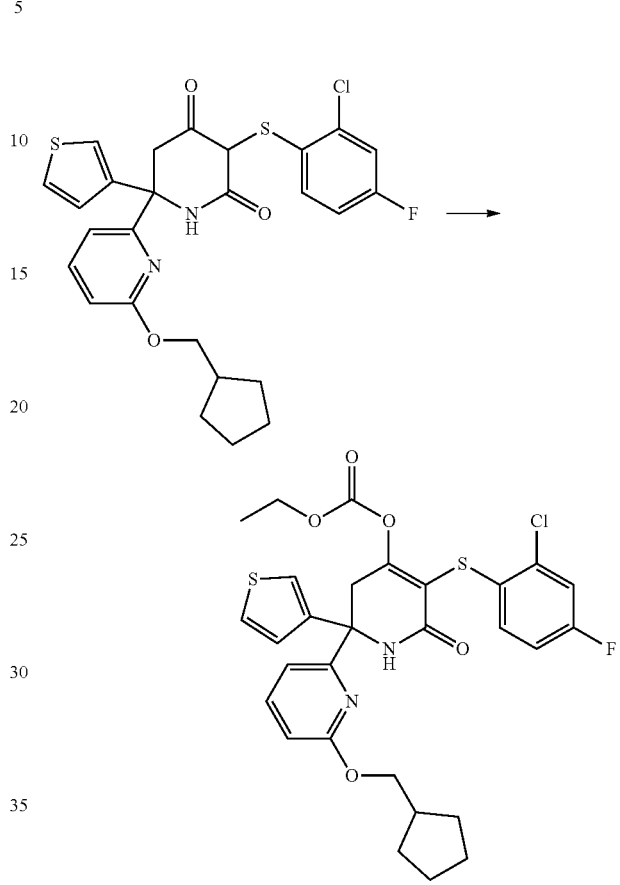

To a solution of 3-((2-chloro-4-fluorophenyl)thio)-6-(6-(cyclopentylmethoxy)pyridin-2-yl)-6-(thiophen-3-yl)piperidine-2,4-dione (80 mg, 0.15 mmol, 1 eq) in DCM (1.5 mL) at 0° C. was added to diisoprylamineethylamine (40 μL, 0.23 mmol, 1.5 eq). After 5 min at 0° C., ethyl chloroformate (17 μL, 0.18 mmol, 1.2 eq) was added and the reaction was stirred at 0° C. for 1.5 hr. The reaction was quenched by the addition of a saturated aqueous solution of NH₄Cl (2 mL) and water (5 mL) and the aqueous phase was extracted with ethyl acetate (3×10 mL). The combined organic phases were dried with Na₂SO₄, filtered and concentrated under vacuo. The crude product was purified by flash chromatography on silica gel (eluent: heptane/ethyl acetate: 80/20 to 50/50) to give 5-[(2-chloro-4-fluorophenyl)sulfanyl]-2-[6-(cyclopentylmethoxy)pyridin-2-yl]-6-oxo-2-(thiophen-3-yl)-1,2,3,6-tetrahydropyridin-4-yl ethyl carbonate (55 mg, 91 μmol) in 61% yield.

¹H NMR (MeOD-d4, 400 MHz): δ=7.70 (t, J=7.6 Hz, 1H), 7.45-7.42 (m, 1H), 7.26-7.25 (m, 1H), 7.14-7.11 (m, 2H), 7.06 (d, J=7.2 Hz, 1H), 6.75 (d, J=8.4 Hz, 1H), 6.65 (td, J.=8.0, 2.8 Hz, 1H), 6.32 (dd, J=8.4, 5.6 Hz, 1H), 4.26-4.21 (m, 3H), 4.17-4.12 (m, 1H), 3.94 (d, J=17.2 Hz, 1H), 3.58 (d, J=17.2 Hz, 1H), 2.36-2.29 (m, 1H), 1.83-1.75 (m, 2H), 1.66-1.54 (m, 4H), 1.38-1.27 (m, 2H), 1.29 (t, J=7.2 Hz, 3H).

¹³C NMR (MeOD-d4, 100 MHz): δ=166.1, 164.5 (d, J=221 Hz), 164.4, 160.6, 151.8, 145.7, 141.1, 134.5 (d, J=10.6 Hz), 131.5 (d, J=8.6 Hz), 131.2 (d, J=3.6 Hz), 127.7, 127.4, 123.5, 117.8 (d, J=25.5 Hz), 116.1, 115.5 (d, J=21.7 Hz), 115.1, 111.1, 71.3, 67.0, 62.8, 41.3, 40.2, 30.49, 30.43, 26.36, 26.32, 14.3

Example 12—Preparation of 6'-(cyclopentylmethoxy)-5-((2,3-dichlorophenyl)thio)-6-oxo-2-(thiophen-3-yl)-1,2,3,6-tetrahydro-[2,2'-bipyridin]-4-yl methyl carbonate

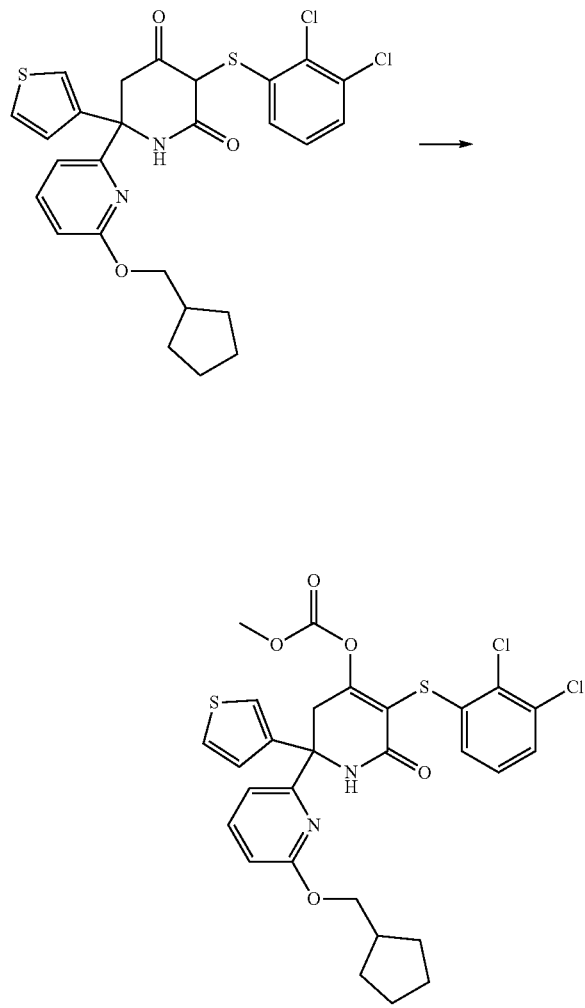 [SMILES: O=C1CC(c2ccsc2)(c2cccc(OCC3CCCC3)n2)NC(=O)C1Sc1ccc(Cl)cc1Cl ; COCCOC(=O)OC1=C(Sc2ccc(Cl)cc2Cl)C(=O)NC(c2ccsc2)(c2cccc(OCC3CCCC3)n2)C1]

This compound was prepared in 51% yield according to Example 11 using methyl chloroformate and 6-(6-(cyclopentylmethoxy)pyridin-2-yl)-3-((2,3-dichlorophenyl)thio)-6-(thiophen-3-yl)piperidine-2,4-dione.

$^1$H NMR (MeOD-d4, 400 MHz): δ=7.73 (t, J=8.0 Hz, 1H), 7.47-7.44 (m, 1H), 7.30-7.27 (m, 1H), 7.22 (d, J=8.0 Hz, 1H), 7.14 (d, J=5.2 Hz, 1H), 7.09 (d, J=7.6 Hz, 1H), 6.80-6.76 (m, 2H), 6.03 (d, J=8.0 Hz, 1H), 4.26-4.14 (m, 2H), 3.98 (d, J=16.8 Hz, 1H), 3.84 (s, 3H), 3.64 (d, J=16.8 Hz, 1H), 2.36-2.28 (m, 1H), 1.82-1.74 (m, 2H), 1.67-1.52 (m, 4H), 1.39-1.30 (m, 2H).

$^{13}$C NMR (MeOD-d4, 101 MHz): δ=167.0, 165.9, 164.5, 160.6, 152.4, 149.7, 145.7, 141.1, 138.9, 134.2, 130.4, 128.6, 128.2, 127.7, 127.5, 127.0, 123.6, 115.4, 115.2, 111.2, 71.3, 62.9, 56.8, 40.2, 30.46, 30.44, 26.3.

Example 13—Preparation of 5-((2-chloro-4-fluorophenyl)thio)-6'-(cyclopentylmethoxy)-6-oxo-2-(thiophen-3-yl)-1,2,3,6-tetrahydro-[2,2'-bipyridin]-4-yl acetate

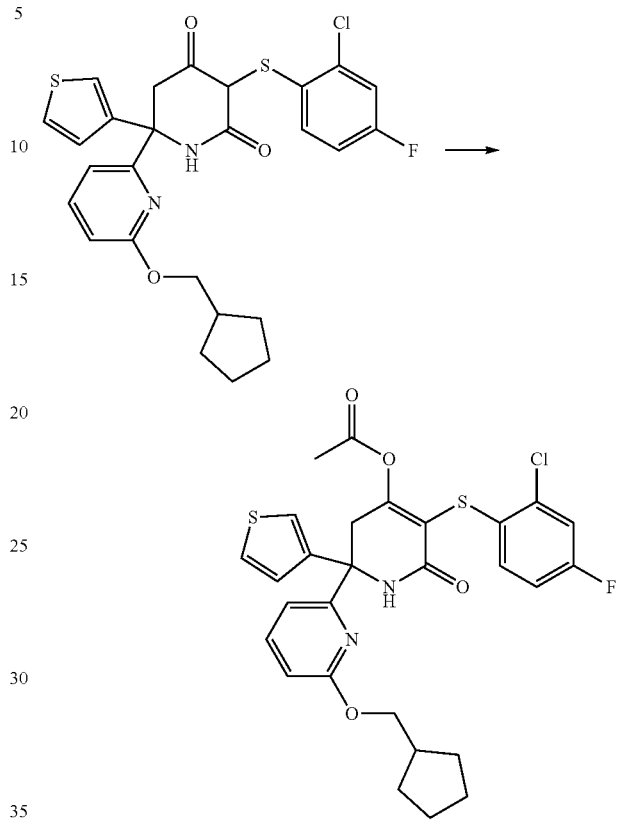

This compound was prepared in 42% yield according to Example 11 using acetyl chloride and 3-((2-chloro-4-fluorophenyl)thio)-6-(6-(cyclopentylmethoxy)pyridin-2-yl)-6-(thiophen-3-yl)piperidine-2,4-dione.

$^1$H NMR (400 MHz, CDCl$_3$): δ=7.66 (br s, 1H), 7.44 (t, J=8.0 Hz, 1H), 7.39 (dd, J=5.2, 3.2 Hz, 1H), 7.24-7.23 (m, 1H), 7.16 (dd, J=5.2, 1.2 Hz, 1H), 7.03 (dd, J=8.0, 2.4 Hz, 1H), 6.62-6.57 (m, 2H), 6.48 (d, J=7.2 Hz), 6.09 (dd, J=8.8, 5.6 Hz, 1H), 4.15-4.05 (m, 4H), 3.25 (d, J=17.2 Hz, 1H), 2.45 (s, 3H), 2.33 (q, J=7.6 Hz, 1H), 1.85-1.78 (m, 2H), 1.67-1.56 (m, 4H), 1.40-1.32 (m, 2H).

Example 14—Preparation of 5-((2-chloro-4-fluorophenyl)thio)-2-(4-morpholinophenyl)-6-oxo-2-(thiophen-3-yl)-1,2,3,6-tetrahydropyridin-4-yl propyl carbonate

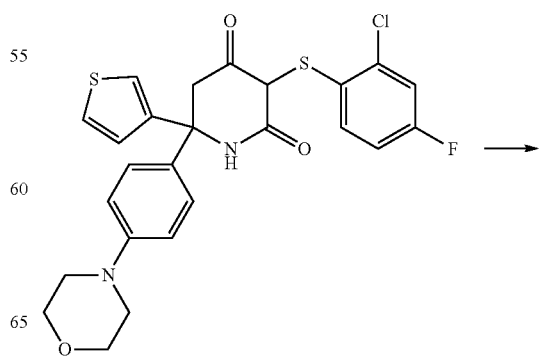

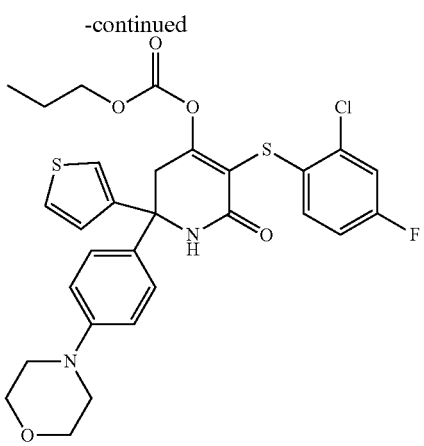

This compound was prepared in 68% yield according to Example 11 using 3-((2-chloro-4-fluorophenyl)thio)-6-(4-morpholinophenyl)-6-(thiophen-3-yl)piperidine-2,4-dione and n-propyl chloroformate.

¹H NMR (MeOD-d4, 400 MHz): β=7.52 (dd, J=5.2, 2.8 Hz, 1H), 7.35-7.33 (m, 1H), 7.31 (d, J=8.8 Hz, 2H), 7.16-7.13 (m, 2H), 7.00 (d, J=8.8 Hz, 2H), 6.64 (td, J=8.4, 2.8 Hz, 1H), 6.20 (dd, J=8.8, 6.0 Hz, 1H), 4.17 (t, J=6.4 Hz, 2H), 3.87-3.85 (m, 4H), 3.60 (br s, 2H), 3.21-3.18 (m, 4H), 1.71 (sext, J=7.2 Hz, 2H), 0.97 (t, J=7.2 Hz, 3H).

Example 15—Preparation of 5-((2,3-dichlorophenyl)thio)-2-(4-morpholinophenyl)-6-oxo-2-(thiophen-3-yl)-1,2,3,6-tetrahydropyridin-4-yl ethyl carbonate

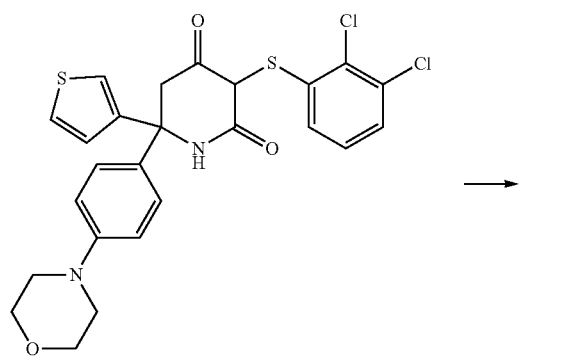

This compound was prepared in 60% yield according to Example 11 using 3-((2,3-dichlorophenyl)thio)-6-(4-morpholinophenyl)-6-(thiophen-3-yl)piperidine-2,4-dione and ethyl chloroformate.

¹H NMR (MeOD-d4, 300 MHz): δ=7.51 (dd, J=5.1, 3.0 Hz, 1H), 7.35 (dd, J=6.0, 1.5 Hz, 1H), 7.31 (d, J=9.0 Hz, 2H), 7.20 (dd, J=8.1, 1.5 Hz, 1H), 7.15 (dd, J=6.6, 1.5 Hz, 1H), 6.99 (d, J=9.0 Hz, 2H), 6.78 (t, J=8.1 Hz, 1H), 6.00 (dd, J=8.1, 1.5 Hz, 1H), 4.57 (m, 1H), 4.24 (q, J=7.2 Hz, 2H), 3.86-3.81 (m, 4H), 3.62 (s, 2H), 3.19-3.16 (m, 4H), 1.28 (t, J=7.2 Hz, 4H).

Example 16—Preparation of 6'-(cyclopentylmethoxy)-5-((2,5-dichlorophenyl)thio)-6-oxo-2-(thiophen-3-yl)-1,2,3,6-tetrahydro-[2,2'-bipyridin]-4-yl decyl carbonate

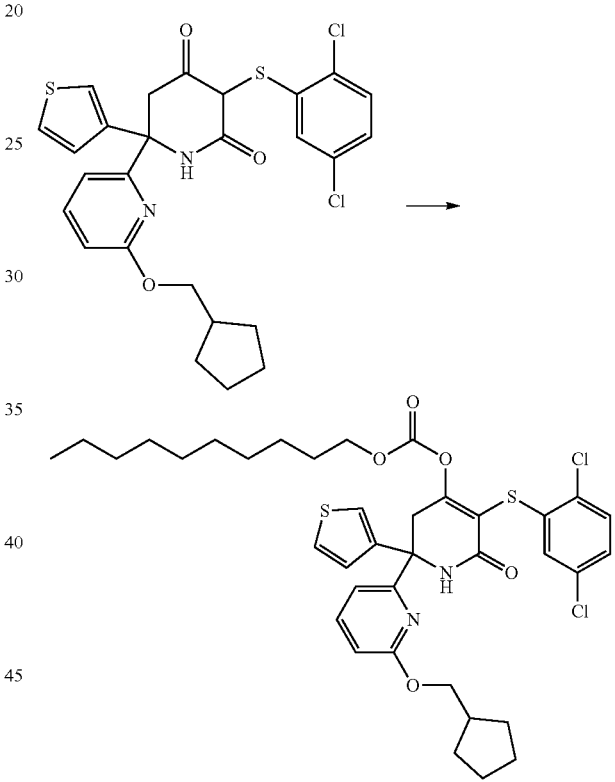

This compound was prepared in 50% yield according to Example 11 using 6-(6-(cyclopentylmethoxy)pyridin-2-yl)-3-((2,5-dichlorophenyl)thio)-6-(thiophen-3-yl)piperidine-2,4-dione and decyl carbonochloridate.

¹H NMR (MeOD-d4, 400 MHz): δ=7.80 (dd, J=8.0, 7.6 Hz, 1H), 7.53 (dd, J=4.8, 2.8 Hz, 1H), 7.40-7.38 (m, 2H), 7.20-7.16 (m, 3H), 6.80 (dd, J=8.0, 0.8 Hz, 1H), 6.44 (d, J=2.4 Hz, 1H), 4.32 (m, 2H), 4.26-4.19 (m, 4H), 4.09 (d, J=17.2 Hz, 1H), 3.62 (d, J=17.2 Hz, 1H), 2.38 (q, J=7.6 Hz, 1H), 1.86-1.79 (m, 2H), 1.70-1.56 (m, 6H), 1.42-1.32 (m, 16H), 0.94 (t, J=7.2 Hz, 3H).

¹³C NMR (MeOD-d4, 100 MHz): δ=166.5, 164.5, 164.1, 160.7, 151.6, 146.0, 141.6, 138.1, 133.9, 131.9, 130.7, 128.13, 127.98, 127.96, 127.6, 123.4, 115.0, 114.6, 111.4, 101.2, 71.11, 71.09, 62.6, 32.9, 30.52, 30.49, 30.48, 30.32, 30.15, 29.4, 26.6, 26.37, 26.33, 23.7, 14.8.

Example 17—Preparation of 5-((2,5-dichlorophenyl)thio)-2-(4-morpholinophenyl)-6-oxo-2-(thiophen-3-yl)-1,2,3,6-tetrahydropyridin-4-yl (2-methoxyethyl) carbonate

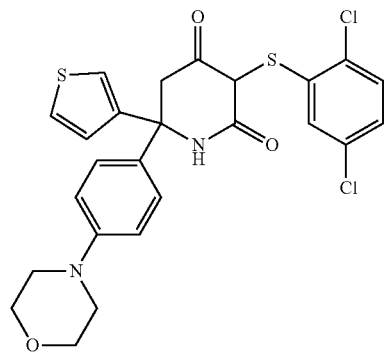

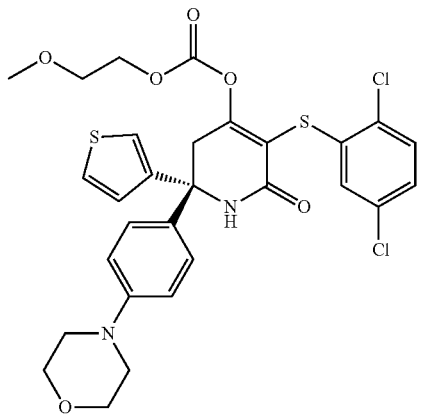

(R)-5-((2,5-dichlorophenyl)thio)-2-
(4-morpholinophenyl)-6-oxo-2-
(thiophen-3-yl)-1,2,3,6-
tetrahydropyridin-4-yl (2-
methoxyethyl) carbonate

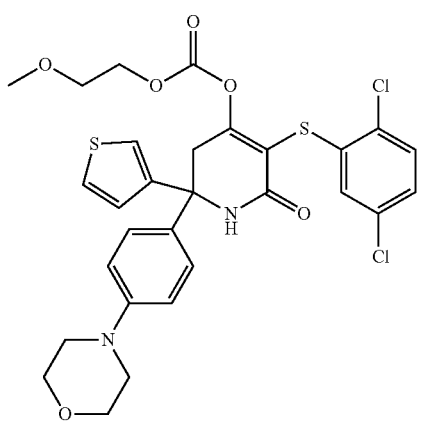

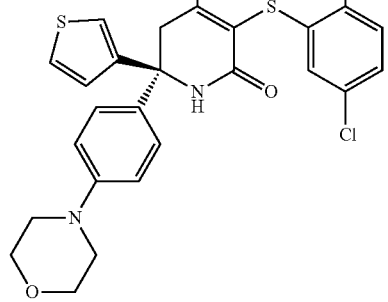

(S)-5-((2,5-dichlorophenyl)thio)-2-
(4-morpholinophenyl)-6-oxo-2-
(thiophen-3-yl)-1,2,3,6-
tetrahydropyridin-4-yl (2-
methoxyethyl) carbonate This compound was prepared in 60% yield according to Example 11 using 3-((2,5-dichlorophenyl)thio)-6-(4-morpholinophenyl)-6-(thiophen-3-yl)piperidine-2,4-dione and 2-(methoxy)ethyl chloroformate.

$^1$H NMR (MeOD-d4, 300 MHz): δ=7.46 (dd, J=5.1, 3.0 Hz, 1H), 7.31-7.28 (m, 2H), 7.28-7.25 (d, J=8.4 Hz, 2H), 7.10 (dd, J=5.1, 1.5 Hz, 1H), 7.05 (d, J=8.7, 2.4 Hz, 1H), 6.98 (d, J=9.0 Hz, 2H), 6.42 (d, J=2.4 Hz, 1H), 4.57 (s, 1H), 4.34-4.31 (m, 2H), 3.84-3.81 (m, 4H), 3.63-3.59 (m, 4H), 3.34 (s, 3H), 3.18-3.15 (m, 4H).

The compound of Example 17 was tested in the assays as the racemate and additionally as single enantiomers. It was possible to acquire the individual enantiomers by chiral preparative HPLC of the starting material using an ethanol/acetonitrile/diethylamine (90/10/0.1) solvent system. Analysis of the enantiomers by analytical HPLC on a ChiralPak IC column using the same solvent system revealed that the enantiomers had been isolated in 100% (Enantiomer 1: $R_t$=5.0 min) and 99.4% (Enantiomer 2: $R_t$=7.0 min) e.e. The method in Example 11 could then be performed on each enantiomer individually.

Example 18—Preparation of 6-(6-bromo-2-pyridyl)-3-(2-chlorophenyl)sulfanyl-6-(3-thienyl)tetrahydropyran-2,4-dione

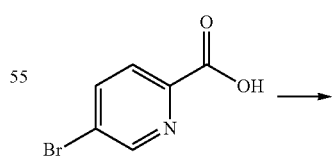

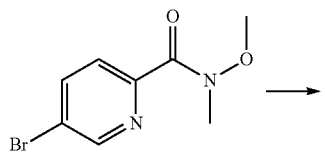

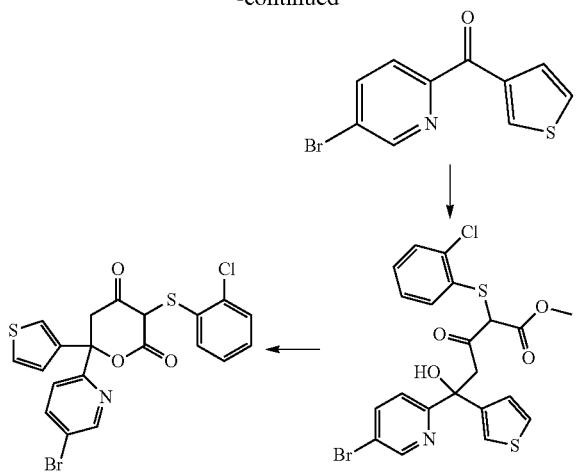

Step A: 1,1'-carbonyldiimidazole (21.1 g, 130 mmol) was added to a solution of 5-bromopicolinic acid (20.2 g, 100 mmol) in DCM at 0° C. The mixture was stirred at 0° C. for 2 hr and trimethylamine (42 mL, 300 mmol) was added. Stirring was continued for 45 min at 0° C. and N,O-dimethylhydroxylamine hydrochloride (12.7 g, 130 mmol) was added. The mixture was allowed to warm up to room temperature overnight and diluted with DCM (300 mL). The organic phase was washed with aqueous saturated NH$_4$Cl (twice), water and aqueous saturated NaHCO$_3$, dried over Na$_2$SO$_4$ and concentrated under reduced pressure to give 5-bromo-N-methoxy-N-methylpicolinamide in 58% yield.

Step B: To a solution of 3-bromothiophene (6.5 mL, 69 mmol) in di-iso-propylether (175 mL) at −78° C. was added a solution of n-butyllithium (27.6 mL, 69 mmol) in hexanes slowly over 15 min. The mixture was stirred for 30 min at −78° C. and 5-bromo-N-methoxy-N-methylpicolinamide (14.1 g, 57.6 mmol) in di-iso-propylether (10 mL) was added. The mixture was stirred for 2 h between −78 and −70° C. Saturated aqueous NH$_4$Cl (75 mL) was added and the aqueous phase was extracted with ethyl acetate (3 times). The combined organic phases were washed with brine, dried over Na$_2$SO$_4$ and concentrated under reduced pressure. The crude product was purified by flash column chromatography (silica gel, eluent: heptane/ethyl acetate=20% to 30 to 50) to give (5-bromopyridin-2-yl)(thiophen-3-yl)methanone in 66% yield.

Step C: To a solution of di-iso-propylamine (309 μL, 2.2 mmol) in THF (4 mL) at −78° C. was added a solution of n-butyllithium (0.84 mL, 2.1 mmol) in hexanes. After 10 min at −78° C., methyl 2-((2-chlorophenyl)thio)-3-oxobutanoate (259 mg, 1.0 mmol) in THF (2 mL) was added. The mixture was stirred for 30 min at 0° C. and (5-bromopyridin-2-yl)(thiophen-3-yl)methanone (161 mg, 0.6 mmol) in THF (2 mL) was added. After 1.5 h at 0° C., the reaction was quenched with aqueous saturated NH$_4$Cl and the aqueous phase was extracted with ethyl acetate (3 times). The combined organic phases were dried over Na$_2$SO$_4$ and concentrated under reduced pressure. The crude product was purified by flash column chromatography (silica gel, eluent: heptane/ethyl acetate=10% to 20) to give methyl 5-(5-bromopyridin-2-yl)-2-((2-chlorophenyl)thio)-5-hydroxy-3-oxo-5-(thiophen-3-yl)pentanoate in 83% yield.

Step D: A solution of methyl 5-(5-bromopyridin-2-yl)-2-((2-chlorophenyl)thio)-5-hydroxy-3-oxo-5-(thiophen-3-yl)pentanoate (255 mg, 0.48 mmol) and K$_2$CO$_3$ (200 mg, 1.44 mmol) in methanol (2.4 mL) was stirred at 60° C. for 6 h. The mixture was concentrated under reduced pressure and diluted with water and aqueous HCl. The aqueous phase was extracted with ethyl acetate (3 times) and the combined organic phases were dried over Na$_2$SO$_4$ and concentrated under reduced pressure. The crude product was purified by flash column chromatography (silica gel, eluent: heptane/ethyl acetate=20%) to give 6-(6-bromo-2-pyridyl)-3-(2-chlorophenyl)sulfanyl-6-(3-thienyl)tetrahydropyran-2,4-dione in 61% yield.

$^1$H NMR (300 MHz): δ=8.61 (dd, J=2.1, 0.6 Hz, 1H), 7.81 (dd, J=8.4, 2.1 Hz, 1H), 7.75 (br s, 1H), 7.61 (dd, J=8.4, 0.6 Hz, 1H), 7.38 (dd, J=3.0, 1.5 Hz, 1H), 7.33-7.26 (m, 2H), 7.12 (dd, J=5.1, 1.5 Hz, 1H), 7.06 (td, J=7.8, 1.5 Hz, 1H), 6.90-6.84 (m, 1H), 6.21 (dd, J=7.8, 1.2 Hz, 1H), 4.04 (d, J=17.4 Hz, 1H), 3.55 (d, J=17.4 Hz, 1H).

Example 19—Preparation of 3-((2-chlorophenyl)thio)-6-(pyrimidin-5-yl)-6-(thiophen-3-yl)dihydro-2H-pyran-2,4(3H)-dione

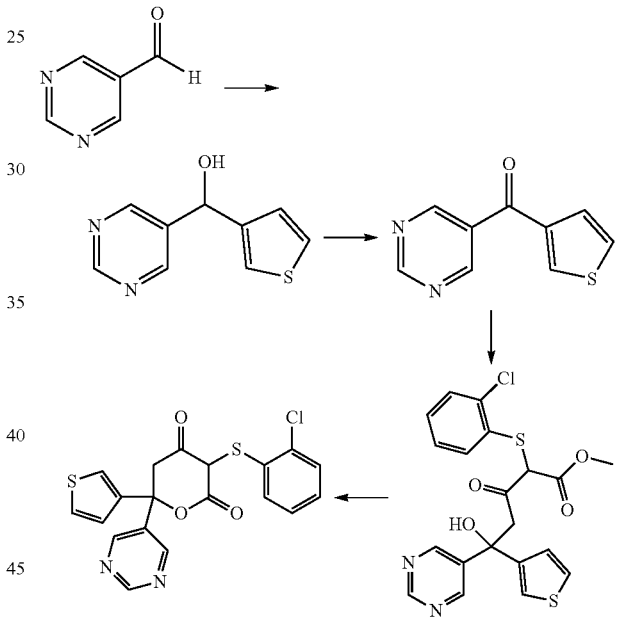

Step A: To a solution of pyrimidine-5-carbaldehyde (1.0 g, 6.3 mmol) in THF (63 mL) at −78° C. was added tetramethylethylenediamine (1.4 mL, 9.5 mmol) and n-butyllithium (2.8 mL, 6.9 mmol) in hexanes. After 30 min at −78° C., thiophene-3-carbaldehyde (830 μL, 9.5 mmol) was added and the mixture was allowed to warm to −40° C. over a period of 1.5 h and stirred for another 30 min at −40° C. The reaction was stopped by the addition of aqueous saturated NH$_4$Cl and diluted with ethyl acetate. The organic phase was washed with brine, dried over Na$_2$SO$_4$ and concentrated under reduced pressure. The crude product was purified by flash column chromatography (silica gel, eluent: heptane/ethyl acetate=30% to 50 to 70) to give pyrimidin-5-yl(thiophen-3-yl)methanol in 41% yield.

Step B: To a solution of pyrimidin-5-yl(thiophen-3-yl)methanol (480 mg, 2.5 mmol) in dichloromethane at 0° C. were added TEMPO (3.9 mg, 25 μmol), KBr (20 mg, 0.25 mmol), tetrabutylammoniumhydrogen sulfate (41 mg, 0.12 mmol) and a NaOCl solution in water (2.4 mL, 3.2 mmol).

The mixture was vigorously stirred at 0° C. for 1.5 hr and diluted with water. The aqueous phase was extracted with dichloromethane (twice) and the combined organic phases were dried over $Na_2SO_4$ and concentrated under reduced pressure. The crude product was purified by flash column chromatography (silica gel, eluent: heptane/ethyl acetate=20% to 30 to 50) to give pyrimidin-5-yl(thiophen-3-yl)methanone in 60% yield.

Step C: Methyl 2-((2-chlorophenyl)thio)-5-hydroxy-3-oxo-5-(pyrimidin-5-yl)-5-(thiophen-3-yl)pentanoate was prepared in 56% yield according to step C, Example 18, using pyrimidin-5-yl(thiophen-3-yl)methanone.

Step D: A solution of methyl 2-((2-chlorophenyl)thio)-5-hydroxy-3-oxo-5-(pyrimidin-5-yl)-5-(thiophen-3-yl)pentanoate (250 mg, 0.78 mmol) and $K_2CO_3$ (323 mg, 2.34 mmol) in methanol was stirred under reflux for 7 hr. The mixture was concentrated under reduced pressure and diluted with water and aqueous HCl. The aqueous phase was extracted with ethyl acetate (3 times) and the combined organic phases were dried over $Na_2SO_4$ and concentrated under reduced pressure. The crude product was purified by flash column chromatography (silica gel, eluent: DCM/MeOH=0% to 1 to 2%) to give 3-((2-chlorophenyl)thio)-6-(pyrimidin-5-yl)-6-(thiophen-3-yl)dihydro-2H-pyran-2,4(3H)-dione in 30% yield.

$^1$H NMR (300 MHz): S=9.11 (s, 1H), 8.81 (s, 2H), 7.48-7.47 (m, 2H), 7.21-7.13 (m, 2H), 6.95-6.90 (m, 1H), 6.80-6.75 (m, 1H), 5.90 (d, J=8.1 Hz, 1H), 3.63 (d, J=17.4 Hz, 1H), 3.48 (d, J=17.4 Hz, 1H).

Example 20—Preparation of 3-((2-chlorophenyl)thio)-6-(pyridin-2-yl)-6-(thiophen-3-yl)dihydro-2H-pyran-2,4(3H)-dione

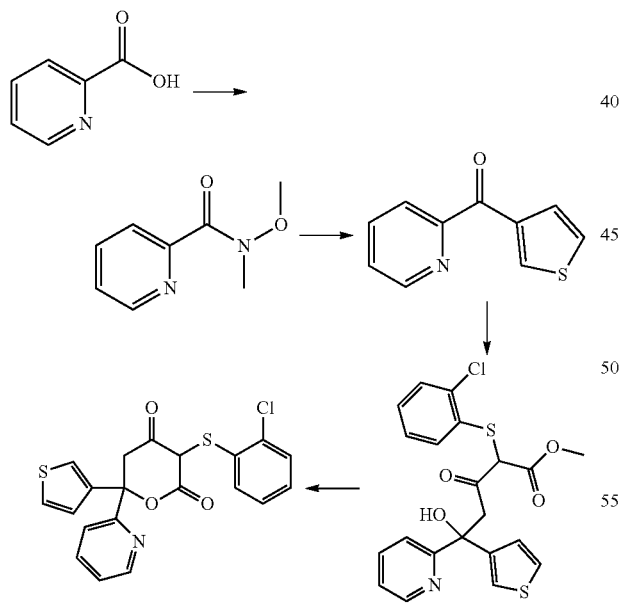

Step A: To a solution of 2-picolinic acid (5.0 g, 41 mmol) in DCM at 0° C. was added 1,1'-carbonyldiimidazole (8.6 g, 53 mmol). The mixture was stirred at 0° C. for 1.5 hr and trimethylamine (17 mL, 120 mmol) and N,O-dimethylhydroxylamine hydrochloride (5.2 g, 53 mmol) were added. The mixture was allowed to warm up to room temperature overnight and diluted with DCM (300 mL). The organic phase was washed with aqueous HCl 1M and aqueous saturated $NaHCO_3$, dried over $Na_2SO_4$ and concentrated under reduced pressure. The crude material was purified by flash column chromatography (silica gel, eluent: heptane/ethyl acetate=30% to 50 to 70%) to give N-methoxy-N-methylpicolinamide in 81% yield.

Step B: Pyridin-2-yl(thiophen-3-yl)methanone was prepared in 91% yield, according to Example 18, step B using N-methoxy-N-methylpicolinamide.

Step C: Methyl 2-((2-chlorophenyl)thio)-5-hydroxy-3-oxo-5-(pyridin-2-yl)-5-(thiophen-3-yl)pentanoate was prepared in 79% yield, according to Example 18, step C, using pyridin-2-yl(thiophen-3-yl)methanone.

Step D: 3-((2-Chlorophenyl)thio)-6-(pyridin-2-yl)-6-(thiophen-3-yl)dihydro-2H-pyran-2,4(3H)-dione was prepared in 61% yield, according to Example 18, step D.

$^1$H NMR (300 MHz): δ=8.40-8.38 (m, 1H), 7.65-7.57 (m, 2H), 7.22-7.13 (m, 3H), 7.09-6.95 (m, 2H), 6.71 (td, J=7.8, 1.5 Hz, 1H), 6.56 (td, J=7.8, 1.2 Hz, 1H), 5.71 (dd, J=7.8, 1.5 Hz, 1H), 3.86 (d, J=17.4 Hz, 1H), 3.45 (d, J=17.4 Hz, 1H).

Example 21—Preparation of 2-(5-bromopyridin-2-yl)-5-((2-chlorophenyl)thio)-6-oxo-2-(thiophen-3-yl)-3,6-dihydro-2H-pyran-4-yl methyl carbonate

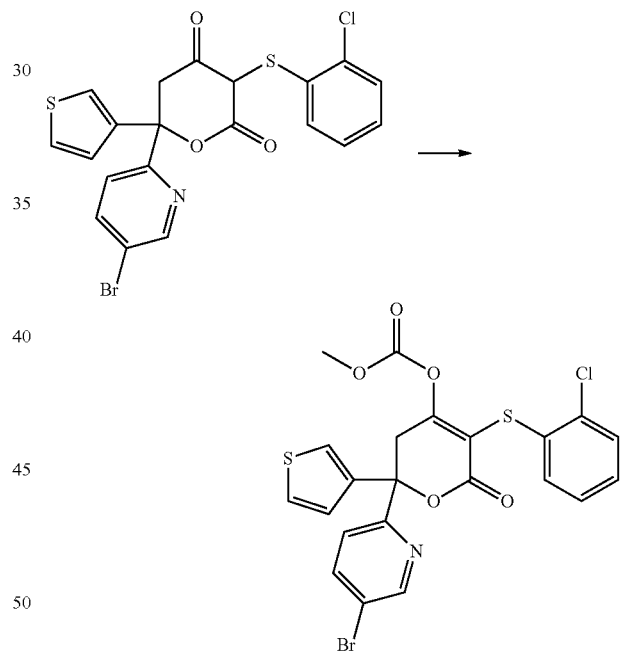

To a solution of 6-(5-bromopyridin-2-yl)-3-((2-chlorophenyl)thio)-6-(thiophen-3-yl)dihydro-2H-pyran-2,4(3H)-dione in DCM at 0° C. was added diisopropylamineethylamine. After 5 min at 0° C., methyl chloroformate was added and the reaction was stirred at 0° C. for 1.5 hr. The reaction was quenched by the addition of water (2 mL) and the aqueous phase was extracted with DCM (3×10 mL). The combined organic phases were dried with $Na_2SO_4$, filtered and concentrated under vacuo. The crude product was purified by flash chromatography on silica gel (eluent: heptane/ethyl acetate: 90/10 to 70/30) to give 2-(5-bromopyridin-2-yl)-5-((2-chlorophenyl)thio)-6-oxo-2-(thiophen-3-yl)-3,6-dihydro-2H-pyran-4-yl methyl carbonate in 24% yield.

¹H NMR (300 MHz): δ=8.62 (d, J=2.4 Hz, 1H), 7.80 (dd, J=8.7, 2.4 Hz, 1H), 7.54 (d, 0.1-8.7 Hz, 1H), 7.37-7.35 (m, 1H), 7.33-7.30 (m, 1H), 7.27-7.24 (m, 1H), 7.12-7.03 (m, 2H), 6.91-6.85 (m, 1H), 6.34 (dd, J=7.8, 1.5 Hz, 1H), 4.07 (d, J=18.0 Hz, 1H), 3.87 (s, 3H), 3.79 (d, J=18.0 Hz, 1H).

Example 22—Preparation of 6'-(cyclopentylmethoxy)-5-((2,4-dichlorophenyl)thio)-6-oxo-2-(thiophen-3-yl)-1,2,3,6-tetrahydro-[2,2'-bipyridin]-4-yl (2-methoxyethyl) carbonate -continued

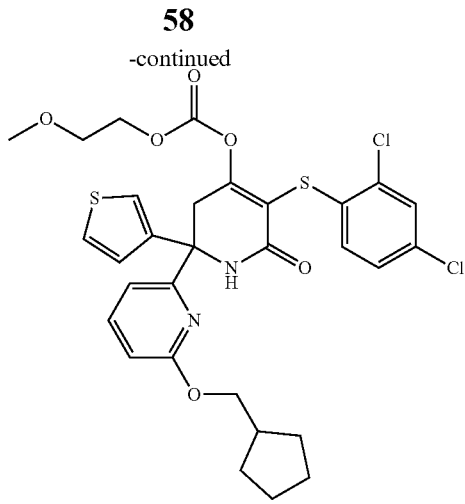

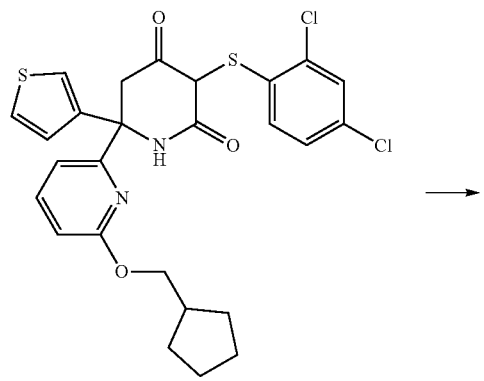

This compound was prepared according to Example 21 in 58% yield, using 6-(6-(cyclopentylmethoxy)pyridin-2-yl)-3-((2,4-dichlorophenyl)thio)-6-(thiophen-3-yl)piperidine-2,4-dione and 2-methoxyethyl chloroformate.

¹H NMR (300 MHz): δ=7.59 (dd, J=8.4, 7.2 Hz, 1H), 7.32 (dd, J=5.1, 3.0 Hz, 1H), 7.22-7.20 (m, 2H), 7.04 (dd, J=5.1, 1.5 Hz, 1H), 6.88 (dd, J=7.2, 0.6 Hz, 1H), 6.82 (dd, J=8.4, 2.4 Hz, 1H), 6.70 (dd, J=8.4, 0.6 Hz, 1H), 6.30 (d, J=8.4 Hz, 1H), 4.35-4.32 (m, 2H), 4.17-4.15 (m, 2H), 3.60 (d, J=17.1 Hz, 1H), 3.64-3.61 (m, 2H), 3.38 (s, 3H), 3.34 (d, J=17.1 Hz, 1H), 2.36-2.27 (m, 1H), 1.86-1.76 (m, 2H), 1.67-1.53 (m, 4H), 1.39-1.30 (m, 2H).

Example 23—Preparation of 3-((2-chlorophenyl)thio)-6-(2-morpholinopyrimidin-5-yl)-6-(thiophen-3-yl)dihydro-2H-pyran-2,4(3H)-dione

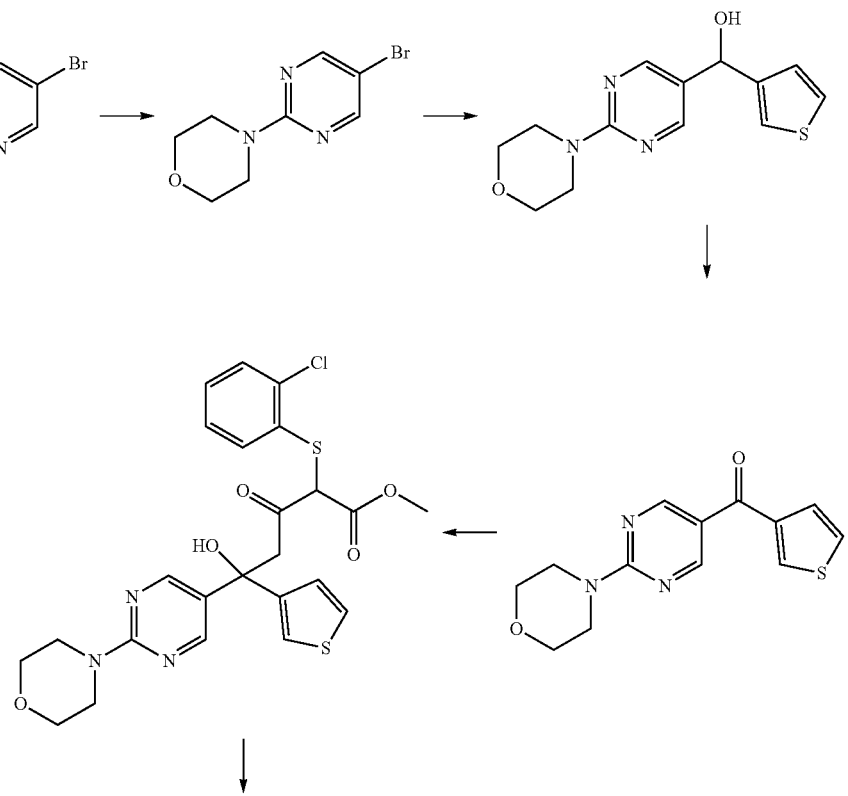

-continued

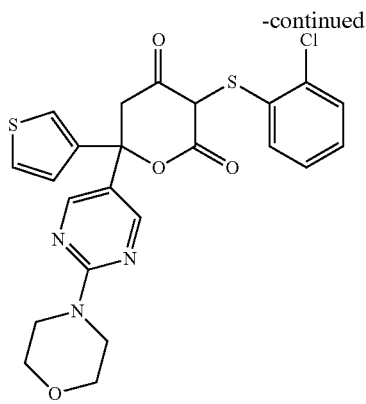

Step A: To a solution of morpholine (1.44 g, 16.5 mmol) in MeCN (70 mL) at room temperature was added $K_2CO_3$ (2.28 g, 16.5 mmol). After 1 hr at room temperature, 5-bromo-2-chloro-pyrimidine (2.90 g, 15 mmol) was added and the reaction mixture was stirred for 18 hr at reflux. The reaction was stopped by the addition of water (50 mL) and the phases were separated. The aqueous phase was extracted with ethyl acetate (2×50 mL) and the combined organic phases were dried over $Na_2SO_4$, filtered and concentrated under reduced pressure to give 4-(5-bromopyrimidin-2-yl)morpholine in quantitative yield.

Step B: To a solution of 4-(5-bromopyrimidin-2-yl)morpholine (3.6 g, 14.9 mmol) in THF (150 mL) at −78° C. was added TMEDA (3.33 mL, 22.4 mmol) and n-butyllithium (6.6 mL, 16.4 mmol) in hexanes. After 30 min at −78° C., thiophene-3-carbaldehyde (1.96 mL, 22.4 mmol) was added and the mixture was stirred for 2 hr between −78° C. and −70° C. The reaction was stopped by the addition of aqueous saturated $NH_4Cl$ and the aqueous phase was extracted with ethyl acetate (2×100 mL). The combined organic phases were washed with brine (50 mL), dried over $Na_2SO_4$, filtered and concentrated under reduced pressure. The crude material was purified by flash column chromatography (silica gel, eluent: heptane/ethyl acetate: 15 to 20 to 30 to 50 to 70%) to give (2-morpholinopyrimidin-5-yl)(thiophen-3-yl)methanol in 76% yield.

Step C: To a solution of (2-morpholinopyrimidin-5-yl)(thiophen-3-yl)methanol (310 mg, 1.12 mmol), tetrabutylammonium hydrogen sulfate (19.0 mg, 0.06 mmol), KBr (13.3 mg, 0.11 mmol) and TEMPO (1.8 mg, 0.01 mmol) in DCM (2 mL) at 0° C. was added NaOCl (1.08 g, 1.45 mmol) in water. The reaction mixture was stirred for 1.5 hr at 0° C. and stopped by the addition of aqueous saturated $Na_2S_2O_3$ (5 mL) and aqueous saturated $NaHCO_3$ (5 mL). The aqueous phase was extracted with DCM (3×10 mL) and the combined organic phases were dried over $Na_2SO_4$, filtered and concentrated under reduced pressure. The crude material was purified by flash column chromatography ($SiO_2$, heptane/EA: 20 to 30 to 50%) to give (2-morpholinopyrimidin-5-yl)(thiophen-3-yl)methanone in 78% yield. A mixture of methyl acetoacetate (1.3 mL, 12.1 mmol), 2-chloro-phenyl-disulfide (3.8 g, 13.3 mmol) and $K_2CO_3$ (5.0 g, 36 mmol) in DMF (36 mL) was stirred at 95° C. for 4 hr. The mixture was diluted with methyl tert-butyl ether (100 mL) and aqueous HCl 1M (50 mL). The organic phase was washed with brine (3×100 mL), dried over $Na_2SO_4$, filtered and concentrated under reduced pressure. The crude product was purified by flash chromatography (silica gel, eluent: heptane/ethyl acetate: 1% to 2 to 3 to 5%) to give methyl 2-((2-chlorophenyl)thio)-3-oxobutanoate in 39% yield.

Step D: To a solution of di-iso-propylamine (0.34 mL, 2.4 mmol) in THF (5 mL) at −78° C. was added n-butyllithium (0.88 mL, 2.2 mol) in hexanes slowly. After 10 min at −78° C., methyl 2-((2-chlorophenyl)thio)-3-oxobutanoate (285 mg, 1.1 mmol) in THF (2 mL) was added and stirring continued for 30 min at 0° C. (2-morpholinopyrimidin-5-yl)(thiophen-3-yl)methanone (230 mg, 0.84 mmol) in THF (2 mL) was added and the mixture was stirred for 1 hr at 0° C. The reaction was stopped by the addition of aqueous saturated $NH_4Cl$ (5 mL), the aqueous phase was extracted with ethyl acetate (3×10 mL) and the combined organic phases were dried over $Na_2SO_4$, filtered and concentrated under reduced pressure. The crude material was purified by flash column chromatography (silica gel, eluent: DCM to 1% MeOH to 2 to 4%) to give methyl 2-((2-chlorophenyl)thio)-5-hydroxy-5-(2-morpholinopyrimidin-5-yl)-3-oxo-5-(thiophen-3-yl)pentanoate in 98% yield.

Step E: A solution of methyl 2-((2-chlorophenyl)thio)-5-hydroxy-5-(2-morpholinopyrimidin-5-yl)-3-oxo-5-(thiophen-3-yl)pentanoate (439 mg, 0.82 mmol) and $K_2CO_3$ (340 mg, 2.5 mmol) in methanol (4 mL) was stirred at reflux for 5 hr. The mixture was concentrated under reduced pressure and diluted in water (5 mL) and aqueous HCl 1M (5 mL). The aqueous phase was extracted with ethyl acetate (3×10 mL) and the combined organic phases were dried over $Na_2SO_4$, filtered and concentrated under reduced pressure. The crude material was purified by flash column chromatography (silica gel, eluent: DCM to 1% MeOH to 2 to 4%) to give 3-((2-chlorophenyl)thio)-6-(2-morpholinopyrimidin-5-yl)-6-(thiophen-3-yl)dihydro-2H-pyran-2,4(3H)-dione in 43% yield.

$^1$HNMR (300 MHz): δ=8.31 (s, 2H), 7.43-7.40 (m, 1H), 7.34 (dd, J=2.7, 1.5 Hz, 1H), 7.29-7.26 (m, 1H), 7.11 (dd, J=5.0, 1.4 Hz, 1H), 7.05 (td, J=7.7, 1.5 Hz, 1H), 6.88 (td, J=7.7, 1.5 Hz, 1H), 6.21 (dd, J=7.9, 1.4 Hz, 1H), 3.98-3.94 (m, 1H), 3.83-3.73 (m, 8H), 3.47 (s, 2H).

Example 24—Preparation of 3-((2-chlorophenyl)thio)-6-(4-morpholinophenyl)-6-(thiophen-3-yl)piperidine-2,4-dione (Example 44 in WO 2015/142903)

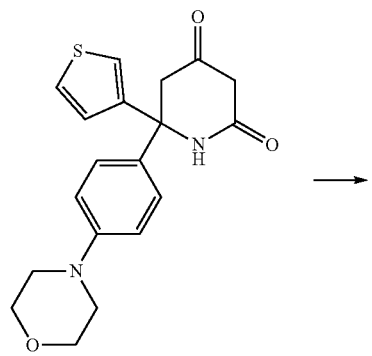

→

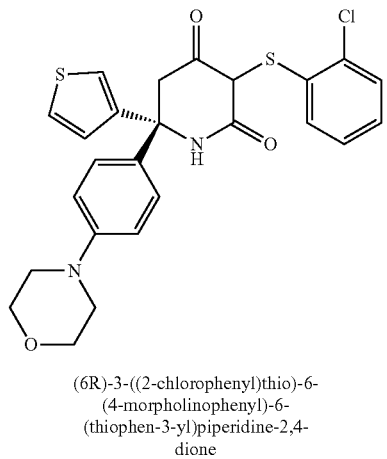

(6R)-3-((2-chlorophenyl)thio)-6-(4-morpholinophenyl)-6-(thiophen-3-yl)piperidine-2,4-dione

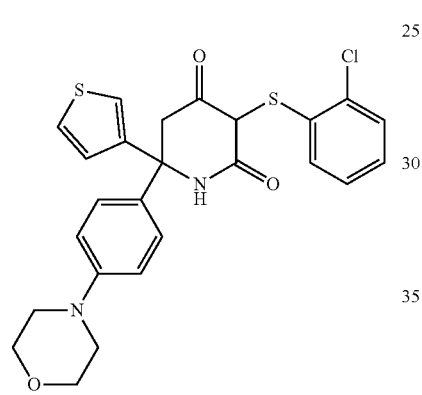

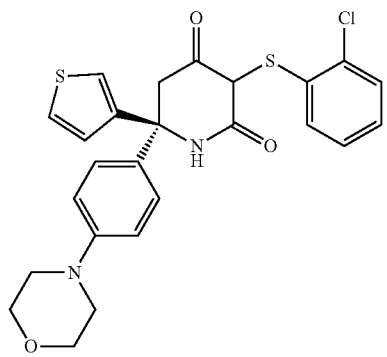

(6S)-3-((2-chlorophenyl)thio)-6-(4-morpholinophenyl)-6-(thiophen-3-yl)piperidine-2,4-dione A solution of 6-(4-morpholinophenyl)-6-(thiophen-3-yl)piperidine-2,4-dione (50 mg, 0.14 mmol), 1,2-bis(2-chlorophenyl)disulfane (48 mg, 0.17 mmol) and $K_2CO_3$ (58 mg, 0.42 mmol) in methanol (1.5 mL) was stirred at reflux for 2 hr. The mixture was concentrated under reduced pressure and diluted in water (3 mL) and aqueous HCl 1M (1 mL). The aqueous phase was extracted with ethyl acetate (3×5 mL) and the combined organic phases were dried over $Na_2SO_4$, filtered and concentrated under reduced pressure. The crude material was purified by flash column chromatography ($SiO_2$, heptane/ethyl acetate: 2/1 to 1/1 to 1/3) to give 3-((2-chlorophenyl)thio)-6-(4-morpholinophenyl)-6-(thiophen-3-yl)piperidine-2,4-dione in 61% yield. Analytical data were identical to the literature (ACS Med. Chem. Lett. 7: 896-901, 2016).

The compound of Example 24 was tested in the assays as the racemate and additionally as single enantiomers. It was possible to acquire the individual enantiomers by chiral preparative HPLC of the final product using an ethanol/acetonitrile/diethylamine (90/10/0.1) solvent system. Analysis of the enantiomers by analytical HPLC on a ChiralPak IC column using the same solvent system revealed that the enantiomers had been isolated in 100% (Enantiomer 1: $R_t$=5.5 min) and 97% (Enantiomer 2: $R_t$=7.5 min) e.e.

Example 25—Preparation of 3-((2-chlorophenyl)thio)-6-(6-(cyclopentylmethoxy)pyridin-2-yl)-6-(thiophen-3-yl)piperidine-2,4-dione (Example 194 in WO 2015/142903)

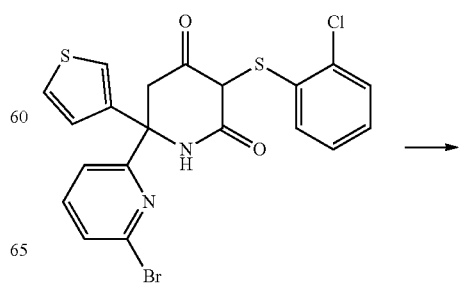

→

-continued

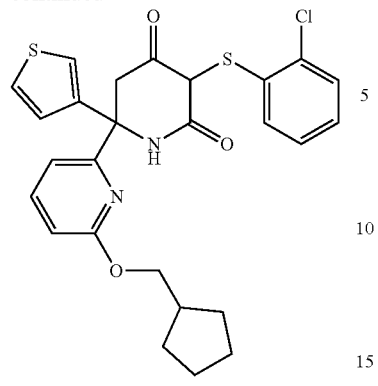

To a suspension of NaH (61 mg, 1.5 mmol) in THF (3 mL) at 0° C. was added CpMeOH (0.16 mL, 1.5 mmol). After 30 min at 0° C., 6-(6-bromopyridin-2-yl)-3-((2-chlorophenyl)thio)-6-(thiophen-3-yl)piperidine-2,4-dione (150 mg, 0.30 mmol) was added and the reaction mixture was stirred for 18 hr at reflux. The reaction was stopped by the addition of water (10 mL) and HCl 1M (3 mL). The aqueous phase was extracted with ethyl acetate (3×10 mL) and the combined organic phases were dried over $Na_2SO_4$, filtered and concentrated under reduced pressure. The crude material was purified by flash column chromatography (silica gel, eluent: heptane/ethyl acetate: 8/2 to 7/3 to 1/1) to give 3-((2-chlorophenyl)thio)-6-(6-(cyclopentylmethoxy)pyridin-2-yl)-6-(thiophen-3-yl)piperidine-2,4-dione in 62% yield.

$^1$H NMR (400 MHz, MeOH-d4): δ=7.70 (t, J=7.8 Hz, 1H), 7.43 (dd, J=5.0, 3.0 Hz, 1H), 7.28 (br s, 1H), 7.22 (d, J=7.9 HZ, 1H), 7.15-7.12 (m, 2H), 6.94 (t, J=7.8 Hz, 1H), 6.77-6.73 (m, 2H), 5.98 (d, J=8.0 Hz, 1H), 4.22 (m, 2H9, 3.91 (d, J=16.4 Hz, 1H), 3.45 (d, J=16.4 Hz, 1H), 3.45 (s, 1H), 2.35-2.28 (m, 1H), 1.82-1.73 (m, 2H), 1.64-1.51 (m, 4H), 1.38-1.30 (m, 2H).

Example 26—Preparation of 5-((2,5-dichlorophenyl)thio)-2-(4-morpholinophenyl)-6-oxo-2-(thiophen-3-yl)-1,2,3,6-tetrahydropyridin-4-yl isobutyl carbonate

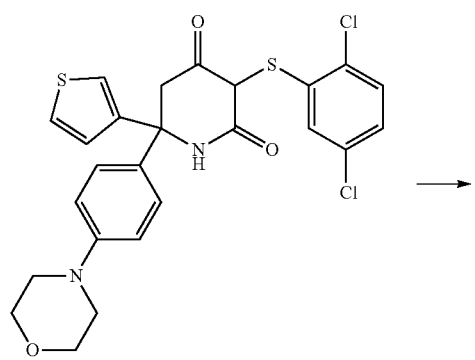

-continued

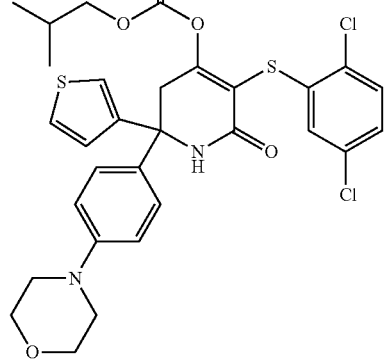

This compound was prepared in 60% yield according to the method in Example 11 using 3-((2,5-dichlorophenyl)thio)-6-(4-morpholinophenyl)-6-(thiophen-3-yl)piperidine-2,4-dione and iso-butyl chloroformate.

$^1$H NMR (300 MHz, $CDCl_3$): δ=7.37 (dd, J=5.1, 3.0 Hz, 1H), 7.23 (d, J=8.9 Hz, 2H), 7.19-7.17 (m, 1H), 7.18 (d, J=8.6 Hz, 2H), 6.97 (dd, J=2.7, 1.5 Hz, 1H), 6.95 (d, J=1.8 Hz, 1H), 6.90 (d, J=8.8 Hz, 2H), 6.53 (d, J=2.4 Hz, 1H), 6.39 (br s, 1H), 4.96 (d, J=Hz, 2H), 3.87-3.84 (m, 4H), 3.55 (s, 2H), 3.19-3.16 (m, 4H), 1.97 (hept, J=6.8 Hz, 1H), 1.26 (t, J=7.1 Hz, 2H), 0.92 (d, J=6.8 Hz, 6H).

Example 27—Preparation of 5-((2,5-dichlorophenyl)thio)-2-(4-morpholinophenyl)-6-oxo-2-(thiophen-3-yl)-1,2,3,6-tetrahydropyridin-4-yl acetate

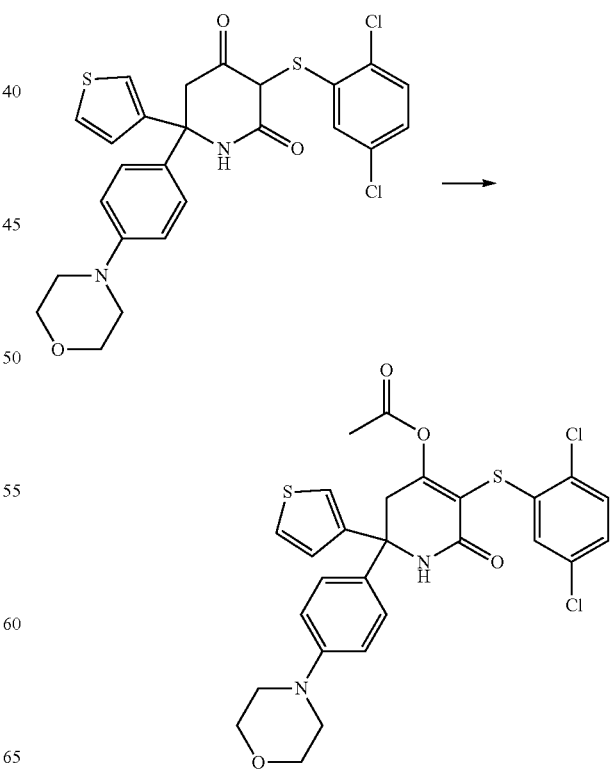

This compound was prepared in 42% yield according to the method in Example 11 using 3-((2,5-dichlorophenyl)thio)-6-(4-morpholinophenyl)-6-(thiophen-3-yl)piperidine-2,4-dione and acetyl chloride.

¹H NMR (300 MHz, CDCl₃): δ=7.37 (dd, J=5.0, 3.0 Hz, 1H), 7.23 (d, J=8.9 Hz, 2H), 7.17 (dd, J=3.0, 1.4 Hz, 1H), 7.17 (d, J=8.5 Hz, 1H), 6.99-6.97 (m, 1H), 6.97-6.95 (m, 1H), 6.90 (d, J=8.9 Hz, 2H), 6.52 (d, J=2.4 Hz, 1H), 6.45 (br s, 1H), 3.87-3.84 (m, 4H), 3.51 (s, 2H), 3.19-3.16 (m, 4H), 2.16 (s, 3H).

Example 28—Preparation of 5-((2,5-dichlorophenyl)thio)-2-(4-morpholinophenyl)-6-oxo-2-(thiophen-3-yl)-1,2,3,6-tetrahydropyridin-4-yl pivalate

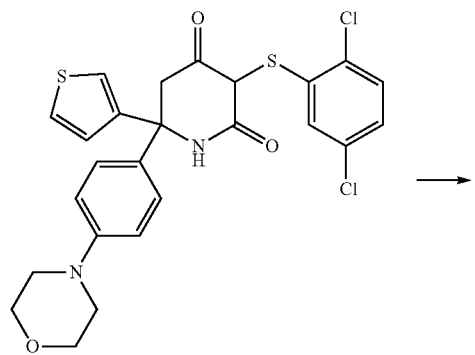

This compound was prepared in 48% yield according to the method in Example 11 using 3-((2,5-dichlorophenyl)thio)-6-(4-morpholinophenyl)-6-(thiophen-3-yl)piperidine-2,4-dione and pivaloyl chloride.

¹H NMR (300 MHz, CDCl₃): δ=7.37 (dd, J=5.1, 3.1 Hz, 1H), 7.24 (d, J=9.0 Hz, 2H), 7.19 (dd, J=3.0, 1.2 Hz, 1H), 7.16 (d, J=8.6 Hz, 1H), 6.99-6.93 (m, 2H), 6.89 (d, J=8.9 Hz, 2H), 6.45 (d, J=2.4 Hz, 1H), 6.40 (br s, 1H), 3.87-3.83 (m, 4H), 3.52 (s, 2H), 3.19-3.16 (m, 4H), 1.17 (s, 9H).

Example 29—Preparation of 3-((2,4-dichlorophenyl)thio)-6-(4-morpholinophenyl)-6-(thiophen-3-yl)piperidine-2,4-dione

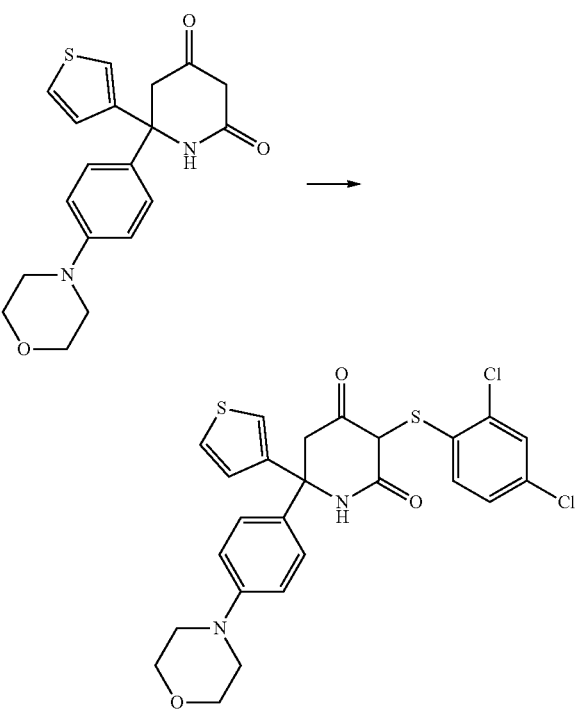

This compound was prepared according to the method in Example 2, using 6-(4-morpholinophenyl)-6-(thiophen-3-yl)piperidine-2,4-dione and 1,2-bis(2,4-dichlorophenyl)disulfane, in 50% yield.

¹H NMR (MeOD-d4, 300 MHz): δ=7.49 (dd, J=5.0, 3.0 Hz, 1H), 7.33 (d, J=8.8 Hz, 21-), 7.26-7.22 (m, 2H), 7.14 (d, J=5.2 Hz, 1H), 6.98 (d, J=8.9 Hz, 2H), 6.72 (dd, J=7.6, 2.0 Hz, 1H), 5.84 (d, J=8.7 Hz), 3.86-3.83 (m, 4H), 3.43 (s, 2H), 3.20-3.17 (m, 4H).

Example 30—Preparation of 5-((2,4-dichlorophenyl)thio)-2-(4-morpholinophenyl)-6-oxo-2-(thiophen-3-yl)-1,2,3,6-tetrahydropyridin-4-yl (2-methoxyethyl) carbonate

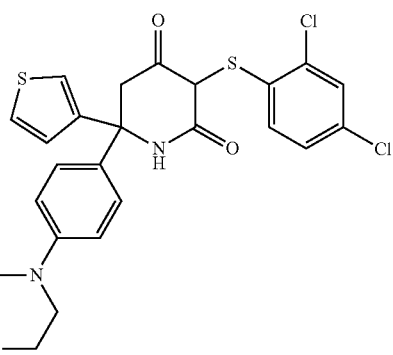

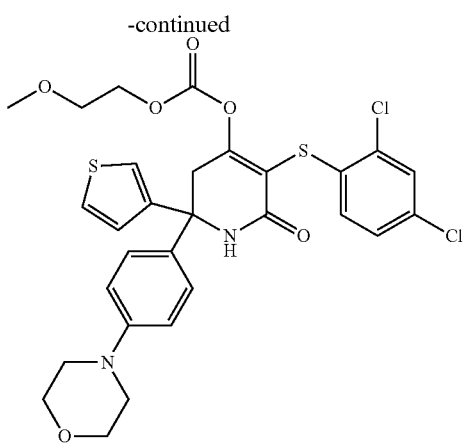

This compound was prepared in 47% yield according to the method in Example 11 using 3-((2,4-dichlorophenyl)thio)-6-(4-morpholinophenyl)-6-(thiophen-3-yl)piperidine-2,4-dione and 2-(methoxy)ethyl chloroformate.

$^1$H NMR (300 MHz, CDCl$_3$): δ=7.39 (dd, J=5.0, 3.0 Hz, 1H), 7.24 (d, J=2.2 Hz, 1H), 7.20 (d, J=8.9 Hz, 2H), 7.18 (dd, J=3.0, 1.5 Hz, 1H), 6.98 (d, J=5.0, 1.5 Hz, 1H), 6.87 (d, J=8.9 Hz, 2H), 6.77 (d, J=8.5, 2.2 Hz, 1H), 6.47 (br s, 1H), 6.16 (d, J=8.5 Hz, 1H), 4.35-4.31 (m, 2H), 3.89-3.86 (m, 4H), 3.63-3.60 (m, 2H), 3.52 (br s, 2H), 3.37 (s, 3H), 3.20-3.17 (m, 4H).

Example 31—Preparation of 5-((2,5-dichlorophenyl)thio)-2-(4-morpholinophenyl)-6-oxo-2-(thiophen-3-yl)-1,2,3,6-tetrahydropyridin-4-yl isonicotinate

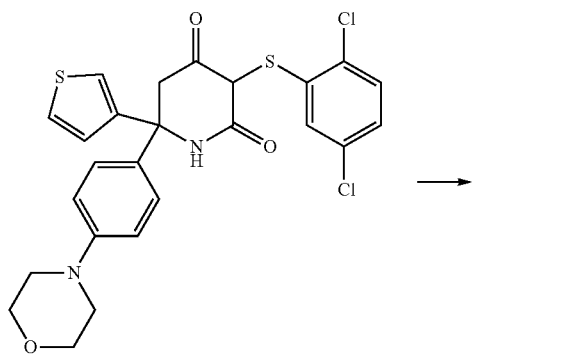

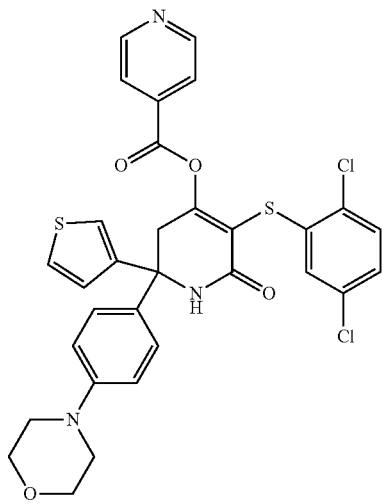

This compound was prepared in 42% yield according to the method in Example 11 using 3-((2,5-dichlorophenyl)thio)-6-(4-morpholinophenyl)-6-(thiophen-3-yl)piperidine-2,4-dione and isonicotinoyl chloride hydrochloride.

$^1$H NMR (300 MHz, CDCl$_3$): δ=8.79 (br s, 2H), 7.73 (d, J=5.0 Hz, 2H), 7.41-7.38 (m, 1H), 7.29 (br s, 1H), 7.22 (br s, 1H), 7.10 (d, J=8.5 Hz, 1H), 7.01-6.94 (m, 4H), 6.64 (d, J=2.3 Hz, 2H), 3.90-3.87 (m, 4H), 3.67 (s, 2H), 3.22-3.19 (m, 4H).

Example 32—Preparation of 5-((2-chloro-4-fluorophenyl)thio)-2-(4-morpholinophenyl)-6-oxo-2-(thiophen-3-yl)-1,2,3,6-tetrahydropyridin-4-yl iso-butyl carbonate

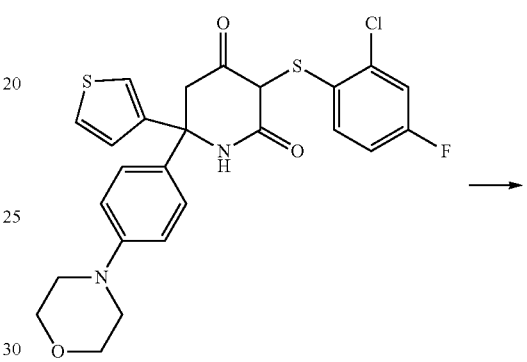

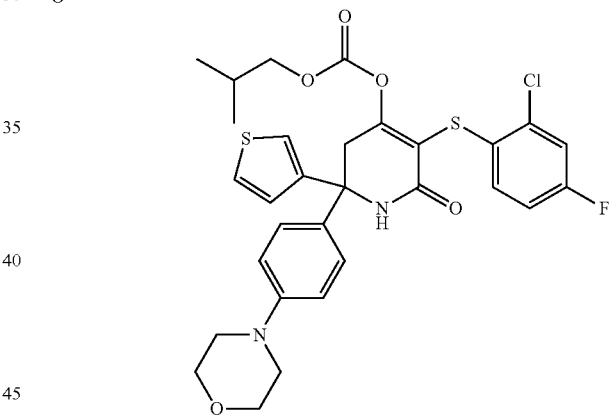

This compound was prepared in 76% yield according to the method in Example 11 using 3-((2-chloro-4-fluorophenyl)thio)-6-(4-morpholinophenyl)-6-(thiophen-3-yl)piperidine-2,4-dione and iso-butyl chloroformate. In this instance 3-((2-chloro-4-fluorophenyl)thio)-6-(4-morpholinophenyl)-6-(thiophen-3-yl)piperidine-2,4-dione was prepared according to a modified method in which Step B in the synthesis of 6-(4-morpholinophenyl)-6-(thiophen-3-yl)piperidine-2,4-dione utilised (S)-t-butylsulfinimide in place of the racemate. Step C then proceeded with a degree of diastereocontrol, with analysis of the diastereomers by $^1$H NMR revealing a diastereomeric ratio of 85:15. This ratio will be represented in the enantiomeric ratio of the final product.

$^1$H NMR (400 MHz, CDCl$_3$): δ=7.36 (dd, J=5.0, 3.0 Hz, 1H), 7.19 (d, J=8.9 Hz, 2H), 7.18-7.16 (m, 1H), 6.99 (dd, J=8.4, 2.7 Hz, 1H), 6.95 (dd, J=5.0, 1.5 Hz, 1H), 6.87 (d, J=8.9 Hz, 2H), 6.62-6.55 (m, 2H), 6.42 (dd, J=8.8, 5.8 Hz, 1H), 3.96 (d, J=7.7 Hz, 2H), 3.88-3.85 (m, 4H), 3.49 (br s, 2H), 3.19-3.16 (m, 4H), 1.96 (hept, J=6.7 Hz, 2H), 1.25 (t, J=7.1 Hz, 2H), 0.93 (d, J=6.7 Hz, 6H).

Example 33—Preparation of 5-((2-chloro-4-fluorophenyl)thio)-2-(4-morpholinophenyl)-6-oxo-2-(thiophen-3-yl)-1,2,3,6-tetrahydropyridin-4-yl (2-methoxyethyl) carbonate

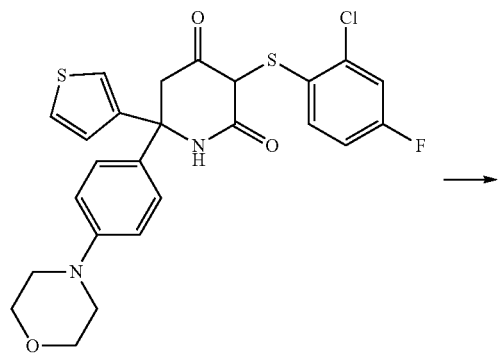

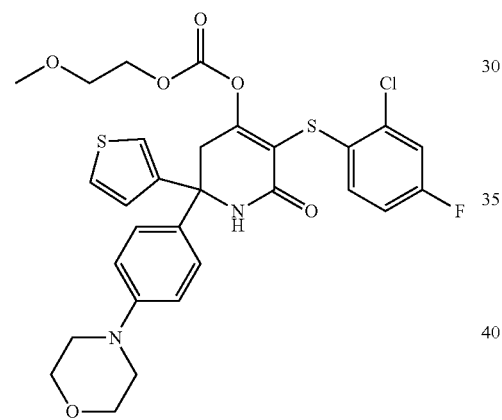

This compound was prepared in 40% yield according to the method in Example 11 using 3-((2-chloro-4-fluorophenyl)thio)-6-(4-morpholinophenyl)-6-(thiophen-3-yl)piperidine-2,4-dione and 2-methoxyethyl chloroformate. In this instance 3-((2-chloro-4-fluorophenyl)thio)-6-(4-morpholinophenyl)-6-(thiophen-3-yl)piperidine-2,4-dione was prepared according to a modified method in which Step B in the synthesis of 6-(4-morpholinophenyl)-6-(thiophen-3-yl)piperidine-2,4-dione utilised (S)-t-butylsulfinimide in place of the racemate. Step C then proceeded with a degree of diastereocontrol, with analysis of the diastereomers by $^1$H NMR revealing a diastereomeric ratio of 85:15. This ratio will be represented in the enantiomeric ratio of the final product.

$^1$H NMR (400 MHz, CDCl$_3$): δ=7.38-7.36 (m, 1H), 7.20 (d, J=8.6 Hz, 2H), 7.17 (m, 1H), 7.00 (dd, J=8.3, 2.6 Hz, 1H), 6.96 (d, J=5.0 Hz, 1H), 6.92-6.88 (m, 2H), 6.58 (td, J=8.4, 2.6 Hz, 1H), 6.39 (dd, J=8.7, 5.8 Hz, 1H), 4.34-4.32 (m, 2H), 3.89 (m, 4H), 3.63-3.61 (m, 2H), 3.50 (d, J=2.6 Hz, 2H), 3.38 (s, 3H), 3.20-3.18 (m, 4H).

Example 34—Preparation of 6'-(cyclopentylmethoxy)-5-((2,5-dichlorophenyl)thio)-6-oxo-2-(thiophen-3-yl)-1,2,3,6-tetrahydro-[2,2'-bipyridin]-4-yl (2-methoxyethyl) carbonate

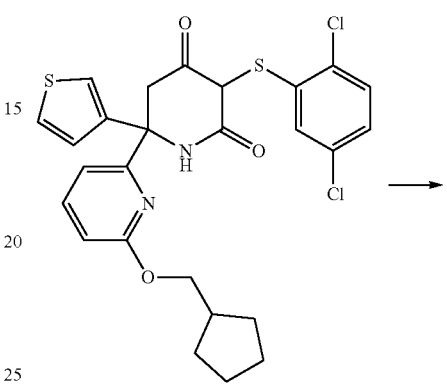

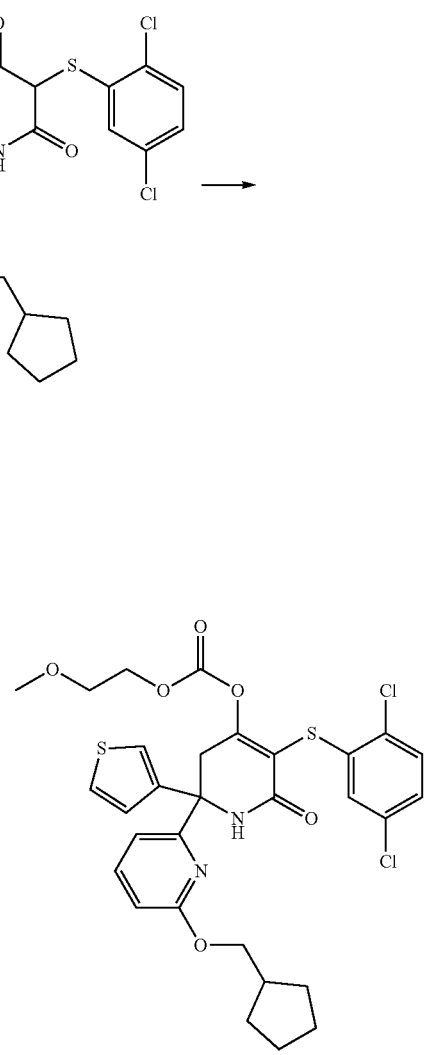

This compound was prepared in 63% yield according to the method in Example 11 using 6-(6-(cyclopentylmethoxy)pyridin-2-yl)-3-((2,5-dichlorophenyl)thio)-6-(thiophen-3-yl)piperidine-2,4-dione and 2-(methoxy)ethyl chloroformate.

$^1$H NMR (300 MHz, CDCl$_3$): δ=7.60 (dd, J=8.2, 7.5 Hz, 1H), 7.30 (dd, J=5.0, 3.0 Hz, 1H), 7.20 (dd, J=3.0, 1.5 Hz, 1H), 7.17 (d, J=8.5 Hz, 2H), 7.01 (dd, J=5.0, 1.4 Hz, 1H), 6.98 (dd, J=8.5, 1.4 Hz, 1H), 6.91 (d, J=7.3 Hz, 1H), 6.68 (d, J=8.2 Hz, 1H), 6.58 (d, J=2.4 Hz, 1H), 4.35-4.32 (m, 2H), 4.16 (d, J=7.0 Hz, 2H), 3.86 (d, J 17.0 Hz, 1H), 3.64-3.58 (m, 3H), 3.37 (s, 3H), 2.35-2.26 (m, 1H), 1.86-1.74 (m, 2H), 1.65-1.56 (m, 4H), 1.41-1.31 (m, 2H).

Example 35—Preparation of 5-((2-chlorophenyl)thio)-2-(2-morpholinopyrimidin-5-yl)-6-oxo-2-(thiophen-3-yl)-3,6-dihydro-2H-pyran-4-yl (2-methoxyethyl) carbonate

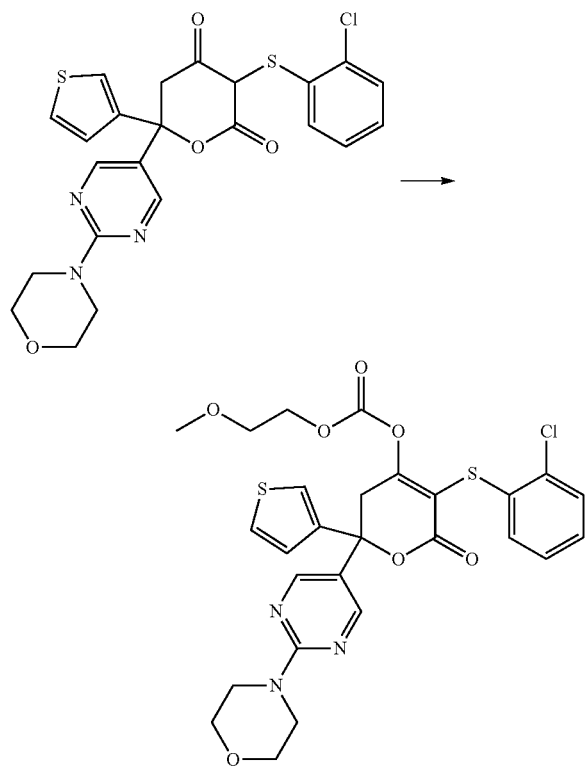

This compound was prepared in 38% yield according to Example 11 using 3-((2-chlorophenyl)thio)-6-(2-morpholinopyrimidin-5-yl)-6-(thiophen-3-yl)dihydro-2H-pyran-2,4(3H)-dione and 2-(methoxy)ethyl chloroformate.

$^1$H NMR (300 MHz, CDCl$_3$): δ=8.29 (s, 2H), 7.44-7.39 (m, 2H), 7.28-7.22 (m, 1H), 7.09 (dd, J=4.43, 2.17 Hz, 1H), 7.04 (td, J=7.66, 1.54 Hz, 1H), 6.87 (td, J=7.63, 1.44 Hz, 1H), 6.29 (dd, J=7.93, 1.52 Hz, 1H), 4.39-4.33 (m, 2H), 3.90-3.71 (m, 10H), 3.66-3.59 (m, 5H).

Example 36—Coupled Diaphorase Assay

The inhibitory properties of the compounds were investigated using a coupled enzyme assay that links the lactate dehydrogenase (LDH) reaction to the production of fluorescent resorutin by diaphorase.

Human lactate dehydrogenases (LDH) catalyze the reversible interconversion between pyruvate and lactate. LDH is capable of catalyzing both the forward (pyruvate to lactate) and the reverse (lactate to pyruvate) reaction, using either NADH or NAD$^+$ as a cofactor. The reaction proceeds in either direction dependent on various factors, such as substrate availability, the presence of necessary cofactors, temperature and pH. Different isoforms (LDH A, B, and C) of the enzyme favor different reaction directions—LDHA prefers the conversion from pyruvate to lactate, whereas LDHB preferentially oxidizes lactate to pyruvate.

The coupled assay relies on the oxidation of NAD$^+$ to NADH throughout the conversion of lactate to pyruvate by LDH (isoforms A, B and C). The produced NADH serves as cofactor in the diaphorase reaction, which reduces non-fluorescent resazurin to fluorescent resorufin. Therefore, the assay indirectly monitors the rate of pyruvate production. Although the consumption of NADH can be directly monitored due to the intrinsic fluorescence of the molecule (excitation: 340 nm, emission: 460 nm) there are problems linked to the direct readout method. It has been shown that many compounds in chemical libraries interfere with the assay due to fluorescent properties similar to NADH. Shifting the assay to longer wavelengths by coupling the LDH reaction to the conversion of resazurin to fluorescent resorufin by diaphorase reduces this compound interference. The assay direction was thus chosen to provide a robust and reliable assay.

Applying the LDHA reaction in the preferred direction for the conversion of pyruvate to lactate under oxidation of NADH to NAD$^+$ would necessitate running the LDHA reaction to about 80% completion and adding the diaphorase assay reagents afterwards in order to avoid enzyme competition for NADH. As a result, such a method would be expected to be more prone to errors, since too high conversion rates will lead to extenuation of the IC$_{50}$ values obtained (Davis et al., ASSAY and Drug Dev. Tech. 14 (3): 175-179, 2016). When not running the assay in the preferred direction for LDHA, more conservative IC$_{50}$ values would be expected to be obtained compared to earlier published results for other LDHA inhibitor compounds. Therefore, actual IC$_{50}$ values could thus be expected to be lower.

For the determination of IC$_{50}$ values a coupled diaphorase assay was adopted from Bembenek et al. (A Fluorescence-Based Coupling Reaction for Monitoring the Activity of Recombinant Human NAD Synthetase. ASSAY and Drug Development Technologies, 2005. 3(5): 533-541). Compounds were tested in duplicates using 2-fold, 3-fold or 4-fold serial dilutions including 11 individual concentrations, starting from 5000 µM to 30 µM. A no-substrate control representing 100% inhibition or oxamate-inhibition controls (28.7 mM final oxamate concentration in assay) and a control containing the complete substrate solution as well as DMSO representing the fully uninhibited reaction were added. Oxamate is a well characterized inhibitor of LDH that inhibits LDH enzyme activity in the mM range in vitro with high specificity (Papacostantinou el al., J. Biol. Chem. 236: 278-284, 1961). The controls allowed for the calculation of the percentage inhibition for each data point. The assay buffer consisted of 50 mM HEPES pH 7.4, 5 mM MgCl$_2$ and 0.05% pluronic acid F-127. Enzyme solution leading to final concentrations of 4-7 nM LDHA or 6 nM LDHB, as well as 0.2 U/ml diaphorase in the reaction well was dispensed into 384-well plates (Greiner bio-one) using a CyBi®-SELMA robotic pipettor. Compound dilutions and the enzyme were incubated for at least 20 min at room temperature. Thereafter, the substrate solution was added (final concentrations: 500 µM lactate, 150 µM NAD$^+$, 3 µM resazurin) and the reaction was allowed to progress for 10 min. The reaction was quenched by the addition of a stop solution (final concentrations: 20 mM EDTA, 400 mM NaCl, 40 mM pyruvate). Fluorescence was read out after 5 min of incubation at an excitation wavelength of 560 nm and an emission wavelength of 590 nm on a Perkin Elmer Victor X plate reader.

A counter screen was employed to remove false positives that only inhibit the diaphorase reaction. Therefore, an enzyme solution only containing diaphorase was incubated with the compound dilution series. A substrate solution leading to final concentrations of 15 µM NADH and 3 µM resazurin was added and the assay was performed as described above. A substrate solution containing only resazurin was used as 100% inhibition control.

Fluorescence data was normalized to DMSO and inhibition controls resulting in percentage inhibition for every compound concentration. Dose response curves were fitted in KaleidaGraph (www.synergy.com) or Dotmatics software package (www.dotmatics.com) using a standard 4-parameter fit (Levenberg-Marquardt fitting procedure), resulting in $IC_{50}$ values for the test compounds. Results are presented in Table 1.

TABLE 1

| Example No. | Compound | $IC_{50}$ LDHA [μM] | $IC_{50}$ LDHB [μM] |
|---|---|---|---|
| 1 | *(structure)* | − | --- |
| 2 | *(structure)* | − | --- |
| 3 | *(structure)* | + | --- |
| 4 | *(structure)* | − | --- |

TABLE 1-continued

| Example No. | Compound | IC$_{50}$ LDHA [µM] | IC$_{50}$ LDHB [µM] |
|---|---|---|---|
| 5 | | ++ | − |
| 6 | | --- | --- |
| 7 | | − | --- |
| 8 | | ++ | ++ |

TABLE 1-continued

| Example No. | Compound | IC$_{50}$ LDHA [μM] | IC$_{50}$ LDHB [μM] |
|---|---|---|---|
| 9 | | + | --- |
| 10 | | ++ | ++ |
| 11 | | --- | --- |

TABLE 1-continued

| Example No. | Compound | IC$_{50}$ LDHA [μM] | IC$_{50}$ LDHB [μM] |
|---|---|---|---|
| 12 | | --- | --- |
| 13 | | --- | --- |
| 14 | | -- | -- |

TABLE 1-continued

| Example No. | Compound | IC$_{50}$ LDHA [μM] | IC$_{50}$ LDHB [μM] |
|---|---|---|---|
| 15 | | -- | --- |
| 16 | | --- | --- |
| 17 | | - | - |
| 18 | | + | - |

TABLE 1-continued

| Example No. | Compound | IC$_{50}$ LDHA [μM] | IC$_{50}$ LDHB [μM] |
|---|---|---|---|
| 19 | | + | − |
| 20 | | + | + |
| 21 | | − | − |
| 22 | | --- | --- |

TABLE 1-continued

| Example No. | Compound | IC$_{50}$ LDHA [μM] | IC$_{50}$ LDHB [μM] |
|---|---|---|---|
| 23 | | + | + |
| 26 | | -- | --- |
| 27 | | - | -- |

TABLE 1-continued
| Example No. | Compound | IC$_{50}$ LDHA [μM] | IC$_{50}$ LDHB [μM] |
|---|---|---|---|
| 28 | 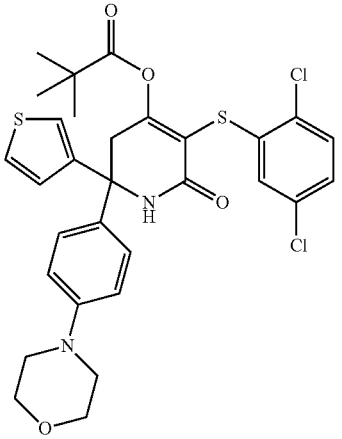 [SMILES: CC(C)(C)C(=O)OC1=C(Sc2cc(Cl)ccc2Cl)C(=O)NC(c2ccc(N3CCOCC3)cc2)(c2ccsc2)C1] | – | -- |
| 29 | 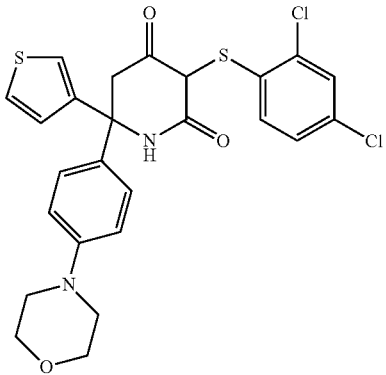 [SMILES: O=C1CC(c2ccc(N3CCOCC3)cc2)(c2ccsc2)NC(=O)C1Sc1ccc(Cl)cc1Cl] | -- | --- |
| 30 | 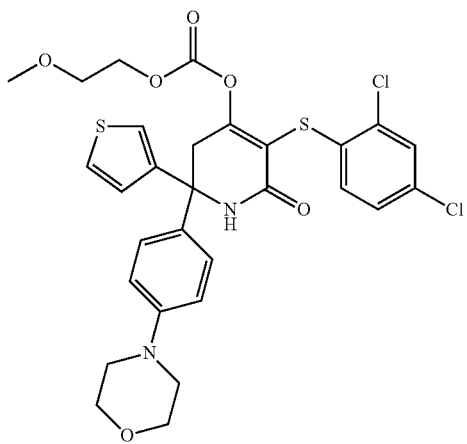 [SMILES: COCCOC(=O)OC1=C(Sc2ccc(Cl)cc2Cl)C(=O)NC(c2ccc(N3CCOCC3)cc2)(c2ccsc2)C1] | --- | --- |

TABLE 1-continued

| Example No. | Compound | IC$_{50}$ LDHA [μM] | IC$_{50}$ LDHB [μM] |
|---|---|---|---|
| 31 | | + | + |
| 32 | | --- | --- |
| 33 | | + | --- |

TABLE 1-continued
| Example No. | Compound | IC$_{50}$ LDHA [μM] | IC$_{50}$ LDHB [μM] |
|---|---|---|---|
| 34 | 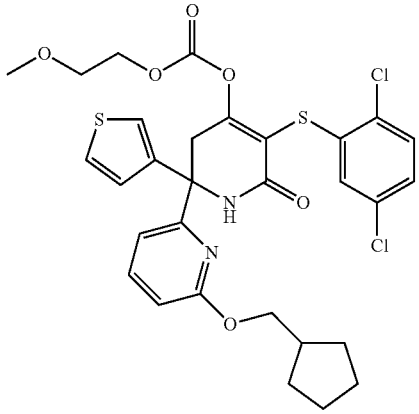 [SMILES: COCCOC(=O)OC1=C(Sc2cc(Cl)ccc2Cl)C(=O)NC(c2ccsc2)(c2cccc(OCC3CCCC3)n2)C1] | --- | --- |
| 35 | 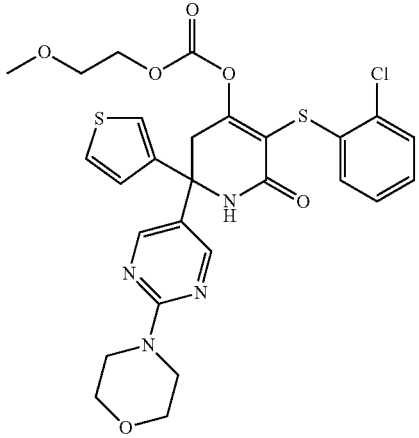 [SMILES: COCCOC(=O)OC1=C(Sc2ccccc2Cl)C(=O)NC(c2cnc(N3CCOCC3)nc2)(c2ccsc2)C1] | – | – |
| 10 Enantiomer 1 | 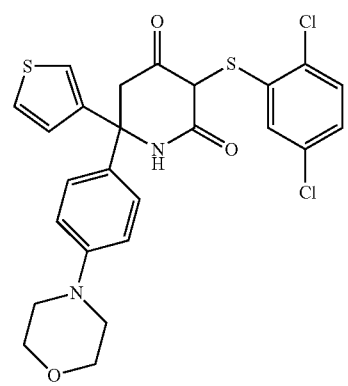 [SMILES: O=C1CC(c2ccc(N3CCOCC3)cc2)(c2ccsc2)NC(=O)C1Sc1cc(Cl)ccc1Cl] | + | – |

TABLE 1-continued

| Example No. | Compound | IC$_{50}$ LDHA [μM] | IC$_{50}$ LDHB [μM] |
|---|---|---|---|
| 10 Enantiomer 2 | | − | −−− |
| 17 Enantiomer 1 | | − | −− |
| 17 Enantiomer 2 | | + | −−− |

+++ 0.01 to 0.1 μM
++ >0.1 to 0.5 μM
+ >0.5 to 10 μM
− >10 to 50 μM
−− >50 to 100 μM
−−− >100 μM

Example 37—Isothermal Titration Calorimetry (ITC)

ITC experiments were performed using a MicorCal PEAQ ITC instrument. Prior to the experiments, LDHA was dialyzed against 50 mM potassium phosphate buffer pH 7.4, 150 mM NaCl, 0.002% pluronic acid F-127 at 4° C. overnight using mini dialysis kits from GE Healthcare. The tested compounds were dissolved to 100 mM in DMSO. After dialysis, the protein was centrifuged at 14,000 rpm at 4° C. for 30 min. Buffer and MilliQ water for the reference cell were degassed prior to use. Protein concentration was determined by A280 nm measurements using a Nanodrop. All ITC experiments were conducted at 25° C. with stirring at 750 rpm. In a typical experiment the compound of interest was loaded into the sample cell at 20 μM and LDHA (200

µM in syringe) was titrated to the compound solution in consecutive injections. NADH (1 mM) and DMSO concentrations (2%) were matched in all solutions. Data were analyzed using the MicroCal PEAQ-ITC analysis software and fitted to a single site binding model, resulting in binding constant $K_d$, enthalpy ΔH, entropy ΔS and the stoichiometry N.

The binding results for the compounds of Examples 3, 5 and 10 are presented in Table 2. These show that the compounds are specific and bind to LDHA.

can Type Culture Collection (ATCC) were cultured in Dulbecco's modified Eagle's medium (DMEM+F12) supplemented with 10% heat inactivated Fetal Bovine Serum (FBS) and antibiotics (streptomycin and penicillin) in an incubator with 5% $CO_2$ at 37° C. All cell culture reagents were manufactured by Sigma Aldrich.

Screening Cell Viability Assay:

The effect of the compounds on cell viability was determined using the Alexa Fluor® 488 Annexin V/Dead Cell Apoptosis Kit (Thermo Fisher). Annexin V binds phospha-

TABLE 2

| Example No. | Compound | $K_d$ [nM] | ΔH [kJ/mol] | -TΔS [kJ/mol] | N |
|---|---|---|---|---|---|
| 3 | | 373 | −15.4 | 21.4 | 0.721 |
| 5 | | 671 | −18.2 | 17 | 0.548 |
| 10 | | 43.2 | −46 | 3.95 | 0.796 |

Example 38—In Vitro Testing in Cancer Cell Lines MDA-MB-231, MDA-MB-468 and MIA PaCa-2

Cell Culture:

Human breast cancer cell lines MDA-MB-468, MDA-MB-23 and pancreatic cancer cell line MIA PaCa-2 (Ameritidyl serine on the surface of apoptotic cells whereas the second dye Propidium Iodide (PI) binds nucleic acids. This marker does not enter intact cells and thus selectively stains dead cells. The cells were seeded at 10,000 cells per well in a 96-well culture plate in 200 µL culture medium. After an incubation of 16 hr the compounds were added to the cells in a concentration dependent manner with the highest concentration being 100 µM. Cell viability was determined after 24, 72 and 120 hr. The supernatants were collected to include detached cells. The adherent cells were detached with 0.05% trypsin and combined with the supernatants. The samples were washed with phosphate buffered saline (PBS) and incubated with Annexin V and PI in Annexin-binding buffer for 15 minutes. The cells were analyzed using the LSRFortessa (or LSRII) flow cytometer immediately after the incubation. The following controls were included in the assessment—untreated cells, control with DMSO only, and 2-deoxy-glucose (2-DOG), 2-DOG is a known inhibitor of glycolysis (Wick el al., J. Biol Chem. 224, (2): 953-959, 1957) and in this case was used as a positive control for cell death. Data were analyzed using FlowJo (Treestar).

The flow-based Annexin cell viability assay described above was used as a screening assay with low cell-numbers in a 96-well format to facilitate the testing of many compounds using different conditions. The effects of certain compounds on the glycolytic pathway of different cancer cell types and their apoptotic properties were evaluated using Lactate assays and Caspase assays, respectively.

Lactate Assay:

The inhibitory effect of the compounds on the glycolytic pathway was tested by measuring the lactate production of cancer cells. Cells were seeded in a 96-well culture plate at a density of 20,000 cells per well in 200 µL complete culture medium. The following day, the medium was removed and fresh medium as well as in 2-fold serial dilutions including 10 individual data points with a starting concentration of 90 µM were added. The cells were further incubated for 75 min at 37° C. 50 µL of the total 100 µL cell culture medium of each well was assayed by mixing with 50 µL "Microdialysis"-Lactate reagent (prepared per the manufacturer's instructions). The formation of the red-violet colored quinoneimine was photometrically measured at 530 nm after 15 min and is proportional to the lactate produced in the cells. A standard curve was prepared in parallel to each experiment, using a dilution series of lactate (Abcam) ranging from 0 to 20 nmoles. Data was analyzed using KaleidaGraph (www.synergy.com) and $IC_{50}$ values determined using a standard 4-parameter fit (Levenberg-Marquardt fitting procedure).

Caspase Assay:

The effect of a selected compound on cell viability was determined in detail using the CellEvent™ Caspase-3/7 Green Detection Reagent (Thermo Fisher). When added to tissue culture medium, this non-fluorescent substrate crosses the cell membrane where it is cleaved by activated caspase-3/7 of apoptotic cells resulting in the release of the green fluorescent dye and staining of nuclear DNA. Kinetic activation of caspase-3/7 can be monitored and quantified using the IncuCyte® basic analyzer.

MDA-MB-468 cells, stably expressing CytoLight Red florescence dye (introduced by lentiviral transduction with Lenti, EF-1 alpha and selected with Puromycin) were seeded at 2,000 cells per well in a 96-well culture plate in 100 µL culture medium. After an incubation of 20 hr the medium was removed and fresh medium and compounds were added to the cells in a concentration dependent manner with the highest concentration being 100 µM. Cell viability was determined by taking images with filters for green and red fluorescent signals every third hour. The rate of apoptotic cells (green signal) over the total cell number (red signals) was analyzed using the IncuCyte analysis program (Essen biosciences) and KaleidaGraph software.

Figure 1:
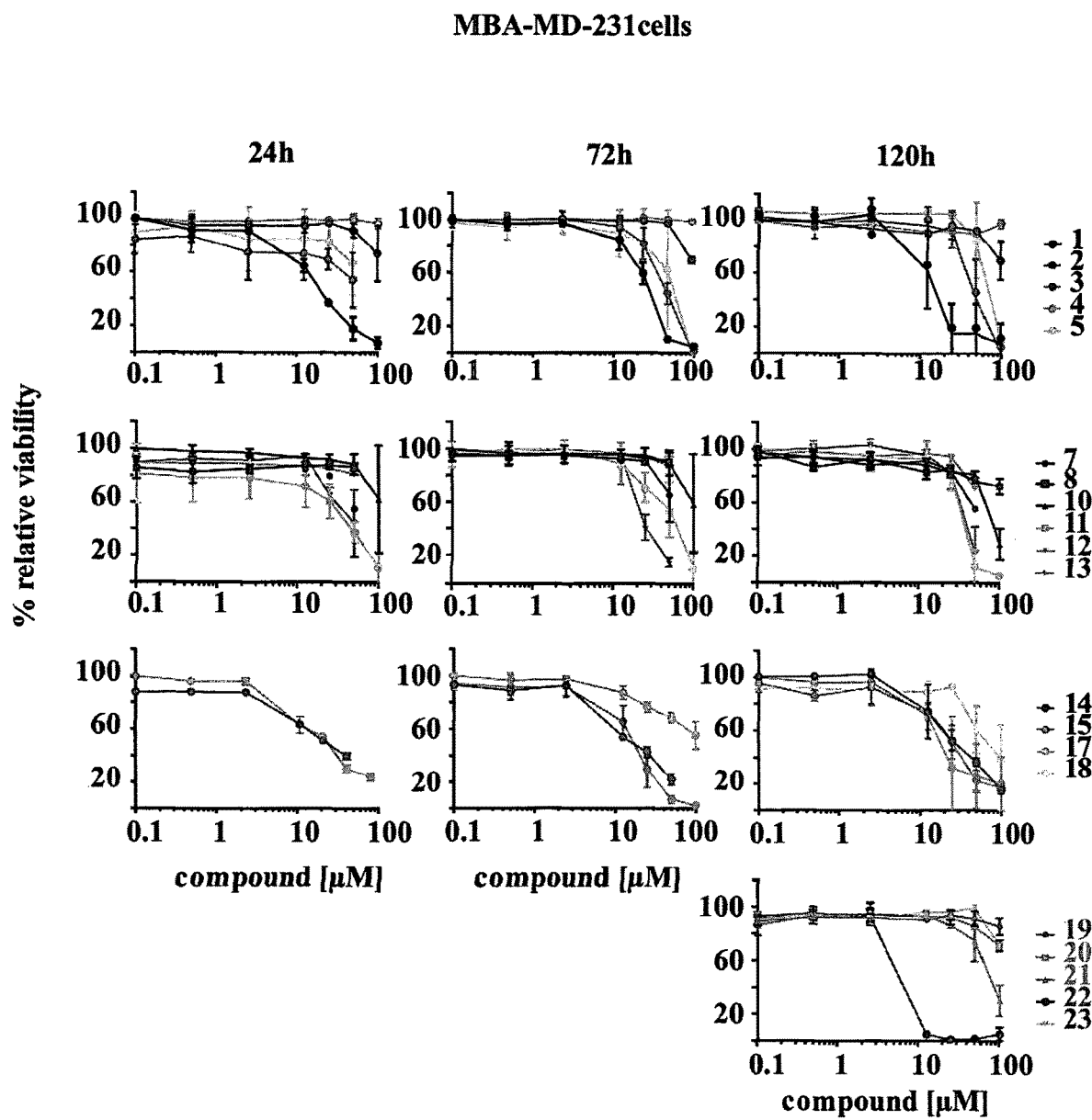
FIG. 1 shows the cell viability of MDA-MB-231 cancer cells at 24, 72 and 120 hours after incubation with various compounds according to the invention.
Figure 2:
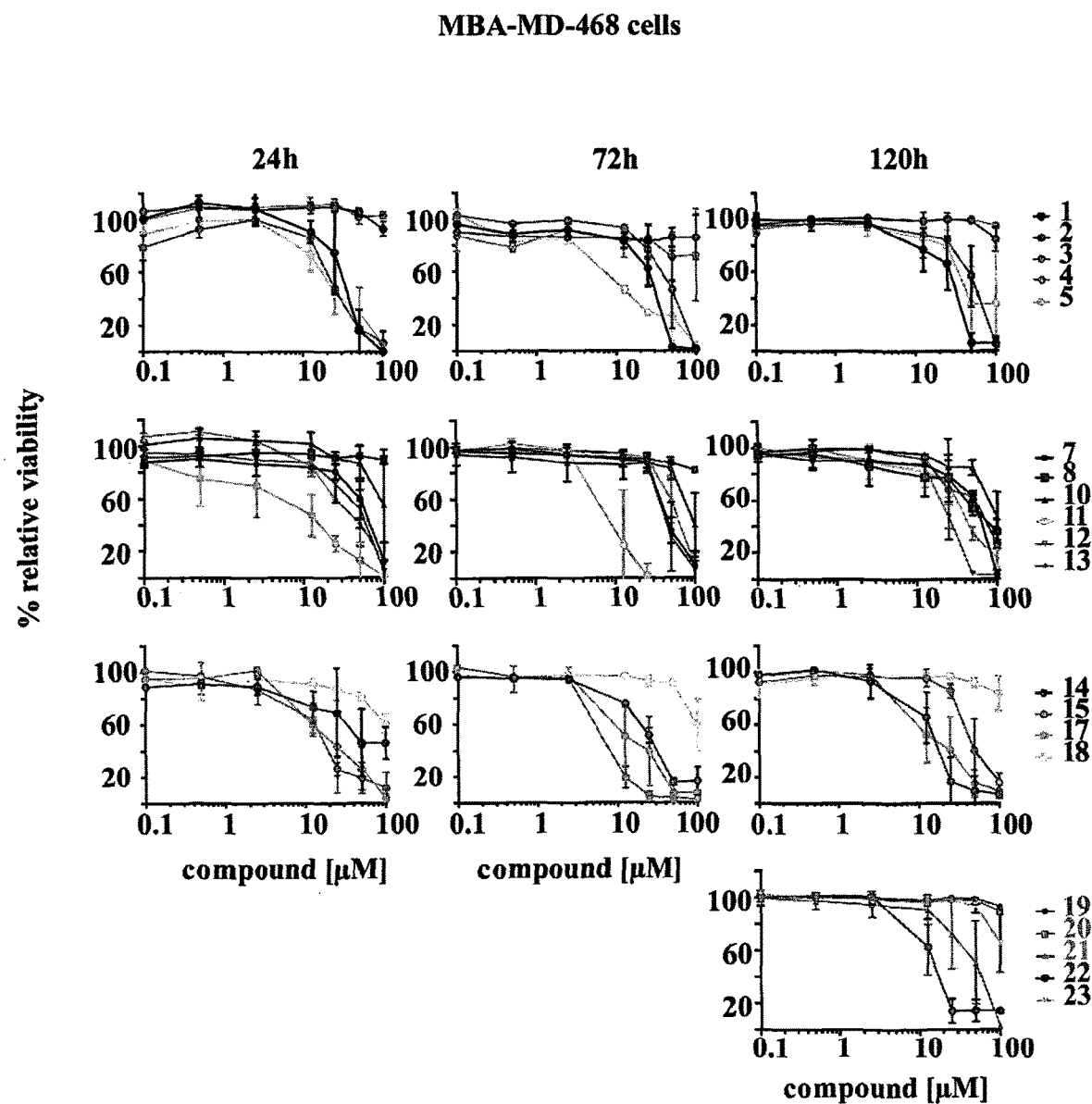
FIG. 2 shows the cell viability of MDA-MB-468 cancer cells at 24, 72 and 120 hours after incubation with various compounds according to the invention.

Results from the screening assay for various compounds of Examples 1 to 23 (denoted compounds 1 to 23) are presented in FIG. 1 and FIG. 2 for breast cell cancer cell lines MDA-MB-231 and MDA-MB-468, respectively.

Figure 3:
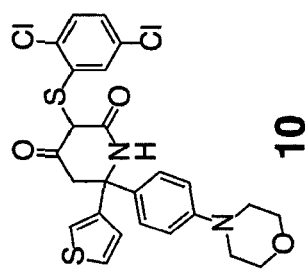
FIG. 3 shows the cell viability of MDA-MB-231 and MDA-MB-468 cancer cells at 120 hours after incubation with the known compound of Example 24 (which corresponds to Compound 44 in WO 2015/142903) and the compounds of Examples 8 and 10.
Figure 3:
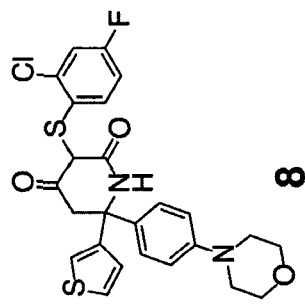
Figure 3:
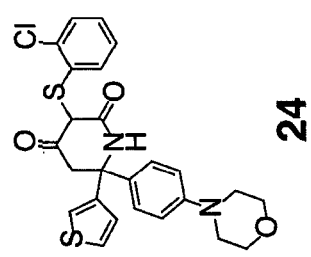
Figure 3:
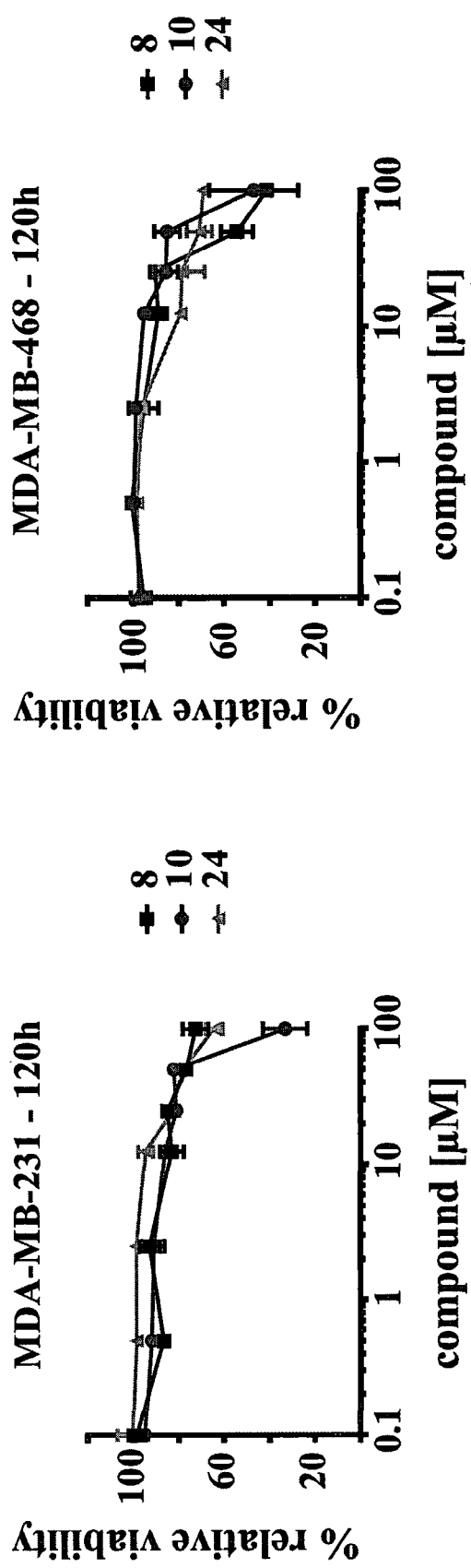

These experiments were repeated in respect of the known compounds of Examples 24 and 25 to compare the results against structurally similar compounds according to the invention. Results for the compound of Example 24 (Compound 44 in WO 2015/142903) and the compounds of Examples 8 and 10 are shown in FIG. 3.

Figure 4:
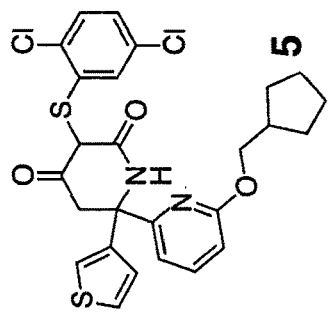
FIG. 4 shows the cell viability of MDA-MB-231 and MDA-MB-468 cancer cells at 120 hours after incubation with the known compound of Example 25 (which corresponds to Compound 194 in WO 2015/142903) and the compounds of Examples 1, 3 and 5.
Figure 4:
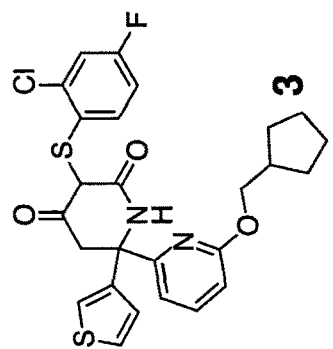
Figure 4:
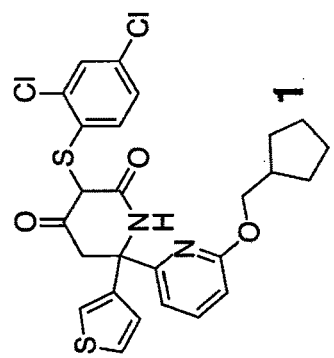
Figure 4:
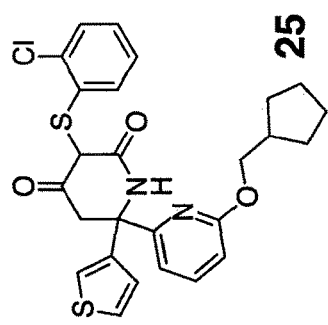
Figure 4:
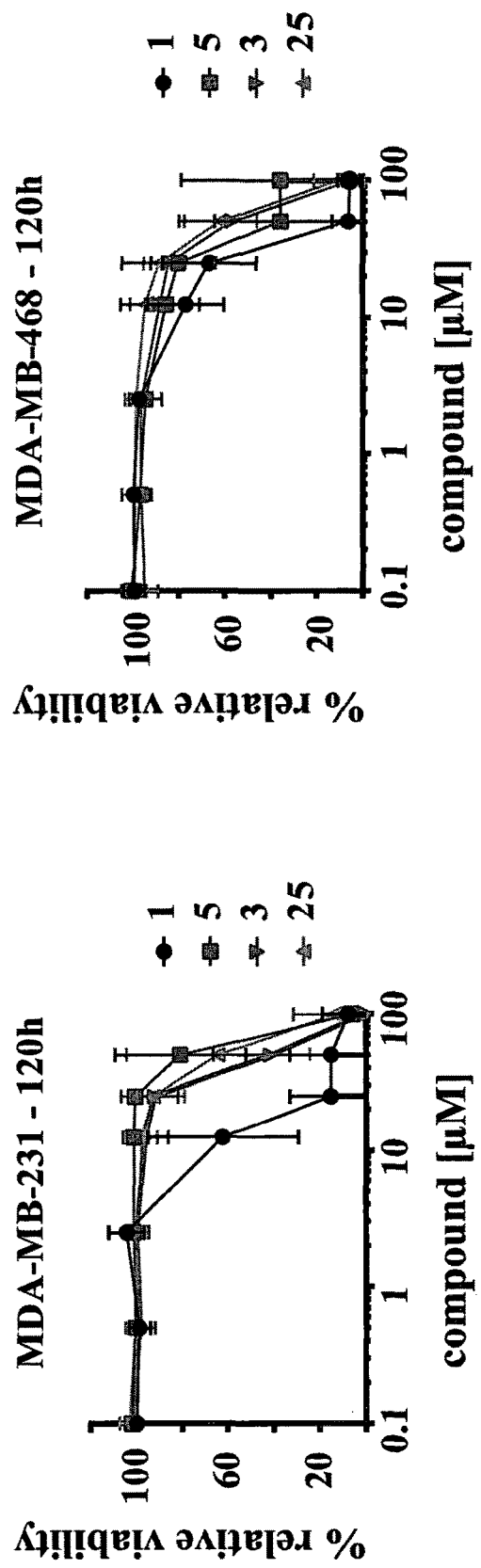

FIG. 4 shows the results for the compound of Example 25 (Compound 196 in WO 2015/142903) and the compounds of Examples 1, 3 and 5.

Figure 5:
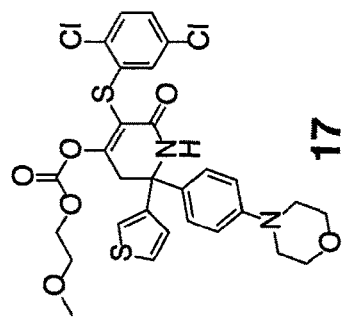
FIG. 5 shows the cell viability of MDA-MB-231 and MDA-MB-468 cancer cells at 120 hours after incubation with the compounds of Examples 10 and 17.
Figure 5:
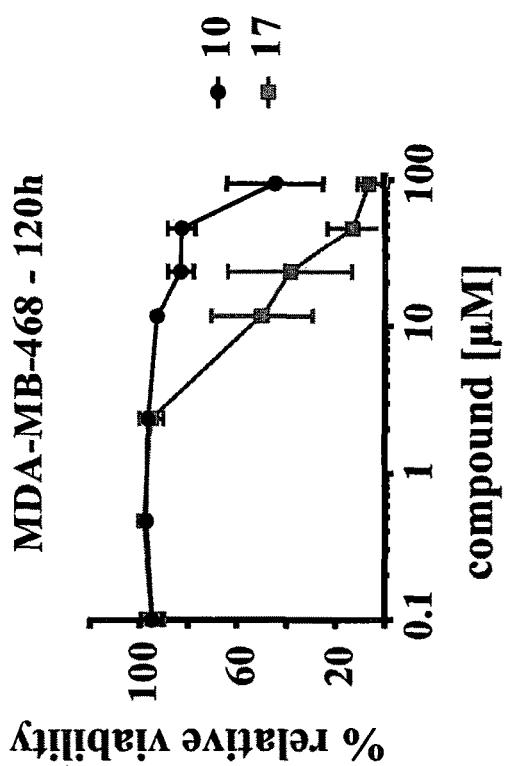
Figure 5:
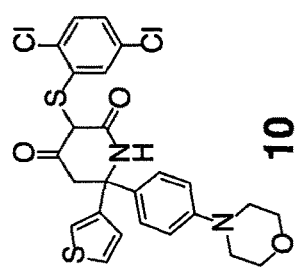
Figure 5:
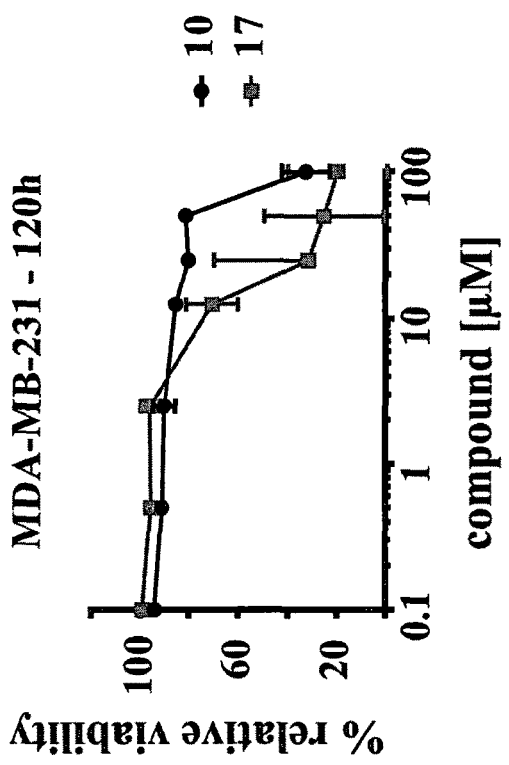

A comparison of the results for the compounds of Examples 10 and 17 is shown in FIG. 5. Example 17 is a derivative of the compound of Example 10.

Figure 6:
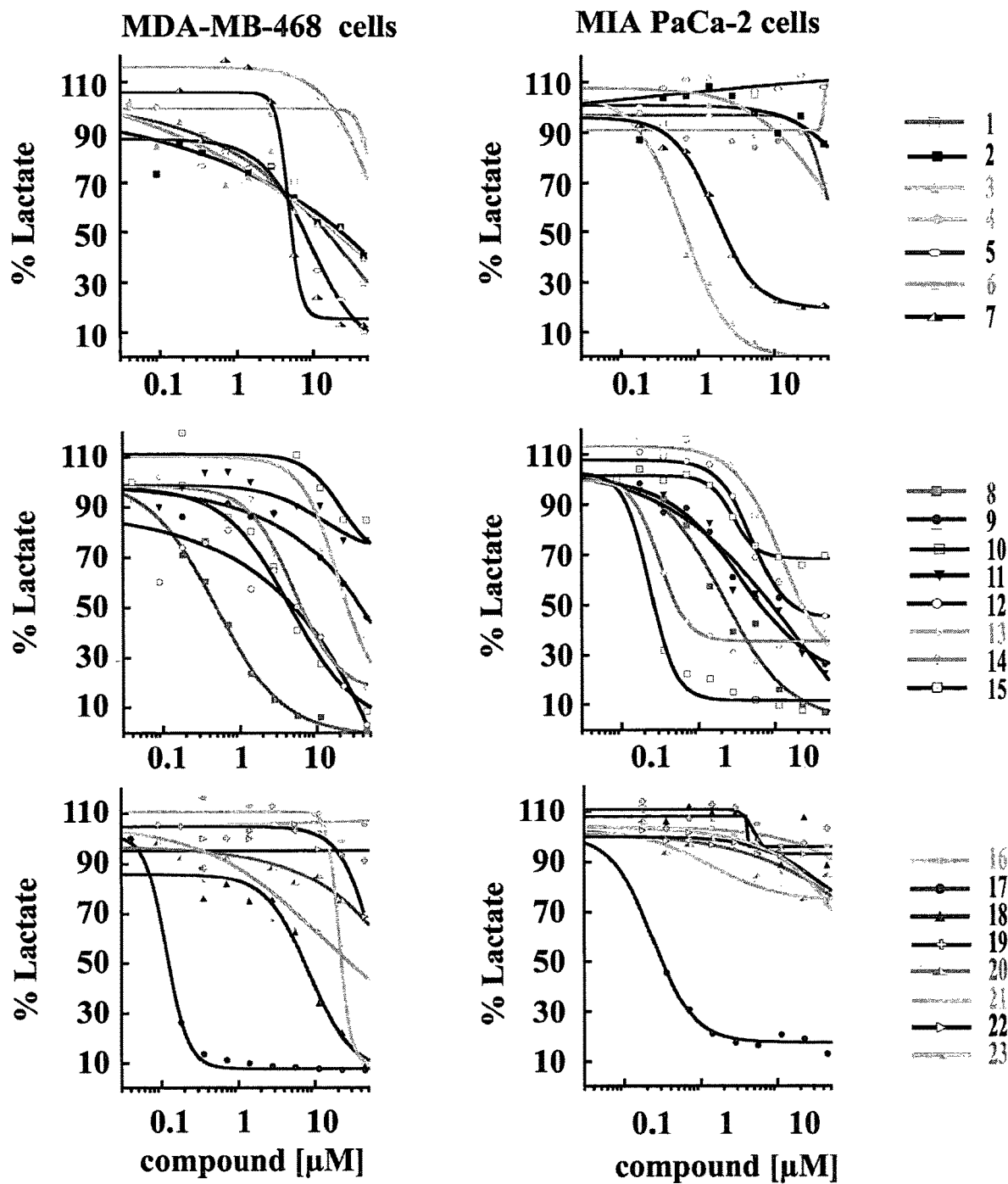
FIG. 6 shows % lactate in MDA-MB-468 cells and MIA PaCa-2 cancer cells after incubation with the compounds of Examples 1 to 23.

Results for the compounds of Examples 1 to 23 (denoted compounds 1 to 23) are presented in FIG. 6 for breast cell cancer cell line MDA-MB-468 and pancreatic cancer cell line MIA PaCa-2.

Figure 7:
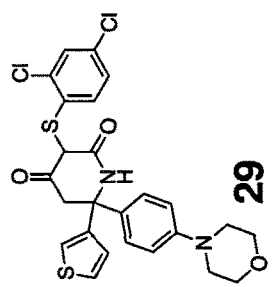
FIG. 7 shows % lactate in MDA-MB-468 cells and MIA PaCa-2 cancer cells after incubation with the compounds of Examples 8, 9, 10 and 29 compared to incubation with the known compound of Example 24 (which corresponds to Compound 44 in WO 2015/142903)
Figure 7:
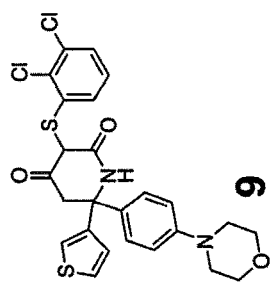
Figure 7:
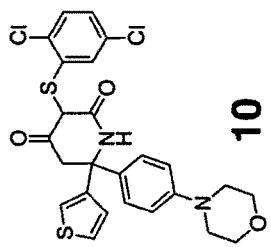
Figure 7:
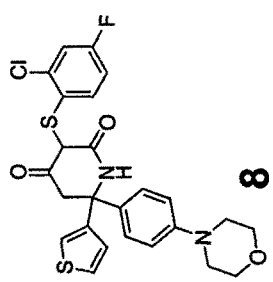
Figure 7:
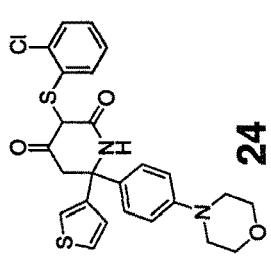
Figure 7:
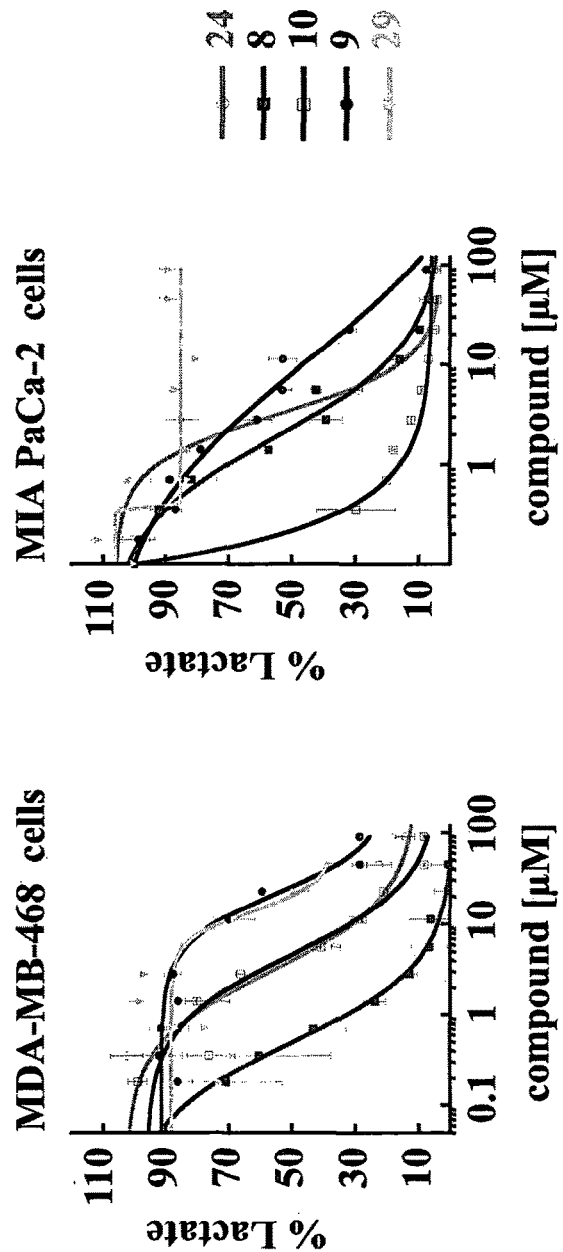

FIG. 7 shows the results for the structurally similar compounds of Examples 8, 9, 10 and 29 in comparison to the known compound of Example 24 (Compound 44 in WO 2015/142903).

Figure 8:
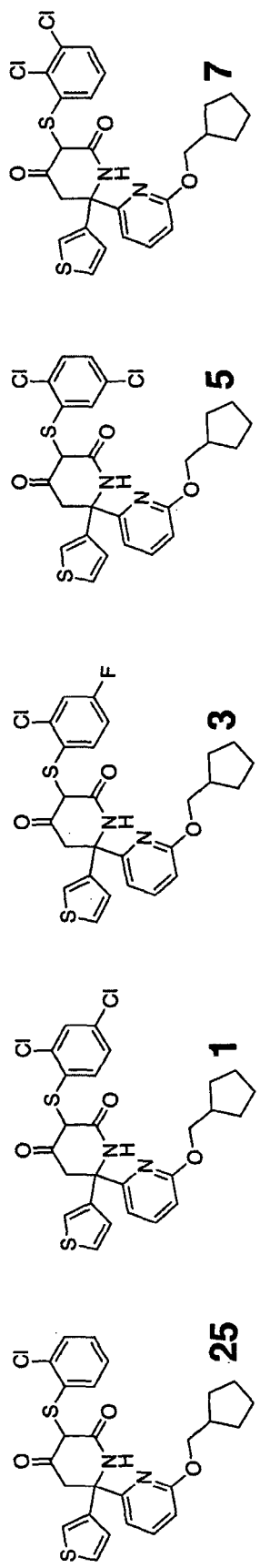
FIG. 8 shows % lactate in MDA-MB-468 cells and MIA PaCa-2 cancer cells after incubation with the compounds of Examples 1, 3, 5 and 7 compared to incubation with the known compound of Example 25 (which corresponds to Compound 194 in WO 2015/142903)
Figure 8:
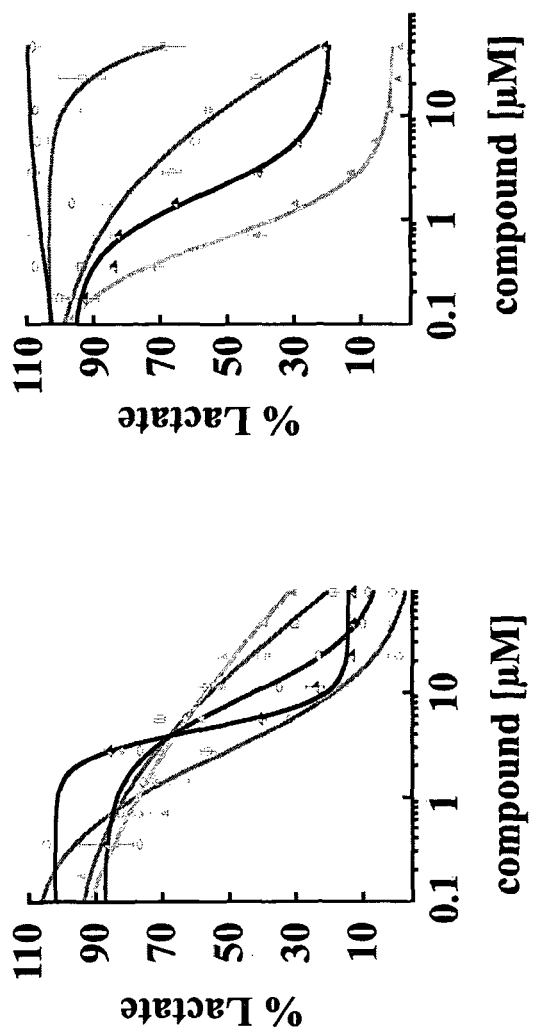

FIG. 8 shows the results for the compounds of Examples 1, 3, 5 and 7 in comparison to the compound of Example 25 (Compound 196 in WO 2015/142903).

Figure 9:
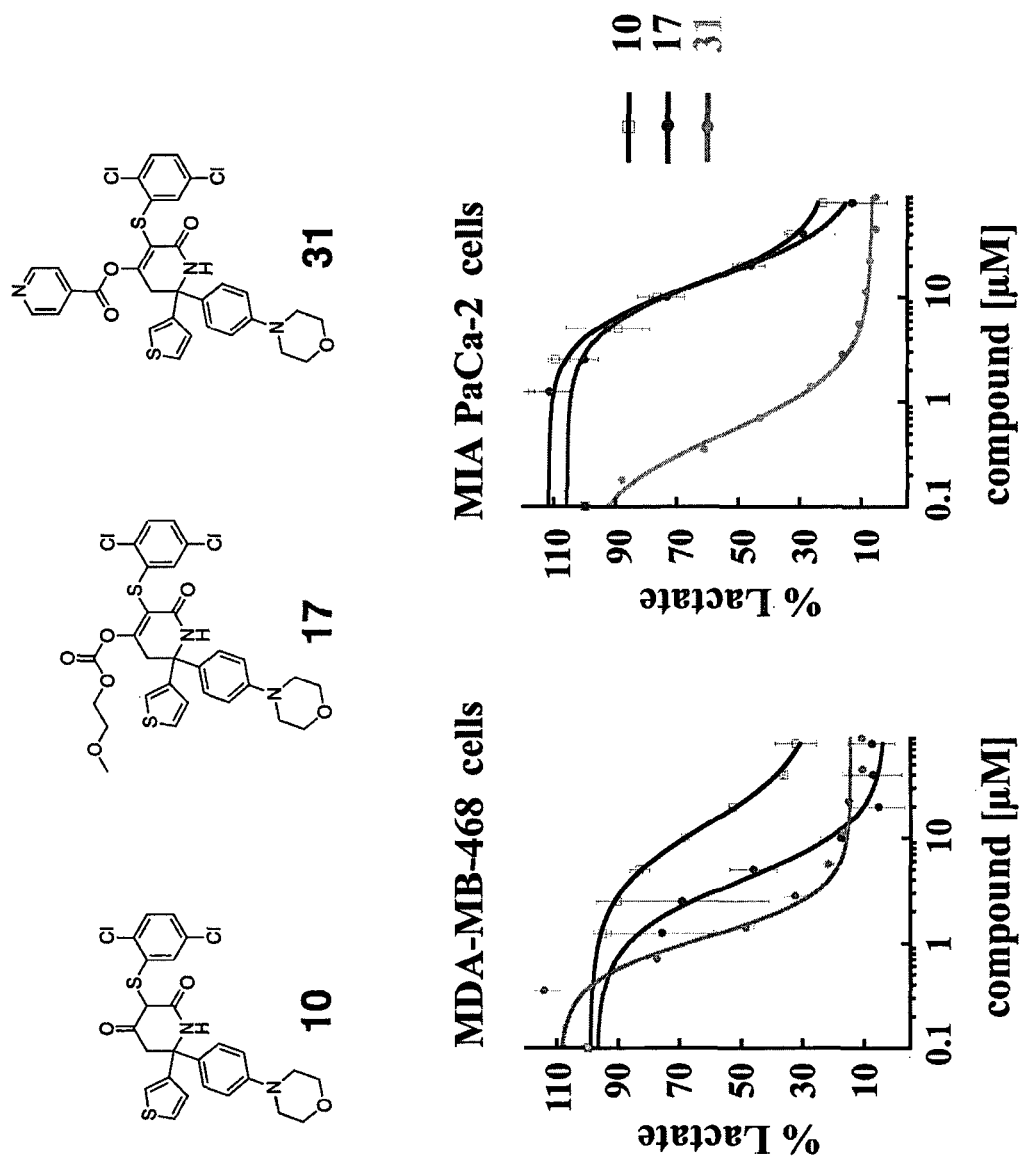
FIG. 9 shows % lactate in MDA-MB-468 cells and MIA PaCa-2 cancer cells after incubation with the compounds of Examples 10, 17 and 31.

A comparison of the results for the compounds of Examples 10 and 17 and 31 is shown in FIG. 9. The compound of Example 17 is a derivative of the compound of Example 10.

Figure 10:
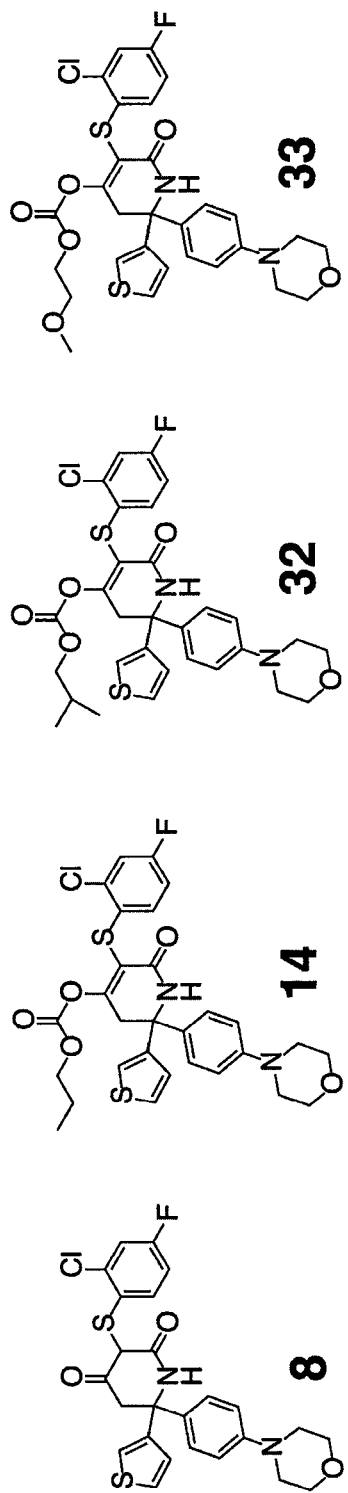
FIG. 10 shows % lactate in MDA-MB-468 cells and MIA PaCa-2 cancer cells after incubation with the compounds of Examples 8, 14, 32 and 33.
Figure 10:
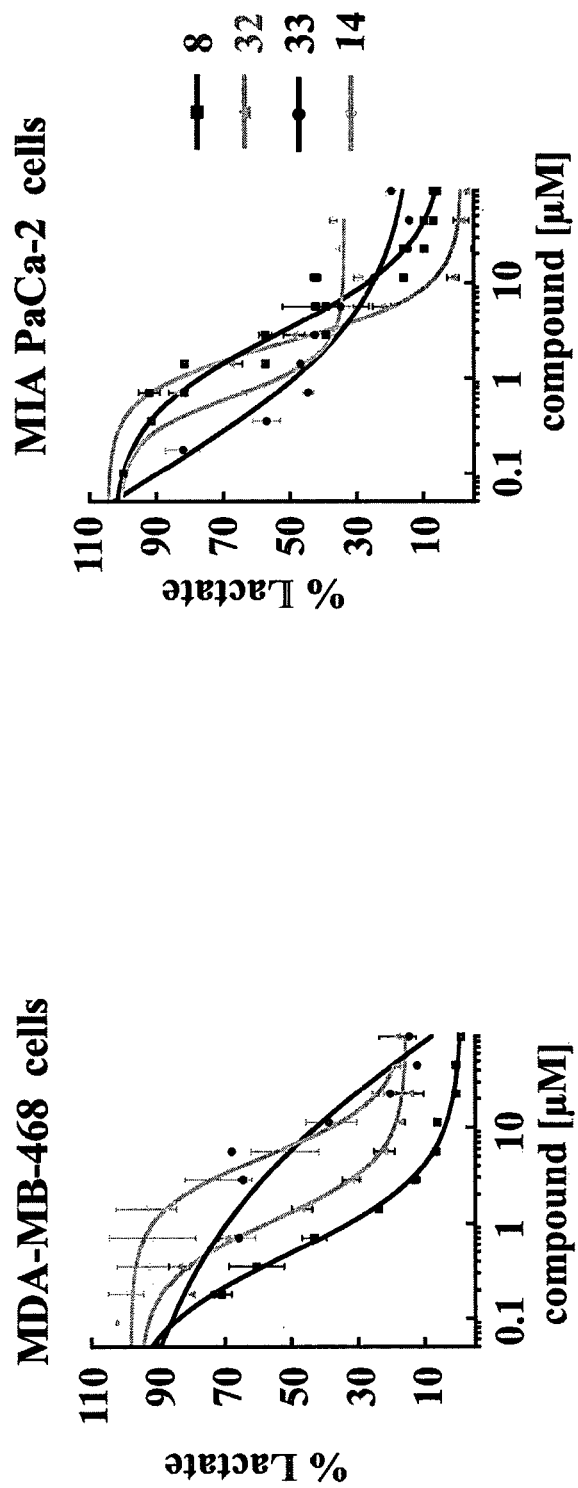

FIG. 10 shows the effects of the compounds of Examples 14, 32 and 33 in comparison to the compound of Example 8.

FIG. 11 shows a comparison of the compound of Example 10 used as a racemic mixture compared to an enriched enantiomer of the compound of Example 10 (enantiomer 1) on MDA-MB-468 cell line (left hand figure). This figures also shows the results for the enriched enantiomer of the compound of Example 10 on various other indicated cell lines also presented (right hand figure).

FIG. 12 shows the effect of compound of Example 10 cell viability of on MDA-MB-468 cell line during a time course of 120 hours (left hand figure) and live cells per % of untreated MDA-MB-468 cells after incubation for 96 hours with different concentrations of compound of Example 10 (right hand figure).

The invention claimed is:

1. A compound of formula (I), a stereoisomer, tautomer, pharmaceutically acceptable salt or prodrug thereof:

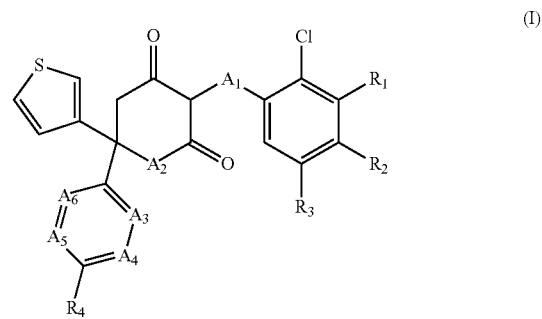

wherein:

A₁ is —O—, —CH₂—, or —S—;
A₂ is NR, wherein R is either H or $C_{1-3}$ alkyl;
A₃ is N or CR₅;
A₄ is N or CR₆;
A₅ is N or CR₇;
A₆ is N or CR₈;
R₁, R₂ and R₃ are independently selected from H and halogen;
R₄ is selected from:
  H;
  halogen;
  a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —CO₂H, —C(O)—O—$C_{1-6}$ alkyl, —C(O)—$C_{1-6}$ alkyl, amino, cyano, and nitro groups; and
  OR₉ in which R₉ is a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —CO₂H, —C(O)—O—$C_{1-6}$ alkyl, —C(O)—$C_{1-6}$ alkyl, amino, cyano, and nitro groups; and
  OR₁₀ in which R₁₀ is a $C_{3-8}$ cycloalkyl group;
R₅ is selected from:
  H;
  hydroxy;
  $C_{1-6}$ alkyl; and
  $C_{1-6}$ alkoxy;
R₆ is selected from:
  H;
  halogen;
  $C_{1-6}$ alkyl optionally substituted by one or more substituents selected from the group consisting of halogen, hydroxy, $C_{1-6}$ alkoxy, $C_{1-6}$ haloalkyl, $C_{1-6}$ hydroxyalkyl, amino, cyano, and nitro groups;
  $C_{1-6}$ alkoxy optionally substituted by one or more substituents selected from the group consisting of halogen, hydroxy, $C_{1-6}$ alkoxy, $C_{1-6}$ haloalkyl, $C_{1-6}$ hydroxyalkyl, amino, cyano, nitro, and $C_{3-8}$ cycloalkyl groups;
  a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —CO₂H, C(O)—O—$C_{1-6}$ alkyl, —C(O)—$C_{1-6}$ alkyl, amino, cyano, and nitro groups; and
  OR₁₁ in which R₁₁ is a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —CO₂H, —C(O)—O—$C_{1-6}$ alkyl, —C(O)—$C_{1-6}$ alkyl, amino, cyano, and nitro groups; and
  OR₁₂ in which R₁₂ is a $C_{3-8}$ cycloalkyl group;
R₇ and R₈ are independently selected from:
  H;
  hydroxy;
  $C_{1-6}$ alkyl; and
  $C_{1-6}$ alkoxy;
with the provisos that:
  A₃ and A₄ are not both N at the same time;
  A₅ and A₆ are not both N at the same time; and
  at least one of R₁, R₂ and R₃ is halogen.

2. The compound of claim 1 having the formula (Ia), a stereoisomer, tautomer, pharmaceutically acceptable salt, or prodrug thereof:

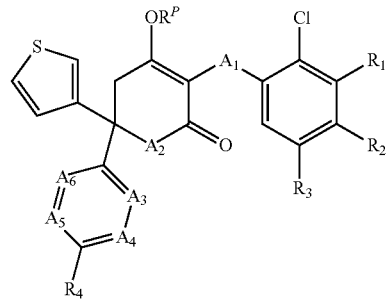

(Ia)

wherein A₁ to A₆ and R₁ to R₄ are as defined in claim 1; and
$R^P$ is either H or a group having the formula (II):

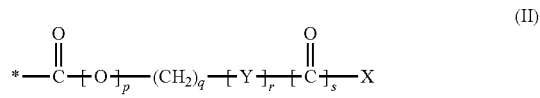

(II)

wherein:
* denotes the point of attachment of the group to the remainder of the molecule;
Y is —O— or $NR^i$ where $R^i$ is either H or $C_{1-3}$ alkyl;
X is selected from:
  H;
  hydroxy;
  $NR^jR^k$ where $R^j$ and $R^k$ are each independently selected from H and $C_{1-6}$ alkyl;
  —$C_{1-12}$ alkyl optionally substituted by one or more hydrophilic groups which are independently selected from: —OR', wherein R' is either H or $C_{1-3}$ alkyl, and —NR''₂, wherein each R'' is independently selected from H and $C_{1-3}$ alkyl;
  —$C_{1-12}$ alkyl optionally substituted by one or more aryl or heteroaryl groups, which aryl and heteroaryl groups may optionally be substituted by one or more substituents selected from the group consisting of: halo, hydroxy, $C_{1-6}$ alkyl, $C_{1-6}$ alkoxy, $C_{1-6}$ haloalkyl, $C_{1-6}$ haloalkoxy and $C_{1-6}$ hydroxyalkyl groups; and
  an aryl or heteroaryl group which may optionally be substituted by one or more substituents selected from the group consisting of: halo, hydroxy, $C_{1-6}$ alkyl, $C_{1-6}$ alkoxy, $C_{1-6}$ haloalkyl, $C_{1-6}$ haloalkoxy and $C_{1-6}$ hydroxyalkyl groups;
p is 0 or 1;
q is an integer from 0 to 6;
r is 0 or 1; and
s is 0 or 1.

3. The compound of claim 1, wherein A₁ is —S—.

4. The compound of claim 1, wherein A₂ is NH.

5. The compound of claim 1 having the formula (III), or a tautomer, stereoisomer, pharmaceutically acceptable salt, or prodrug thereof:

(III)

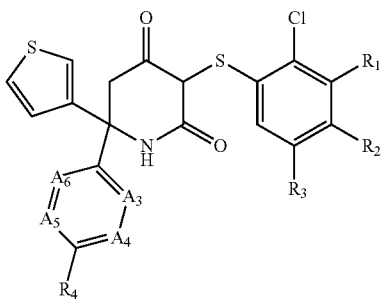

wherein $A_3$ to $A_6$, and $R_1$ to $R_4$ are as defined in claim 1.

6. The compound of claim 1, wherein $A_5$ is CH.
7. The compound of claim 1, wherein $A_6$ is CH.
8. The compound of claim 1, wherein $A_3$ is N.
9. The compound of claim 1, wherein $A_4$ is $CR_6$.
10. The compound of claim 1, wherein $R_4$ is H.
11. The compound of claim 1 having the formula (V), or a tautomer, stereoisomer, pharmaceutically acceptable salt, or prodrug thereof:

(V)

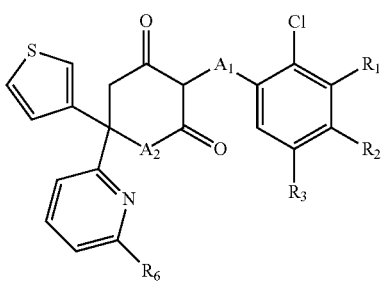

wherein $A_1$, $A_2$, $R_1$ to $R_3$, and $R_6$ are as defined in claim 1.

12. The compound of claim 1, wherein $R_6$ is halogen or an optionally substituted $C_{1-6}$ alkoxy group.
13. The compound of claim 1, wherein $R_6$ is a $C_{1-6}$ alkoxy group substituted by a $C_{3-8}$ cycloalkyl group.
14. The compound of claim 1, wherein $A_3$ is $CR_5$.
15. The compound of claim 1, wherein $A_3$ is CH and $A_4$ is $CR_6$.
16. The compound of claim 1 having the formula (VI), or a tautomer, stereoisomer, pharmaceutically acceptable salt, or prodrug thereof:

(VI)

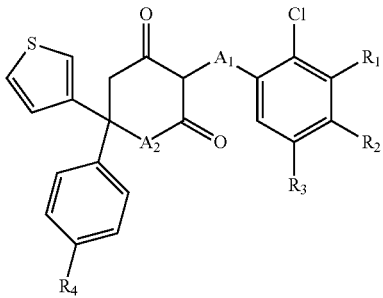

wherein $A_1$, $A_2$, and $R_1$ to $R_4$ re as defined in claim 1.

17. The compound of claim 1, wherein $R_4$ is selected from:
H
halogen; and
a 4- to 6-membered heterocyclic ring optionally substituted by one or more substituents selected from the group consisting of halogen, hydroxy, $C_{1-6}$ alkyl, $C_{1-6}$ alkoxy, $C_{1-6}$ haloalkyl, $C_{1-6}$ hydroxyalkyl, —$CO_2H$, —C(O)—O—$C_{1-6}$ alkyl, —C(O)—$C_{1-6}$ alkyl, amino, cyano, and nitro groups.

18. The compound of claim 1, wherein $R_4$ is H, Br or morpholinyl.
19. The compound of claim 1, wherein one or two of $R_1$, $R_2$ and $R_3$ are halogen.
20. The compound of claim 1, wherein $R_1$ is halogen and $R_2$ and $R_3$ are H, wherein $R_2$ is halogen and $R_1$ and $R_3$ are H, or wherein $R_3$ is halogen and $R_1$ and $R_2$ are H.
21. The compound of claim 1, wherein either $R_1$ or $R_3$ is —Cl, or $R_2$ is —F.
22. The compound of claim 2, wherein $R^P$ represents a group having the formula (II):

(II)

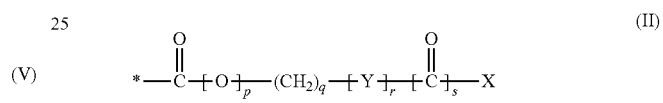

in which
Y is —O— or $NR^i$ where $R^i$ is either H or $C_{1-3}$ alkyl;
X is selected from:
$NR^jR^k$ where $R^j$ and $R^k$ are each independently selected from H and $C_{1-6}$ alkyl;
—$C_{1-12}$ alkyl optionally substituted by one or more hydrophilic groups independently selected from: —OR', wherein R' is either H or $C_{1-3}$ alkyl, and —$NR''_2$, wherein each R'' is independently selected from H and $C_{1-3}$ alkyl; and
an aryl or heteroaryl group which may optionally be substituted by one or more substituents selected from the group consisting of: halo, hydroxy, $C_{1-6}$ alkyl, $C_{1-6}$ alkoxy, $C_{1-6}$ haloalkyl, $C_{1-6}$ haloalkoxy and $C_{1-6}$ hydroxyalkyl groups; and
p, q, r and s are as defined in claim 2.

23. The compound of claim 2, wherein Y is —O—.
24. The compound of claim 2, wherein X is $C_{1-12}$ alkyl optionally substituted by one or more groups selected from: —OR', wherein R' is either H or $C_{1-3}$ alkyl, and —$NR''_2$, wherein each R'' is independently selected from H and $C_{1-3}$ alkyl.
25. The compound of claim 2, wherein $R^P$ is a group of formula (VII):

*—CO—O—$(CH_2)_q$—X     (VII)

in which * and q are as defined in claim 2; and
X is as defined in claim 2.

26. The compound of claim 25, wherein the group of formula (VII) is selected from any of the following:

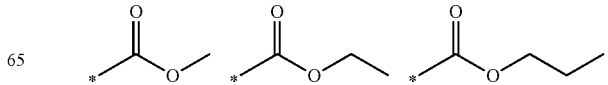

-continued

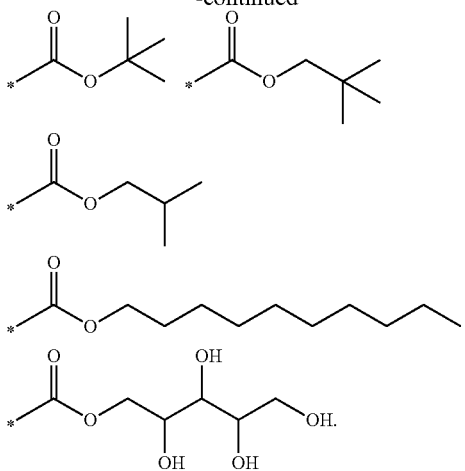

27. The compound of claim 2, wherein $R^P$ is a group of formula (VIII):

in which * and q are as defined in claim 2; and
X is as defined in claim 2.

28. The compound of claim 27, wherein the group of formula (VIII) is selected from any of the following:

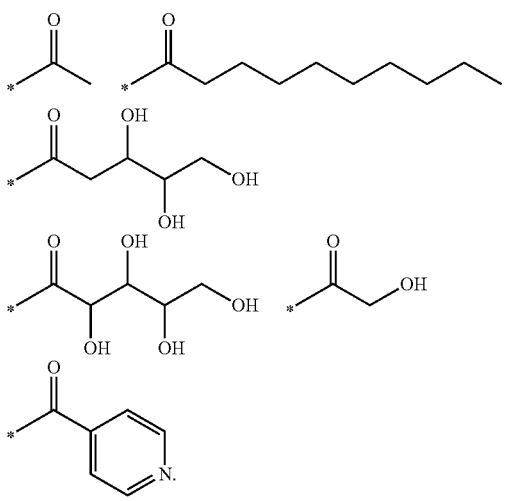

29. The compound of claim 2, wherein $R^P$ is a group of formula (IX):

in which * and q are as defined in claim 2; and
X is as defined in claim 2.

30. The compound of claim 29, wherein the group of formula (IX) is:

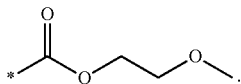 [SMILES: *C(=O)OCCOC]

31. The compound of claim 2, wherein $R^P$ is a group of formula (X):

in which * and q are as defined in claim 2; and
X is as defined in claim 2.

32. The compound of claim 31, wherein the group of formula (X) is:

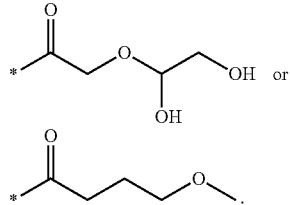

33. The compound of claim 2, wherein $R^P$ is a group of formula (XI):

in which * and q are as defined in claim 2; and
X is as defined in claim 2.

34. The compound of claim 33, wherein the group of formula (XI) is:

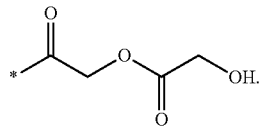 [SMILES: *C(=O)COC(=O)CO]

35. The compound of claim 1 selected from the following:
6-[6-(cyclopentylmethoxy)pyridin-2-yl]-3-[(2,4-dichlorophenyl)sulfanyl]-6-(thiophen-3-yl)piperidine-2,4-dione;
6-(6-bromopyridin-2-yl)-3-[(2-chloro-4-fluorophenyl)sulfanyl]-6-(thiophen-3-yl)piperidine-2,4-dione;
3-[(2-chloro-4-fluorophenyl)sulfanyl]-6-[6-(cyclopentylmethoxy)pyridin-2-yl]-6-(thiophen-3-yl)piperidine-2,4-dione;
3-((2-chloro-4-fluorophenyl)thio)-6-(6-ethoxypyridin-2-yl)-6-(thiophen-3-yl)piperidine-2,4-dione;
6-[6-(cyclopentylmethoxy)pyridin-2-yl]-3-[(2,5-dichlorophenyl)sulfanyl]-6-(thiophen-3-yl)piperidine-2,4-dione;
6-(6-bromopyridin-2-yl)-3-[(2,3-dichlorophenyl)sulfanyl]-6-(thiophen-3-yl)piperidine-2,4-dione;
6-[6-(cyclopentylmethoxy)pyridin-2-yl]-3-[(2,3-dichlorophenyl)sulfanyl]-6-(thiophen-3-yl)piperidine-2,4-dione;
3-((2-chloro-4-fluorophenyl)thio)-6-(4-morpholinophenyl)-6-(thiophen-3-yl)piperidine-2,4-dione;
3-((2,3-dichlorophenyl)thio)-6-(4-morpholinophenyl)-6-(thiophen-3-yl)piperidine-2,4-dione;
3-((2,5-dichlorophenyl)thio)-6-(4-morpholinophenyl)-6-(thiophen-3-yl)piperidine-2,4-dione;
5-[(2-chloro-4-fluorophenyl)sulfanyl]-2-[6-(cyclopentylmethoxy)pyridin-2-yl]-6-oxo-2-(thiophen-3-yl)-1,2,3,6-tetrahydropyridin-4-yl ethyl carbonate;
6'-(cyclopentylmethoxy)-5-((2,3-dichlorophenyl)thio)-6-oxo-2-(thiophen-3-yl)-1,2,3,6-tetrahydro-[2,2'-bipyridin]-4-yl methyl carbonate;
5-((2-chloro-4-fluorophenyl)thio)-6'-(cyclopentylmethoxy)-6-oxo-2-(thiophen-3-yl)-1,2,3,6-tetrahydro-[2,2'-bipyridin]-4-yl acetate;

5-((2-chloro-4-fluorophenyl)thio)-2-(4-morpholinophenyl)-6-oxo-2-(thiophen-3-yl)-1,2,3,6-tetrahydropyridin-4-yl propyl carbonate;

5-((2,3-dichlorophenyl)thio)-2-(4-morpholinophenyl)-6-oxo-2-(thiophen-3-yl)-1,2,3,6-tetrahydropyridin-4-yl ethyl carbonate;

6'-(cyclopentylmethoxy)-5-((2,5-dichlorophenyl)thio)-6-oxo-2-(thiophen-3-yl)-1,2,3,6-tetrahydro-[2,2'-bipyridin]-4-yl decyl carbonate;

5-((2,5-dichlorophenyl)thio)-2-(4-morpholinophenyl)-6-oxo-2-(thiophen-3-yl)-1,2,3,6-tetrahydropyridin-4-yl (2-methoxyethyl) carbonate;

6'-(cyclopentylmethoxy)-5-((2,4-dichlorophenyl)thio)-6-oxo-2-(thiophen-3-yl)-1,2,3,6-tetrahydro-[2,2'-bipyridin]-4-yl (2-methoxyethyl) carbonate;

5-((2,5-dichlorophenyl)thio)-2-(4-morpholinophenyl)-6-oxo-2-(thiophen-3-yl)-1,2,3,6-tetrahydropyridin-4-yl isobutyl carbonate;

5-((2,5-dichlorophenyl)thio)-2-(4-morpholinophenyl)-6-oxo-2-(thiophen-3-yl)-1,2,3,6-tetrahydropyridin-4-yl acetate;

5-((2,5-dichlorophenyl)thio)-2-(4-morpholinophenyl)-6-oxo-2-(thiophen-3-yl)-1,2,3,6-tetrahydropyridin-4-yl pivalate;

3-((2,4-dichlorophenyl)thio)-6-(4-morpholinophenyl)-6-(thiophen-3-yl)piperidine-2,4-dione;

5-((2,4-dichlorophenyl)thio)-2-(4-morpholinophenyl)-6-oxo-2-(thiophen-3-yl)-1,2,3,6-tetrahydropyridin-4-yl (2-methoxyethyl) carbonate;

5-((2,5-dichlorophenyl)thio)-2-(4-morpholinophenyl)-6-oxo-2-(thiophen-3-yl)-1,2,3,6-tetrahydropyridin-4-yl isonicotinate;

5-((2-chloro-4-fluorophenyl)thio)-2-(4-morpholinophenyl)-6-oxo-2-(thiophen-3-yl)-1,2,3,6-tetrahydropyridin-4-yl iso-butyl carbonate;

5-((2-chloro-4-fluorophenyl)thio)-2-(4-morpholinophenyl)-6-oxo-2-(thiophen-3-yl)-1,2,3,6-tetrahydropyridin-4-yl (2-methoxyethyl) carbonate;

6'-(cyclopentylmethoxy)-5-((2,5-dichlorophenyl)thio)-6-oxo-2-(thiophen-3-yl)-1,2,3,6-tetrahydro-[2,2'-bipyridin]-4-yl (2-methoxyethyl) carbonate;

and their stereoisomers, tautomers, pharmaceutically acceptable salts, and prodrugs thereof.

36. The compound of claim 2 having the formula (IIIa), or a tautomer, stereoisomer, pharmaceutically acceptable salt, or prodrug thereof:

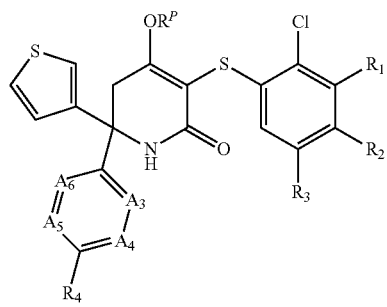

(IIIa)

wherein $A_3$ to $A_6$, $R_1$ to $R_4$ and $R^P$ are as defined in claim 2.

37. The compound of claim 2 having the formula (Va), or a tautomer, stereoisomer, pharmaceutically acceptable salt, or prodrug thereof:

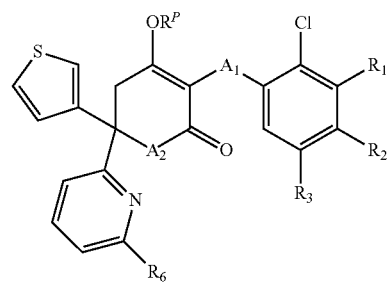

(Va)

wherein $A_1$, $A_2$, $R_1$ to $R_3$, $R_6$ and $R^P$ are as defined in claim 2.

38. The compound of claim 2 having the formula (VIa), or a tautomer, stereoisomer, pharmaceutically acceptable salt, or prodrug thereof:

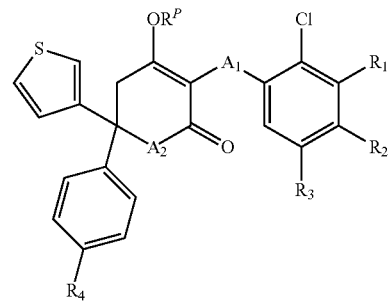

(VIa)

wherein $A_1$, $A_2$, $R_1$ to $R_4$ and $R^P$ are as defined in claim 2.

* * * * *